US011414626B2

(12) United States Patent
Dhawan et al.

(10) Patent No.: US 11,414,626 B2
(45) Date of Patent: Aug. 16, 2022

(54) SURFACTANT COMPOSITIONS AND USE THEREOF

(71) Applicant: Ecolab USA Inc., St. Paul, MN (US)

(72) Inventors: Ashish Dhawan, Aurora, IL (US); Carter Martin Silvernail, Burnsville, MN (US); Sukhwan Soontravanich, Inver Grove Heights, MN (US); Keith Allen Monk, New Braunfels, TX (US); Michael L. Braden, Huntsville, TX (US); Paige Mary Owens, Blaine, MN (US); Kerrie Elizabeth Walters, Minneapolis, MN (US); Ali Marie Bichler, Burnsville, MN (US); Izabela A. Owsik, College Station, TX (US); David Myers, Angleton, TX (US)

(73) Assignee: Ecolab USA Inc., St. Paul, MN (US)

( * ) Notice: Subject to any disclaimer, the term of this patent is extended or adjusted under 35 U.S.C. 154(b) by 297 days.

(21) Appl. No.: 16/700,843

(22) Filed: Dec. 2, 2019

(65) Prior Publication Data

US 2020/0172831 A1    Jun. 4, 2020

Related U.S. Application Data

(60) Provisional application No. 62/773,676, filed on Nov. 30, 2018.

(51) Int. Cl.
| | | |
|---|---|---|
| *B01D 65/02* | (2006.01) | |
| *C07C 43/315* | (2006.01) | |
| *C11D 1/72* | (2006.01) | |
| *C11D 17/00* | (2006.01) | |
| *C11D 3/37* | (2006.01) | |
| *C11D 11/00* | (2006.01) | |
| *C07C 211/45* | (2006.01) | |

(52) U.S. Cl.
CPC .............. *C11D 1/721* (2013.01); *B01D 65/02* (2013.01); *C07C 43/315* (2013.01); *C07C 211/45* (2013.01); *C11D 3/3773* (2013.01); *C11D 11/0011* (2013.01); *C11D 17/0021* (2013.01)

(58) Field of Classification Search
CPC .. B01D 65/02; C11D 11/0011; C11D 17/0021
See application file for complete search history.

(56) References Cited

U.S. PATENT DOCUMENTS

| | | |
|---|---|---|
| 2,832,795 A | 4/1958 | Hempel et al. |
| 3,383,326 A | 5/1968 | Seale et al. |
| 4,502,977 A | 3/1985 | Buriks et al. |
| 5,609,794 A | 3/1997 | Taylor |
| 5,653,886 A | 8/1997 | Kerr et al. |
| 6,294,093 B1 | 9/2001 | Selvarajan et al. |
| 6,638,983 B1 | 10/2003 | Taylor |
| 6,846,793 B1 | 1/2005 | Griese |
| 8,801,867 B2 | 8/2014 | Besemer et al. |
| 2004/0138084 A1 | 7/2004 | Gohl et al. |
| 2006/0247143 A1 | 11/2006 | Gallagher et al. |
| 2007/0054832 A1 | 3/2007 | Hocking et al. |
| 2008/0221293 A1 | 9/2008 | Yoneda et al. |
| 2009/0305933 A1 | 12/2009 | Stokes et al. |
| 2011/0009675 A1 | 1/2011 | Tirtowidjojo et al. |
| 2012/0083437 A1 | 4/2012 | Choczaj et al. |
| 2013/0223803 A1 | 8/2013 | Yamaguchi et al. |
| 2014/0005273 A1 | 1/2014 | Griese et al. |
| 2014/0272156 A1 | 9/2014 | Palmer, Jr. et al. |
| 2015/0175936 A1* | 6/2015 | Kingma ............... C11D 1/721 510/162 |
| 2016/0032170 A1 | 2/2016 | Li et al. |
| 2017/0037299 A1* | 2/2017 | Li ........................ C09K 8/588 |
| 2017/0211019 A1 | 7/2017 | Sivik et al. |
| 2017/0218134 A1 | 8/2017 | Tuerk et al. |
| 2017/0335254 A1 | 11/2017 | Man et al. |
| 2018/0169713 A1* | 6/2018 | Muller ................ C11D 3/2086 |
| 2019/0315656 A1* | 10/2019 | Ran ........................ C04B 24/30 |

FOREIGN PATENT DOCUMENTS

| | | |
|---|---|---|
| CN | 103044293 A | 4/2013 |
| CN | 104592167 A | 5/2015 |
| CN | 104693391 A | 6/2015 |
| DE | 2348576 A1 | 4/1975 |
| EP | 3 415 571 A1 | 12/2018 |
| JP | S6284036 A | 4/1987 |
| JP | H0195150 A | 4/1989 |

(Continued)

OTHER PUBLICATIONS

Lepper Herbert et al—DE 2348576A1 Machine Translation—Apr. 3, 1975 (Year: 1975).*
Misaka, Hideki et al., Synthesis of End-Functionalized Polyethers by Phosphazene Base-Catalyzed Ring-Opening Polymerization of 1,2-Butylene Oxide and Glycidyl Ether, Journal of Polymer Science Part A: Polymer Chemistry 2012, 50, pp. 1941-1952.
Morinaga, Hisatoyo et al., Metal-free synthesis of reactive oligomers by ring-opening oligomerization of glycidyl phenyl ether initiated with tetra-n-butylammonium fluoride in the presence of various protic compounds, Tetrahedron Letters 55 (2014) pp. 3768-3770.

(Continued)

*Primary Examiner* — Bradley R Spies
(74) *Attorney, Agent, or Firm* — Stinson LLP

(57) ABSTRACT

Surfactants capable of releasing and/or dissolving polymers to form water-soluble or water-dispersible polymer solutions are disclosed. In addition, polymer compositions containing a water-in-oil emulsion comprising the surfactant are provided and can be used, for example, in methods of dissolving a polymer. Also disclosed are detergent compositions and methods of cleaning articles and/or membranes using the surfactants herein. These surfactants and polymer compositions can be used in various industries including for water clarification, papermaking, sewage and industrial water treatment, drilling mud stabilizers, and enhanced oil recovery.

16 Claims, 19 Drawing Sheets

(56) References Cited

FOREIGN PATENT DOCUMENTS

| WO | 9915012 A1 | 4/1999 |
| WO | 2011/071497 A1 | 6/2011 |
| WO | 2016/096589 A1 | 6/2016 |
| WO | 2017/200737 A1 | 11/2017 |
| WO | 2017/205334 A1 | 11/2017 |

OTHER PUBLICATIONS

Niederer, Kerstin et al., Catechol Acetonide Glycidyl Ether (CAGE): A Functional Epoxide Monomer for Linear and Hyperbranched Multi-Catechol Functional Polyether Architectures, Macromolecules 2016, 49, pp. 1655-1665.

Zhang, Ya et al., Synthesis and Properties of Mono or Double Long-Chain Alkanolamine Surfactants, J. Surfact. Deterg (2013) 16, pp. 841-848.

International Search Report and Written Opinion dated Jun. 30, 2020 relating to PCT/US2019/063999, 15 pages.

* cited by examiner

SURFACTANT COMPOSITIONS AND USE THEREOF

CROSS REFERENCE TO RELATED APPLICATIONS

This application claims priority to U.S. Provisional Patent Application Ser. No. 62/773,676 filed on Nov. 30, 2018, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Inversion surfactants comprising the compounds described herein capable of releasing and/or dissolving polymers to form water-soluble or water-dispersible polymer solutions are disclosed. In addition, polymer compositions containing a water-in-oil emulsion comprising the inversion surfactant are provided and can be used, for example, in methods of dissolving a polymer. These inversion surfactants and polymer compositions can be used in various industries including for water clarification, papermaking, sewage and industrial water treatment, drilling mud stabilizers, and enhanced oil recovery. Also provided are detergent compositions comprising the compounds described herein that can be used, for example, in methods of cleaning articles and/or membranes.

BACKGROUND OF THE INVENTION

Various synthetic and naturally-occurring water-soluble or water-dispersible polymers can be used in a variety of commercial applications. These polymers are commercially available as powders, finely-divided solids, or water-in-oil emulsion polymers that require the polymer to be dissolved in water. While the polymers are water-soluble or water-dispersible, it can be difficult to prepare solutions or homogeneous dispersions because of slow dissolution or slow dispersion into the water. Further, polymers can clump or remain as agglomerates on contact with water. Although these clumps eventually dissolve or disperse using agitation, it can be impractical to agitate the solution for a sufficiently long time to obtain complete dissolution of the polymer particles.

Additionally, surfactants, and compositions thereof, can invert and/or activate water-in-oil emulsion polymers to aid the dissolution and dispersion of those polymers. Such inversion surfactants can be used to increase the dissolution of various emulsion polymers so the time for dissolution and degree of dissolution of the polymer is increased.

To reduce the time needed for polymer solids or inverse emulsion polymers to dissolve or disperse in aqueous solution, an inversion surfactant can be used.

Ethoxylated alkylphenols and alkylphenol-formaldehyde resins, particularly containing nonylphenol moiety as one of the building blocks have been used in the industry as one class of inversion surfactants. They also are used as surfactants for cleaning solutions and detergents. However, nonylphenols and their ethoxylated derivatives are known to be toxic, specifically as endocrine-hormone disrupters. Thus, there is a need to replace these chemistries with nonylphenol-free alternatives that are more environmentally friendly.

Because of the toxicity of nonylphenols and their ethoxylated derivatives, industrial use has largely shifted to linear/branched alcohol ethoxylates (LAEs). However, LAEs are generally not as effective as nonylphenol ethoxylates. Therefore, a need exists for novel inversion surfactants that are effective for dissolving or dispersing water-soluble or water-dispersible polymers in several industries or for use as surfactants in cleaning applications.

BRIEF SUMMARY OF THE INVENTION

Disclosed herein are compounds and compositions useful as inversion surfactants and/or detergent/cleaning compositions to aid in the dissolution of polymers or in the cleaning of membranes or articles. For example, disclosed herein is the compound of Formula 1 having the structure of Formula 1:

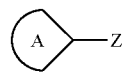

(1)

wherein A is an optionally substituted phenyl, naphthalene, indole, purine, pyridine, quinoline, isoquinoline, pyrimidine, pyrole, furan, thiophene, imidazole, or thiazole; and Z has a structure of moiety A or moiety B:

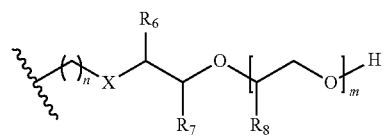

(A)

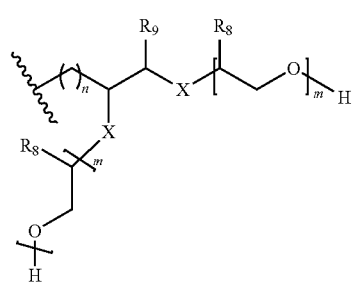

(B)

wherein X is —O—, —N($R_{10}$)—, —OC(O)—, —C(O)O—, —N($R_{10}$)C(O)—, —C(O)N($R_{10}$)—, —OC(O)O—, —OC(O)N($R_{10}$)—, —N($R_{10}$)C(O)O—, or —N($R_{10}$)C(O)N($R_{10}$)—; n is an integer from 0 to 10; $R_6$ and $R_9$ are independently hydrogen, alkyl, or aryl; $R_7$ is alkyl, aryl, or —(CH$_2$)z-O—R$_{11}$, R$_8$ is independently hydrogen, alkyl, or aryl; R$_{10}$ is hydrogen, alkyl, or Z; R$_{11}$ is hydrogen or alkyl; m is independently an integer from 3 to 20; and z is an integer from 1 to 10.

The compounds of Formula 1 can have moiety B have the structure of moiety B1 or moiety B2:

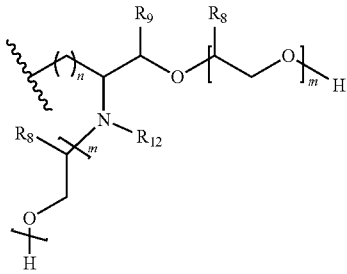

(B1)

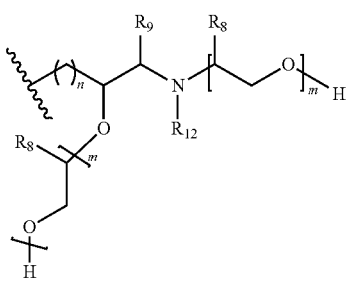

(B2)

wherein R$_9$ is independently hydrogen, alkyl, or aryl; and R$_{12}$ is independently C$_3$ to C$_{22}$ alkyl or alkenyl.

The compounds of Formula 1 can have A be an optionally substituted phenyl, naphthyl, pyridyl, quinolyl, or isoquinolyl.

The compounds of Formula 1 can have A be an optionally substituted phenyl or naphthyl.

Further, the compounds can have the structure of Formula 2:

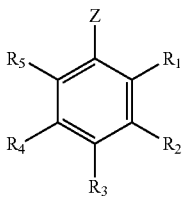

(2)

wherein R$_1$, R$_2$, R$_3$, R$_4$, and R$_5$ are independently hydrogen, Z, alkyl, alkoxyl, or two adjacent R groups combine to form a fused ring; Z has a structure of moiety A or moiety B:

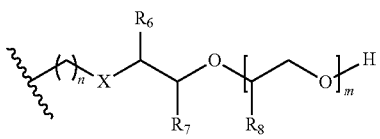

(A)

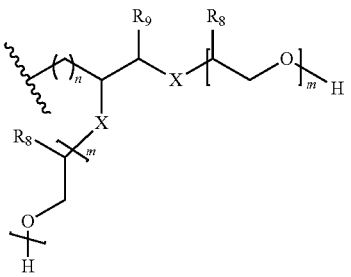

(B)

wherein X is —O—, —N(R$_{10}$)—, —OC(O)—, —C(O)O—, —N(R$_{10}$)C(O)—, —C(O)N(R$_{10}$)—, —OC(O)O—, —OC(O)N(R$_{10}$)—, —N(R$_{10}$)C(O)O—, or —N(R$_{10}$)C(O)N(R$_{10}$)—; n is an integer from 0 to 10; R$_6$ and R$_9$ are independently hydrogen, alkyl, or aryl; R$_7$ is alkyl, aryl, or —(CH$_2$)z-O—R$_{11}$, R$_8$ is independently hydrogen, alkyl, or aryl; R$_{10}$ is hydrogen, alkyl, or Z; R$_{11}$ is hydrogen or alkyl; m is an integer from 3 to 20; and z is an integer from 1 to 10.

The compounds of Formula 2 can have moiety B have the structure of moiety B1 or moiety B2:

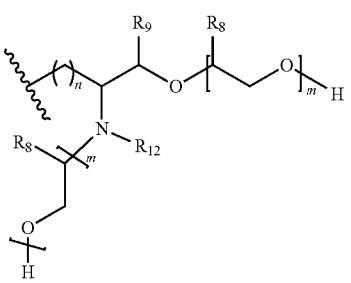

(B1)

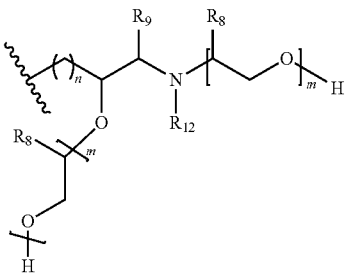

(B2)

wherein R$_9$ is independently hydrogen, alkyl, or aryl; and R$_{12}$ is independently C$_3$ to C$_{22}$ alkyl or alkenyl.

The compounds of Formula 2 can have at least one of R$_1$, R$_2$, R$_3$, R$_4$, and R$_5$ be Z.

The compound of Formula 2 can have Z have the structure of moiety A, X be —O—; n be 0; R$_1$, R$_2$, R$_3$, R$_4$, R$_5$ be hydrogen; R$_7$ be —(CH$_2$)z-O—R$_{11}$, z be 1, R$_8$ be hydrogen, R$_{11}$ be 2-ethylhexyl, and m be an integer from 7 to 13 or an integer from 7 to 12.

The compounds can have the structure of Formula 3:

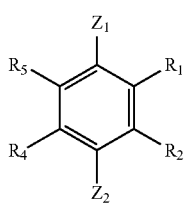
(3)

wherein $R_1$, $R_2$, $R_4$, and $R_5$ are independently hydrogen, alkyl, alkoxyl, or Z; and $Z_1$, $Z_2$, and Z independently have a structure of moiety A or moiety B:

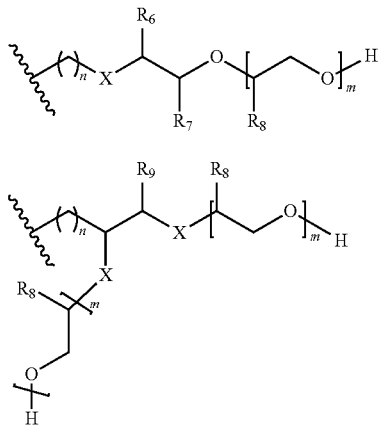

wherein X is —O— or —N($R_{10}$)—; n is an integer from 0 to 5; $R_6$ and $R_9$ are independently hydrogen or alkyl; $R_7$ is alkyl, or —(CH$_2$)z-O—$R_{11}$, $R_8$ is independently hydrogen, alkyl, or aryl; $R_{10}$ is hydrogen, alkyl, or Z; $R_{11}$ is hydrogen or alkyl; m is an integer from 3 to 20; and z is an integer from 1 to 10.

The compounds of Formula 1 or 2 can have $R_1$, $R_2$, $R_3$, $R_4$, and $R_5$ independently be hydrogen or $C_1$ to $C_4$ alkyl.

The compounds of Formula 1 or 2 can have $R_1$, $R_2$, $R_3$, $R_4$, and $R_5$ be hydrogen.

The compounds of Formula 1, 2, or 3 can have $R_6$ and $R_9$ be hydrogen.

The compounds of Formula 1, 2, or 3 can have $R_8$ be hydrogen or methyl.

The compounds Formula 1, 2, or 3 can have $R_7$ be —(CH$_2$)z-O—$R_{11}$.

The compounds of Formula 1, 2, or 3 can have z be 1 to 3.

The compounds of Formula 1, 2, or 3 can have $R_{11}$ be $C_4$ to $C_{22}$ alkyl.

The compounds of Formula 1, 2, or 3 can have X be —O— or —N($R_{10}$)—.

The compounds of Formula 1, 2, or 3 can have X be —O—.

The compounds of Formula 1, 2, or 3 can have X be —N($R_{10}$)—.

The compounds of Formula 1, 2, or 3 can have $R_{10}$ be hydrogen.

The compounds can have a structure of Formula 4:

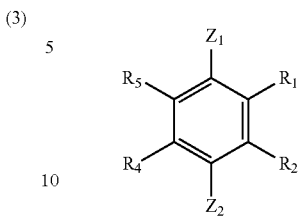
(3)

wherein $R_1$, $R_2$, $R_4$, and $R_5$ are independently hydrogen, alkyl, or alkoxyl; $Z_1$ is has a structure of moiety C

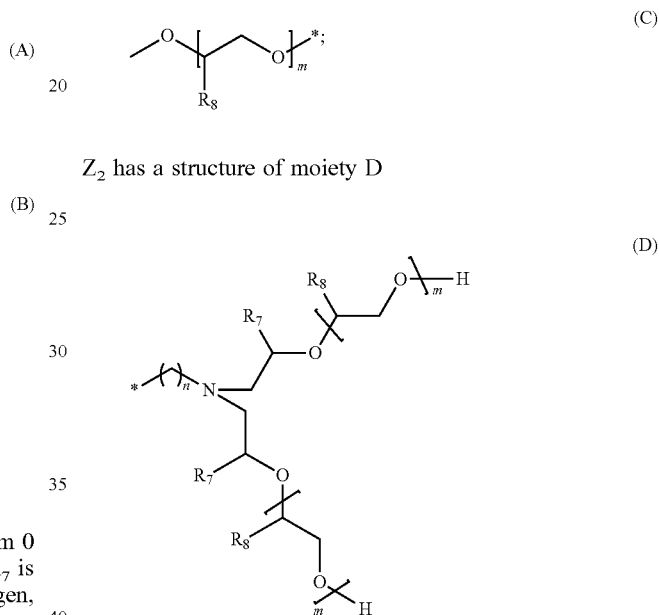

$Z_2$ has a structure of moiety D n is an integer from 0 to 5; $R_7$ is alkyl, or —(CH$_2$)z-O—$R_{11}$, $R_8$ is independently hydrogen, alkyl, or aryl; $R_{11}$ is hydrogen or alkyl; m is an integer from 3 to 30; and z is an integer from 0 to 6.

The compounds having a structure of Formula 4 can have n be 0.

The compounds having a structure of Formula 4 can have $R_7$ be —(CH$_2$)z-O—$R_{11}$, and z be 1.

The compounds having a structure of Formula 4 can have $R_8$ be hydrogen.

The compounds having a structure of Formula 4 can have $R_{11}$ be 2-ethylhexyl.

The compounds having a structure of Formula 4 can have m be an integer from 10 to 30.

Polymer compositions described herein can comprise a water-in-oil emulsion comprising an aqueous phase comprising water and a water-soluble or water-dispersible polymer, and an oil phase comprising an oil and an emulsifying agent; and an inversion surfactant comprising the compound of Formula 1, 2, or 3 described herein.

The polymer compositions described herein can have the water-in-oil emulsion further comprise the inversion surfactant.

The polymer compositions can further comprise an aqueous solution containing the inversion surfactant.

A polymer composition can also comprise a water-soluble or water-dispersible polymer, an oil, a suspending agent, and the inversion surfactant comprising a compound of Formula 1, 2, or 3 described herein.

Disclosed herein are also methods of dissolving the water-soluble or water-dispersible polymer of the polymer compositions disclosed herein. The method comprising contacting the water-in-oil emulsion with the inversion surfactant.

The methods disclosed herein can have the water-in-oil emulsion further comprise the inversion surfactant and the water-in-oil emulsion is contacted with an aqueous solution.

The methods can have the water-in-oil emulsion be contacted with an aqueous solution comprising the inversion surfactant.

The polymer compositions or methods can have the inversion surfactant have a concentration of from about 0.1 wt. % to about 10 wt. % based on the total weight of the emulsion.

The polymer compositions or methods disclosed herein can have the inversion surfactant have a concentration of from about 0.5 wt. % to about 5 wt. % based on the total weight of the emulsion.

The polymer compositions or methods can have the polymer compositions further comprise an ethoxylated $C_{10}$-$C_{16}$ alcohol; a $C_{12}$-$C_{13}$ primary alcohol of linear and monomethyl branched alcohol having on average 9 moles ethylene oxide; an ethoxylate of a saturated $C_{12}$-15 alcohol; an ethoxylated $C_{12}$-14 alcohol; an ethoxylated primary branched saturated $C_{13}$ alcohol; an ethoxylated $C_{10}$ Guerbet alcohol; an ethoxylated saturated iso-$C_{13}$ alcohol; a saturated, predominantly unbranched $C_{13}$-15 oxo alcohol having 11 ethylene oxide groups; a secondary alcohol ethoxylate; a nonionic, alkoxylated alcohol; a polyoxyethylene (9) synthetic primary $C_{13}/C_{15}$ alcohol; an isotridecyl alcohol ethoxylated with an average of 9 moles ethylene oxide; an ethoxylated linear primary $C_{12-14}$ alcohol; an ethoxylated nonylphenol; tert-octylphenoxypoly(ethoxyethanol); a tridecyl ether phosphate; a polyoxyethylene (5) soyaallylamine; a polyethylene glycol (PEG) 400 monooleate; a PEG 600 monooleate; aPEG-25 castor oil; a PEG-30 castor oil; a PEG-40 castor oil; an aliphatic phosphate ester with 10 moles EO; an aliphatic phosphate ester with 6 moles EO; an oleic acid monoethanol amide with 14 moles ethylene oxide; a soyamine ethoxylate; or a combination thereof.

The methods described herein can have the inversion surfactant be activated by contacting the inversion surfactant with an aqueous solution.

The methods disclosed herein can have the inversion surfactant be activated by contacting the inversion surfactant with an inversion aid.

The methods can also have the inversion aid comprise glycol, a polypropylene glycol, polyglycerol, urea, sorbitol, sucrose, glycerol, a polyglycerol, a phosphate, choline chlorine, guanidine, dioctyl-sulfosuccinate, malic acid, lactic acid, N-(phosphonomethyl)glycine, 2-phosphonopropanoic acid, 3-phosphonopropanoic acid, 4-phosphonobutanoic acid, a phosphinosuccinic oligomer, a polyethylene glycol, urea, sorbitol, sucrose, glycerol, a phosphate, choline chlorine, or a combination thereof.

The methods can further have the aqueous solution contain a salt.

The methods can also have the temperature of the aqueous solution be increased from about 2° C. to about 65° C.

Also provided are methods of preparing a compound of Formula 1, 2, or 3 as described herein. The method comprises reacting compound (A) with compound (B) to form compound (C); and further reacting compound (C) with compound (D) to form compound (F)

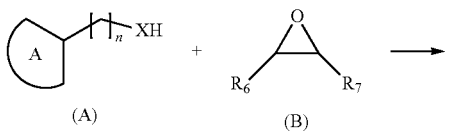

(A)         (B)

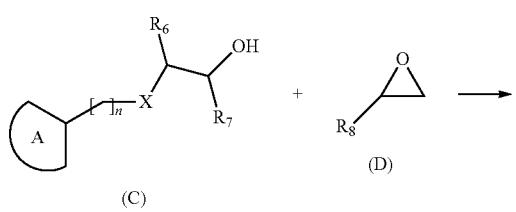

(C)         (D)

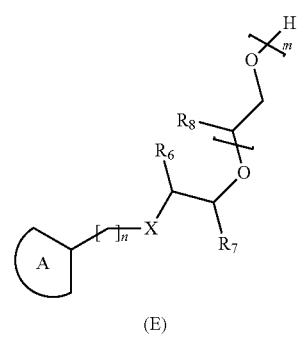

(E)

wherein A, X, $R_6$, $R_7$, $R_8$, $R_9$, n and m are as defined herein.

Still other methods of preparing the compounds described herein comprise reacting compound (F) with R—XH and an acid catalyst to form compound (G); and further reacting compound (G) with compound (D) to form compound (H); or

(F)

(G)

(D)

(H)

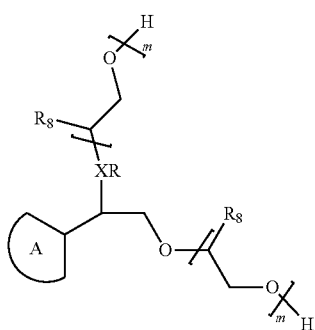

reacting compound (F) with R—XH and a base catalyst to form compound (J); and further reacting compound (J) with compound (D) to form compound (K);

(F)

(J)

(D)

(K)

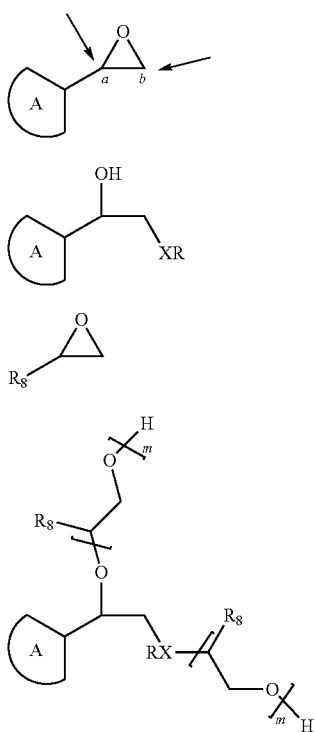

wherein A, X, $R_6$, $R_7$, $R_8$, $R_9$, n and m are as defined in connection with the compounds herein; and R is independently hydrogen or alkyl.

Detergent compositions are also provided. The detergent compositions disclosed herein can comprise a building agent and a surfactant comprising the compound of Formula 1, 2, or 3 described herein.

Cleaning compositions are also provided. The cleaning compositions disclosed herein can comprise the compound of Formula 1, 2, or 3 described herein. Optionally, the cleaning composition can further comprise a building agent.

Disclosed herein are also methods of cleaning an article. The method comprises contacting the article with a detergent composition comprising the compound of Formula 1, 2, or 3 as described herein.

In the methods of cleaning an article, the cleaning composition can further comprise a building agent.

The building agent can comprise an enzyme, an oxidizing agent, a condensed phosphate, an alkali metal carbonate, an alkali metal silicate, an alkali metal metasilicate, a phosphonate, an amino carboxylic acid, a carboxylic acid polymer, or a combination thereof.

The article can be a metal surface, a glass surface, a fabric, a ware, a polycarbonate surface, a polysulfone surface, a melamine surface, a ceramic surface, a porcelain surface, or a combination thereof.

For example, the article can be a fabric or the article can be a ware.

Also disclosed herein are methods of cleaning a membrane. The methods comprise contacting the membrane with a cleaning composition comprising the compound of Formula 1, 2, or 3 as described herein.

The membrane can be a membrane used in a dairy process.

The membrane can be a microfiltration membrane, an ultrafiltration membrane, a nanofiltration membrane, a reverse osmosis membrane, or a combination thereof.

Other objects and features will be in part apparent and in part pointed out hereinafter.

BRIEF DESCRIPTION OF THE SEVERAL VIEWS OF THE DRAWING

Corresponding reference characters indicate corresponding parts throughout the drawings.

DETAILED DESCRIPTION OF THE INVENTION

Figure 1:
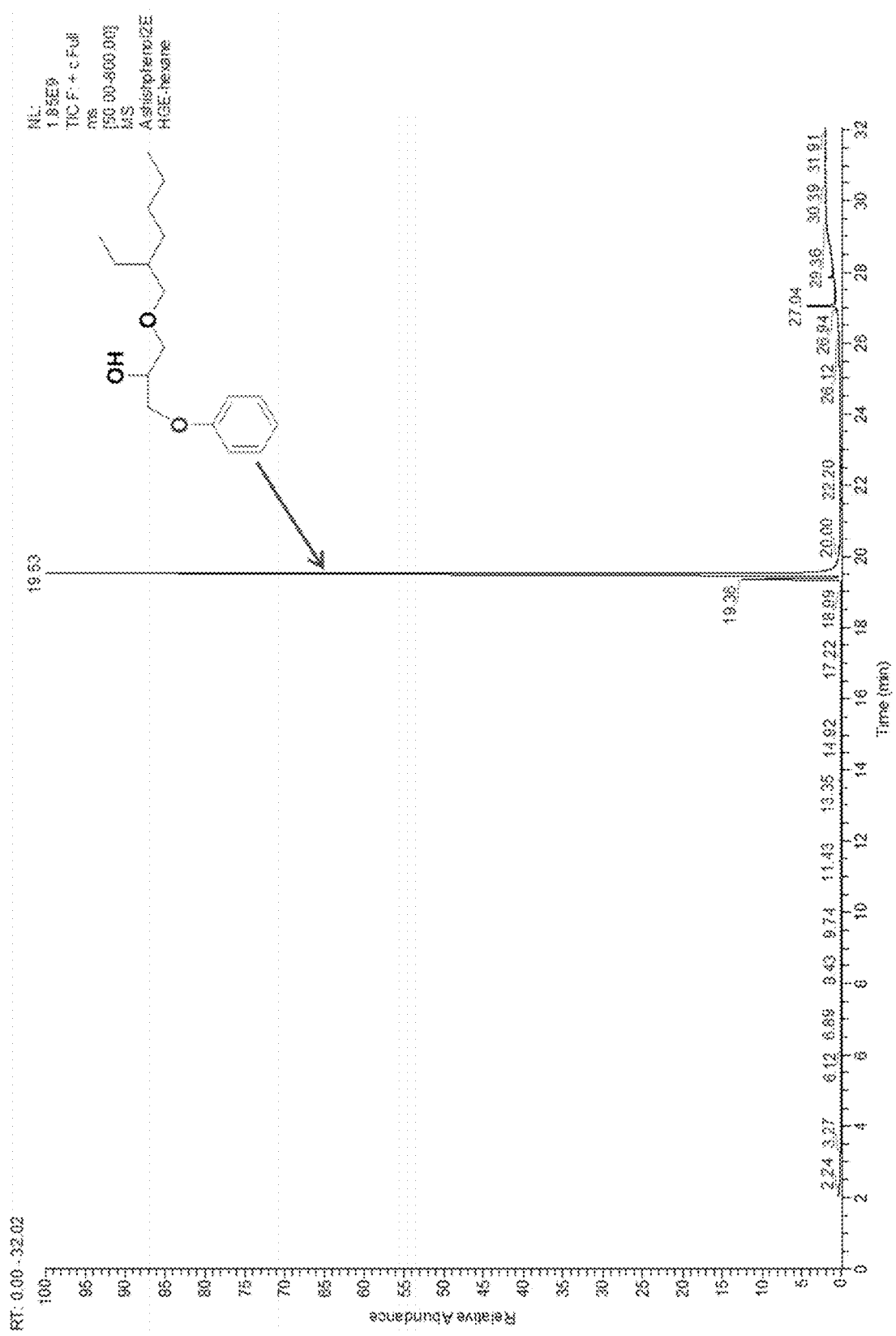
FIG. 1 is a gas chromatography-mass spectra (GC-MS) profile of the reaction mixture of Example 1.

Compounds and compositions are provided that can dissolve water-soluble or water-dispersible polymers rapidly and completely in aqueous solution. The polymer compositions containing the surfactant compounds and compositions described herein can be used in various industries including for water clarification, papermaking, sewage and industrial water treatment, drilling mud stabilizers, and enhanced oil recovery. The compounds and compositions herein can also be used as general surfactants in detergent compositions or in methods of cleaning articles or membranes.

Polymer compositions including water-in-oil emulsions and inversion surfactants are provided. Also, methods of dissolving a water-soluble or water-dispersible polymer are disclosed.

Therefore, polymer compositions and methods using the polymer compositions are described herein. Disclosed herein are compounds and compositions useful as inversion surfactants and to aid in the dissolution of polymers. Also provided are detergent and cleaning compositions comprising the compounds and methods of cleaning articles or membranes. For example, disclosed herein is the compound of Formula 1 having the structure of Formula 1:

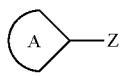

(1)

wherein A is an optionally substituted phenyl, naphthalene, indole, purine, pyridine, quinoline, isoquinoline, pyrimidine, pyrole, furan, thiophene, imidazole, or thiazole; and Z has a structure of moiety A or moiety B:

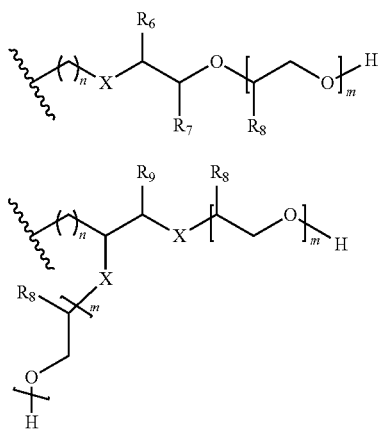

wherein X is —O—, —N($R_{10}$)—, —OC(O)—, —C(O)O—, —N($R_{10}$)C(O)—, —C(O)N($R_{10}$)—, —OC(O)O—, —OC(O)N($R_{10}$)—N($R_{10}$)C(O)O—, or —N($R_{10}$)C(O) N($R_{10}$)—; n is an integer from 0 to 10; $R_6$ and $R_9$ are independently hydrogen, alkyl, or aryl; $R_7$ is alkyl, aryl, or —($CH_2$)z-O—$R_{11}$, $R_8$ is independently hydrogen, alkyl, or aryl; $R_{10}$ is hydrogen, alkyl, or Z; $R_{11}$ is hydrogen or alkyl; m is independently an integer from 3 to 20; and z is an integer from 1 to 10.

The compounds of Formula 1 can have moiety B have the structure of moiety B1 or moiety B2:

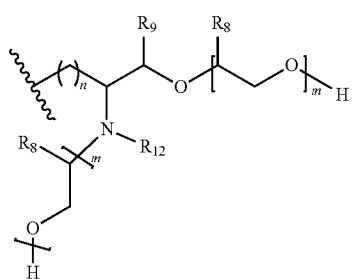

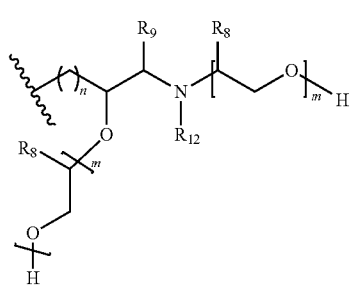

wherein $R_9$ is independently hydrogen, alkyl, or aryl; and $R_{12}$ is independently $C_3$ to $C_{22}$ alkyl or alkenyl.

The compounds of Formula 1 can have A be an optionally substituted phenyl, naphthyl, pyridyl, quinolyl, or isoquinolyl.

The compounds of Formula 1 can have A be an optionally substituted phenyl or naphthyl.

Further, the compounds can have the structure of Formula 2:

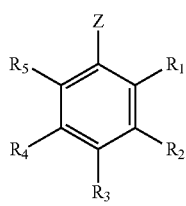

(2)

wherein $R_1$, $R_2$, $R_3$, $R_4$, and $R_5$ are independently hydrogen, Z, alkyl, alkoxyl, or two adjacent R groups combine to form a fused ring; Z has a structure of moiety A or moiety B:

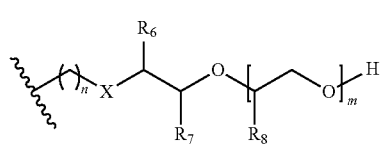

(A)

-continued

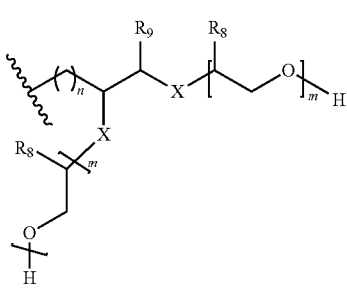
(B)

wherein X
is —O—, —N(R$_{10}$)—, —OC(O)—, —C(O)O—, —N(R$_{10}$)C(O)—, —C(O)N(R$_{10}$)—, —OC(O)O—, —OC(O)N(R$_{10}$)—N(R$_{10}$)C(O)O—, or —N(R$_{10}$)C(O) N(R$_{10}$)—; n is an integer from 0 to 10; R$_6$ and R$_9$ are independently hydrogen, alkyl, or aryl; R$_7$ is alkyl, aryl, or —(CH$_2$)z-O—R$_{11}$, R$_8$ is independently hydrogen, alkyl, or aryl; R$_{10}$ is hydrogen, alkyl, or Z; R$_{11}$ is hydrogen or alkyl; m is an integer from 3 to 20; and z is an integer from 1 to 10.

The compounds of Formula 2 can have moiety B have the structure of moiety B1 or moiety B2:

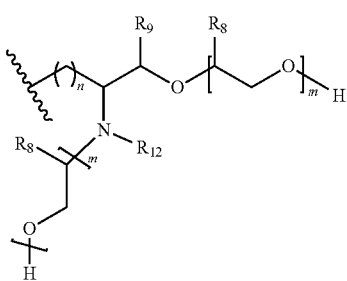
(B1)

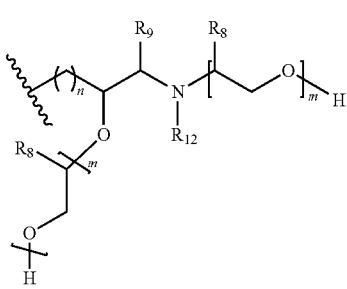
(B2)

wherein R$_9$ is independently hydrogen, alkyl, or aryl; and R$_{12}$ is independently C$_3$ to C$_{22}$ alkyl or alkenyl.

The compounds of Formula 2 can have at least one of R$_1$, R$_2$, R$_3$, R$_4$, and R$_5$ be Z.

The compounds of Formula 2 can have Z have the structure of moiety A, X be —O—; n be 0; R$_1$, R$_2$, R$_3$, R$_4$, R$_5$ be hydrogen; R$_7$ be —(CH$_2$)z-O—R$_{11}$, z be 1, R$_8$ be hydrogen, R$_{11}$ be 2-ethylhexyl, and m be an integer from 7 to 13 or an integer from 7 to 12.

The compounds can have the structure of Formula 3:

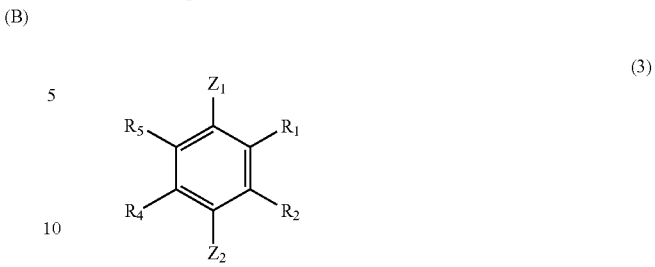
(3)

wherein R$_1$, R$_2$, R$_4$, and R$_5$ are independently hydrogen, alkyl, alkoxyl, or Z; and Z$_1$, Z$_2$, and Z independently have a structure of moiety A or moiety B:

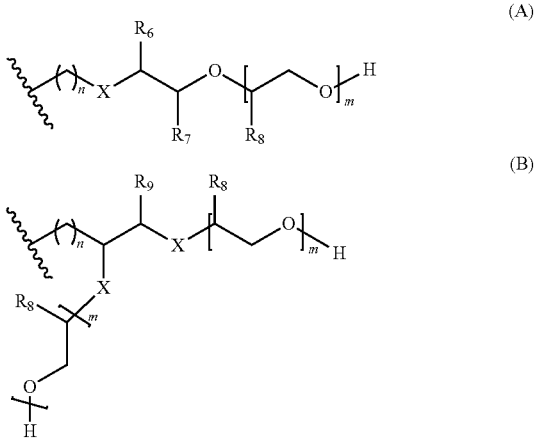
(A)

(B)

wherein X is —O— or —N(R$_{10}$)—; n is an integer from 0 to 5; R$_6$ and R$_9$ are independently hydrogen or alkyl; R$_7$ is alkyl, or —(CH$_2$)z-O—R$_{11}$, R$_8$ is independently hydrogen, alkyl, or aryl; R$_{10}$ is hydrogen, alkyl, or Z; R$_{11}$ is hydrogen or alkyl; m is an integer from 3 to 20; and z is an integer from 1 to 10.

The compounds of Formula 1 or 2 can have R$_1$, R$_2$, R$_3$, R$_4$, and R$_5$ independently be hydrogen or C$_1$ to C$_4$ alkyl.

The compounds of Formula 1 or 2 can have R$_1$, R$_2$, R$_3$, R$_4$, and R$_5$ be hydrogen.

The compounds of Formula 1, 2, or 3 can have R$_6$ and R$_9$ be hydrogen.

The compounds of Formula 1, 2, or 3 can have R$_8$ be hydrogen or methyl.

The compounds Formula 1, 2, or 3 can have R$_7$ be —(CH$_2$)z-O—R$_{11}$.

The compounds of Formula 1, 2, or 3 can have z be 1 to 3.

The compounds of Formula 1, 2, or 3 can have R$_{11}$ be C$_4$ to C$_{22}$ alkyl.

The compounds of Formula 1, 2, or 3 can have X be —O— or —N(R$_{10}$)—.

The compounds of Formula 1, 2, or 3 can have X be —O—.

The compounds of Formula 1, 2, or 3 can have X be —N(R$_{10}$)—.

The compounds of Formula 1, 2, or 3 can have R$_{10}$ be hydrogen.

The compounds can have the structures:

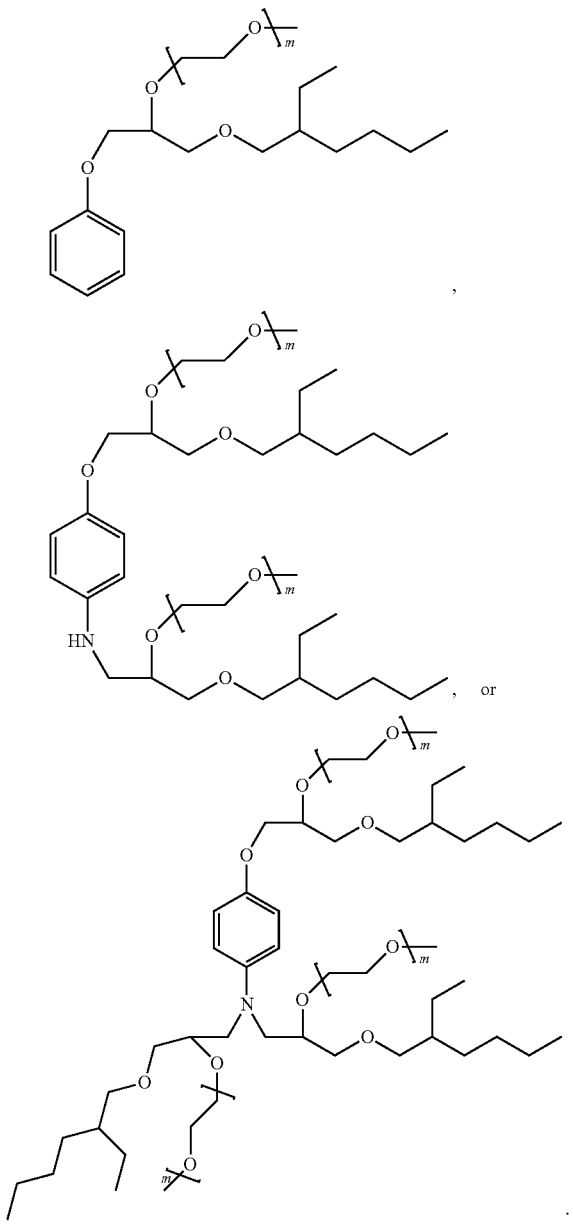

, or

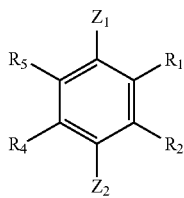

The compounds can also have a structure of Formula 4:

(3)

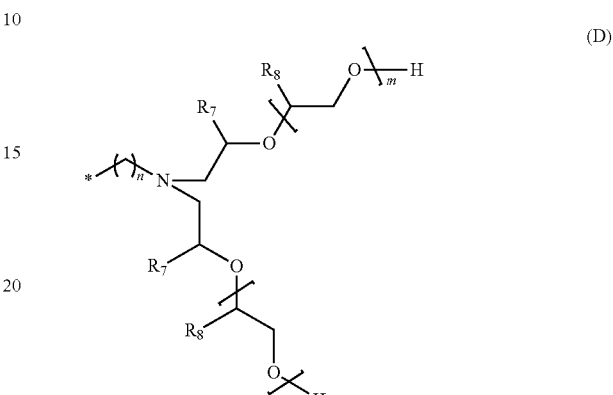

wherein $R_1$, $R_2$, $R_4$, and $R_5$ are independently hydrogen, alkyl, or alkoxyl; $Z_1$ is has a structure of moiety C

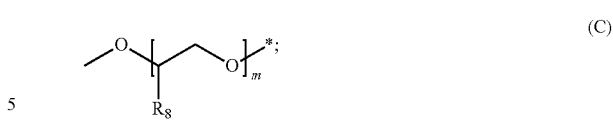

$Z_2$ has a structure of moiety D (D)

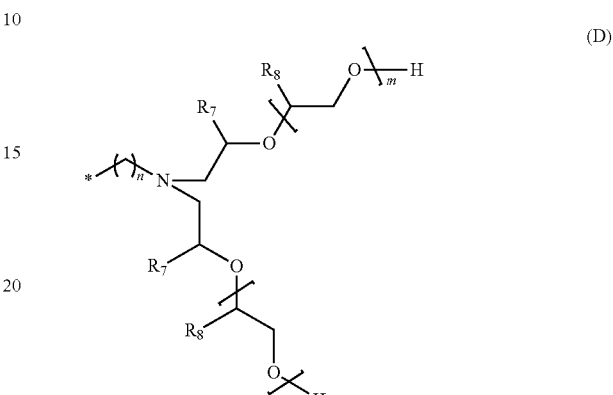

n is an integer from 0 to 5; $R_7$ is alkyl, or $-(CH_2)z-O-R_{11}$, $R_8$ is independently hydrogen, alkyl, or aryl; $R_{11}$ is hydrogen or alkyl; m is an integer from 3 to 30; and z is an integer from 0 to 6.

The compounds having a structure of Formula 4 can have n be 0.

The compounds having a structure of Formula 4 can have $R_7$ be $-(CH_2)z-O-R_{11}$, and z be 1.

The compounds having a structure of Formula 4 can have $R_8$ be hydrogen.

The compounds having a structure of Formula 4 can have $R_{11}$ be 2-ethylhexyl.

The compounds having a structure of Formula 4 can have m be an integer from 10 to 30.

The compounds having a structure of Formula 4 can have $R_1$, $R_2$, $R_4$, and $R_5$ be hydrogen or methyl; preferably, $R_1$, $R_2$, $R_4$, and $R_5$ are hydrogen.

The compounds of Formula 4 can have the following structure

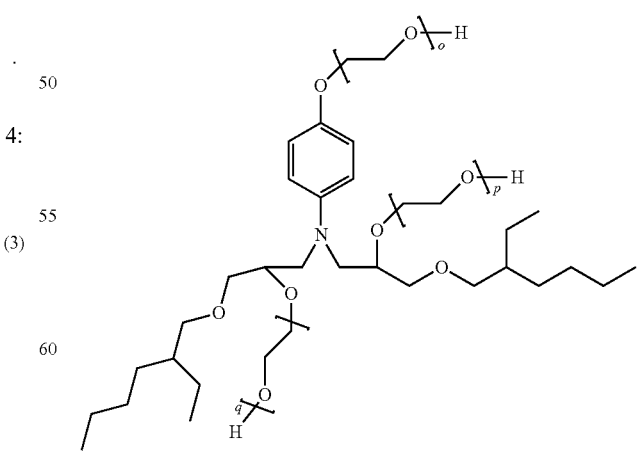

wherein o, p, and q are integers and sum of o, p and q is 10, 12, 14, 16, 18, 20, 22, or 24.

Polymer compositions described herein can comprise a water-in-oil emulsion comprising an aqueous phase comprising water and a water-soluble or water-dispersible polymer, and an oil phase comprising an oil and an emulsifying agent; and an inversion surfactant comprising the compound of Formula 1, 2, 3, or 4 described herein.

The polymer compositions described herein can have the water-in-oil emulsion further comprise the inversion surfactant.

The polymer compositions can further comprise an aqueous solution containing the inversion surfactant.

A polymer composition can also comprise a water-soluble or water-dispersible polymer, an oil, a suspending agent, and the inversion surfactant comprising a compound of Formula 1, 2, 3, or 4 described herein.

Disclosed herein are also methods of dissolving the water-soluble or water-dispersible polymer of the polymer compositions disclosed herein. The method comprising contacting the water-in-oil emulsion with the inversion surfactant.

The methods disclosed herein can have the water-in-oil emulsion further comprise the inversion surfactant and the water-in-oil emulsion is contacted with an aqueous solution.

The methods can have the water-in-oil emulsion be contacted with an aqueous solution comprising the inversion surfactant.

The polymer compositions or methods can have the inversion surfactant have a concentration of from about 0.1 wt. % to about 10 wt. % based on the total weight of the emulsion.

The polymer compositions or methods disclosed herein can have the inversion surfactant have a concentration of from about 0.5 wt. % to about 5 wt. % based on the total weight of the emulsion.

The polymer compositions or methods can have the polymer compositions further comprise an ethoxylated $C_{10}$-$C_{16}$ alcohol; a $C_{12}$-$C_{13}$ primary alcohol of linear and monomethyl branched alcohol having on average 9 moles ethylene oxide; an ethoxylate of a saturated $C_{12}$-15 alcohol; an ethoxylated $C_{12}$-14 alcohol; an ethoxylated primary branched saturated $C_{13}$ alcohol; an ethoxylated $C_{10}$ Guerbet alcohol; an ethoxylated saturated iso-$C_{13}$ alcohol; a saturated, predominantly unbranched $C_{13}$-15 oxo alcohol having 11 ethylene oxide groups; a secondary alcohol ethoxylate; a nonionic, alkoxylated alcohol; a polyoxyethylene (9) synthetic primary $C_{13}/C_{15}$ alcohol; an isotridecyl alcohol ethoxylated with an average of 9 moles ethylene oxide; an ethoxylated linear primary $C_{12}$-14 alcohol; an ethoxylated nonylphenol; tert-octylphenoxypoly(ethoxyethanol); a tridecyl ether phosphate; a polyoxyethylene (5) soyaallylamine; a polyethylene glycol (PEG) 400 monooleate; a PEG 600 monooleate; aPEG-25 castor oil; a PEG-30 castor oil; a PEG-40 castor oil; an aliphatic phosphate ester with 10 moles EO; an aliphatic phosphate ester with 6 moles EO; an oleic acid monoethanol amide with 14 moles ethylene oxide; a soyamine ethoxylate; or a combination thereof.

The methods described herein can have the inversion surfactant be activated by contacting the inversion surfactant with an aqueous solution.

The methods disclosed herein can have the inversion surfactant be activated by contacting the inversion surfactant with an inversion aid.

The methods can also have the inversion aid comprise glycol, a polypropylene glycol, polyglycerol, urea, sorbitol, sucrose, glycerol, a polyglycerol, a phosphate, choline chlorine, guanidine, dioctyl-sulfosuccinate, malic acid, lactic acid, N-(phosphonomethyl)glycine, 2-phosphonopropanoic acid, 3-phosphonopropanoic acid, 4-phosphonobutanoic acid, a phosphinosuccinic oligomer, a polyethylene glycol, urea, sorbitol, sucrose, glycerol, a phosphate, choline chlorine, or a combination thereof.

The methods can further have the aqueous solution contain a salt.

The methods can also have the temperature of the aqueous solution be increased from about 2° C. to about 65° C.

The polymer composition can comprise from about 5 wt. % to about 70 wt. %, from about 10 wt. % to about 70 wt. %, from about 20 wt. % to about 70 wt. %, from about 30 wt. % to about 70 wt. %, from about 40 wt. % to about 70 wt. %, from about 50 wt. % to about 70 wt. %, from about 60 wt. % to about 70 wt. %, from about 10 wt. % to about 60 wt. %, from about 10 wt. % to about 50 wt. %, from about 15 wt. % to about 70 wt. %, from about 15 wt. % to about 65 wt. %, from about 18 wt. % to about 65 wt. %, from about 20 wt. % to about 60 wt. %, from about 20 wt. % to about 50 wt. %, from about 25 wt. % to about 70 wt. %, from about 25 wt. % to about 60 wt. %, from about 25 wt. % to about 50 wt. %, of the water-soluble or water-dispersible polymer. Preferably, the polymer composition comprises from about 18 wt. % to about 65 wt. % of the water-soluble or water-dispersible polymer.

The polymer composition can be a slurry comprising a water-soluble polymer suspended in an oil-based vehicle with a suspension agent and an inversion surfactant comprising a compound of Formula 1, 2, or 3.

Specifically, the oil-based vehicle can be petroleum distillate. Petroleum distillates are products distilled from petroleum crude oil and use different CAS #identifiers depending upon the molecular weight distribution and processing technology used. A petroleum distillate suitable for the present composition can be, for example, CAS #64742-47-8.

The suspension aid can be a variation of diblock copolymers based on styrene and ethylene/propylene. The composition can also contain a dispersant such as organophilic clay or a synthetic alternative as the suspension agent.

The inversion surfactant comprising a compound having the structure of Formula 1, 2, or 3 can be blended with one or more additional inversion surfactants. For example, the additional inversion surfactants of interest having HLBs from about 9 to about 15 include those listed in the following table and combinations thereof.

| Trade Name | Chemistry |
| --- | --- |
| Alfonic 1412-7 | Ethoxylated $C_{10}$-$C_{16}$ alcohols |
| Novel 23E9 | $C_{12}$-$C_{13}$ primary alcohol of linear and mono-methyl branched alcohols having on average 9 moles EO |
| Synperonic A11 | Ethoxylate of a saturated $C_{12-15}$ alcohol |
| Surfonic 1412-12 | Ethoxylated $C_{12-14}$ alcohol |
| Synperonic 13/7 | Ethoxylated primary branched saturated $C_{13}$ alcohol |
| Lutensol TO10 | Ethoxylated $C_{10}$ Guerbet alcohol |
| Lutensol TO12 | Ethoxylated saturated iso-$C_{13}$ alcohol |
| Lutensol AO11 | Saturated, predominantly unbranched $C_{13-15}$ oxo alcohols having 11 EO groups |
| Tergitol 15-S-9 | Secondary Alcohol Ethoxylate |
| Tergitol 15-S-12 | Secondary Alcohol Ethoxylate |
| Plurafac RA 20 | Nonionic, alkoxylated alcohol |
| Plurafac RA 30 | Nonionic, alkoxylated alcohol |
| Synperonic A9 | Polyoxyethylene (9) synthetic primary $C_{13}/C_{15}$ alcohol |
| Alfonic TDA9 | Isotridecyl alcohol ethoxylated with an average of 9 moles EO |

| Trade Name | Chemistry |
|---|---|
| Novel 1412-11 | Ethoxylated linear primary $C_{12-14}$ alcohol |
| Tergitol NP-9.5 | Ethoxylated nonylphenol |
| Tergitol NP-10.5 | Ethoxylated nonylphenol |
| Triton X-114 | tert-octylphenoxypoly(ethoxyethanol) |
| Rhodafac RS-410 | Tridecyl ether phosphate |
| Ethomeen S/15 | Polyoxyethylene (5) soyaallylamines |
| Ethox MO-9 | PEG 400 monooleate |
| Ethox MO-14 | PEG 600 monooleate |
| Ethox CO-25 | PEG-25 Castor oil |
| Alkamul EL-620 | PEG-30 Castor oil |
| Ethox CO-40 | PEG-40 Castor oil |
| Rhodafac RS-710 | Aliphatic phosphate ester, 10 moles EO |
| Rhodafac RS-610 | Aliphatic phosphate ester, 6 moles EO |
| Serdox NXC-14 | Oleic acid monoethanol amide + 14 EO |
| Ethomeen S/25 | Soyamine ethoxylate |

The inversion surfactant comprising a compound having the structure of Formula 1, 2, or 3 can be blended with an ethoxylated $C_{10}$-$C_{16}$ alcohol; a $C_{12}$-$C_{13}$ primary alcohol of linear and mono-methyl branched alcohol having on average 9 moles ethylene oxide; an ethoxylate of a saturated $C_{12}$-15 alcohol; an ethoxylated $C_{12}$-14 alcohol; an ethoxylated primary branched saturated $C_{13}$ alcohol; an ethoxylated $C_{10}$ Guerbet alcohol; an ethoxylated saturated iso-$C_{13}$ alcohol; a saturated, predominantly unbranched $C_{13}$-15 oxo alcohol having 11 ethylene oxide groups; a secondary alcohol ethoxylate; a nonionic, alkoxylated alcohol; a polyoxyethylene (9) synthetic primary $C_{13}$/$C_{15}$ alcohol; an isotridecyl alcohol ethoxylated with an average of 9 moles ethylene oxide; an ethoxylated linear primary $C_{12-14}$ alcohol; an ethoxylated nonylphenol; tert-octylphenoxypoly(ethoxyethanol); a tridecyl ether phosphate; a polyoxyethylene (5) soyaallylamine; a polyethylene glycol (PEG) 400 monooleate; a PEG 600 monooleate; aPEG-25 castor oil; a PEG-30 castor oil; a PEG-40 castor oil; an aliphatic phosphate ester with 10 moles EO; an aliphatic phosphate ester with 6 moles EO; an oleic acid monoethanol amide with 14 moles ethylene oxide; a soyamine ethoxylate; or a combination thereof.

Also disclosed are methods of preparing a compound described herein, the method comprising reacting compound (A) with compound (B) to form compound (C); and further reacting compound (C) with compound (D) to form compound (E)

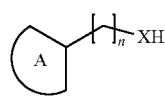

(A)

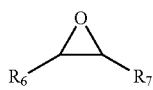

(B)

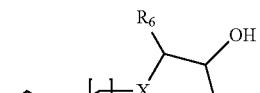

(C)

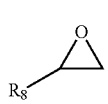

(D)

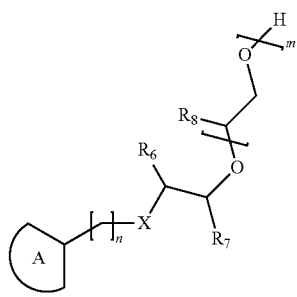

(E)

wherein A, X, $R_6$, $R_7$, $R_8$, $R_9$, n and m are as defined in connection with the compounds herein above.

Another method of preparing a compound described herein comprises reacting compound (F) with R—XH and an acid catalyst to form compound (G); and further reacting compound (G) with compound (D) to form compound (H); or

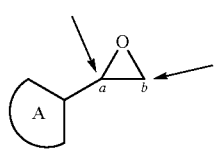

(F)

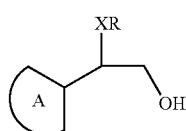

(G)

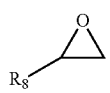

(D)

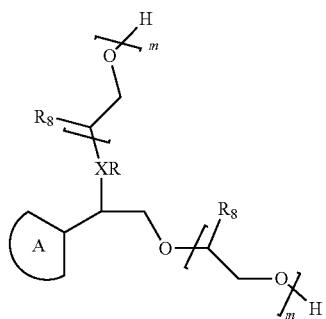

(H)

reacting compound (F) with R—XH and a base catalyst to form compound (J); and further reacting compound (J) with compound (D) to form compound (K);

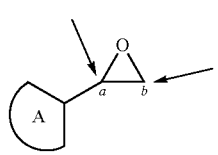

(F)

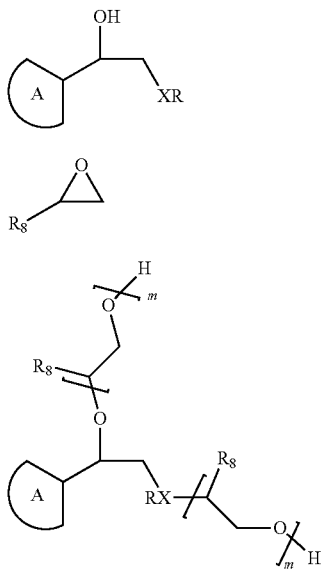

wherein A, X, $R_6$, $R_7$, $R_8$, $R_9$, n and m are as defined in connection with the compounds herein; and R is independently hydrogen or alkyl.

The compounds having the structure of Formula 1, 2, or 3 can be prepared by the following synthetic schemes:

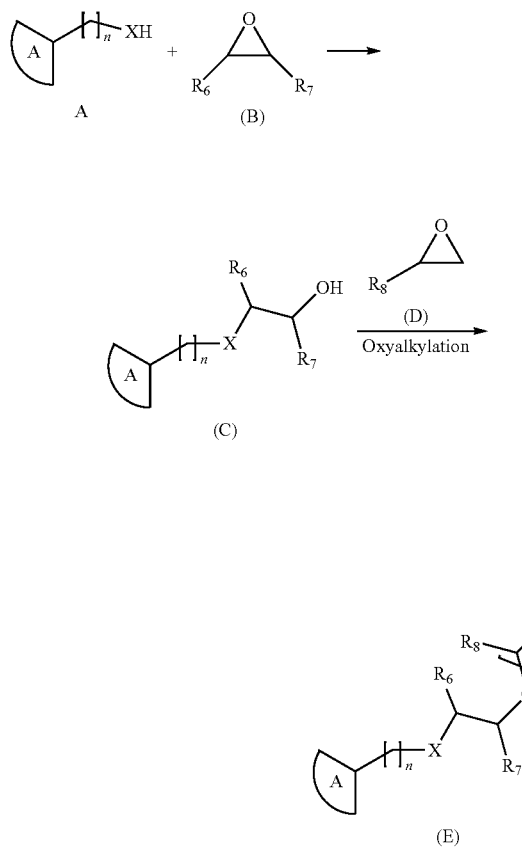

wherein A, X, $R_6$, $R_7$, $R_8$, m, and n are defined as above.

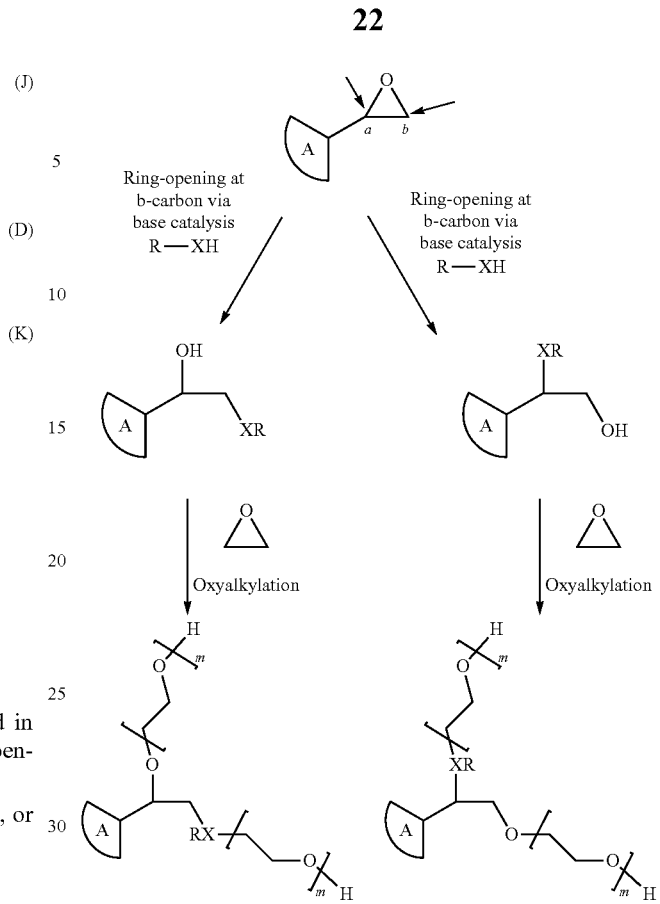

wherein A, X, m, and n are defined as above, and R is independently hydrogen or alkyl.

In the described polymer composition, the inversion surfactant comprising a compound having the structure of Formula 1, 2, or 3 can have a concentration of from about 0.1 wt. % to about 10 wt. % based on the total weight of the polymer composition. Preferably, the inversion surfactant comprising a compound having the structure of Formula 1, 2, or 3 has a concentration of from about 0.5 wt. % to about 5 wt. % based on the total weight of the polymer composition.

The water-in-oil polymer emulsion can further comprise an emulsifying agent. The surfactant or blend of surfactants can have a low hydrophile-lipophile balance (HLB) to aid preparation of an oil-continuous emulsion. Appropriate surfactants for water-in-oil emulsion polymerizations which are commercially available are compiled in the North American Edition of McCutcheon's Emulsifiers & Detergents. For example, the emulsifying agent can comprise nonionic ethoxylated fatty acid esters, ethoxylated sorbitan fatty acid esters, sorbitan esters of fatty acids such as sorbitan monolaurate, sorbitan monostearate, and sorbitan monooleate, block copolymers of ethylene oxide and hydroxyacids having a $C_{10}$-$C_{30}$ linear or branched hydrocarbon chain, linear or branched alcohol alkoxylates, or a combination thereof.

The emulsifying agent can be a single nonionic surfactant or blend thereof having a combined HLB value of about 2 to 10, for example about 3 to 10, or about 4 to 10, or about 5 to 10, or about 6 to 10, or about 7 to 10, or about 8 to 10, or about 2 to 9, or about 2 to 8, or about 2 to 7, or about 2 to 6, or about 2 to 5, or about 3 to 9, or about 4 to 8.

The water-in-oil emulsion can also comprise an alcohol alkoxylate. The alcohol alkoxylate can comprise a linear or branched alcohol ethoxylate, or a combination thereof.

The surfactant compositions, as described above, are useful as inverters (activators) of water-in-oil (inverse) emulsion polymers in various industries including for water clarification, papermaking, sewage and industrial water treatment, drilling mud stabilizers, and enhanced oil recovery.

The water-soluble or water-dispersible polymers useful in the polymer compositions include various polymers and their mixtures, or derivatives. The water-soluble or water-dispersible polymers used can be an anionic, a cationic, a nonionic, a zwitterionic, or an amphoteric polymer.

For example, the water-soluble or water-dispersible polymers contained in the polymer compositions can comprise polyacrylamides, polyacrylates, copolymers thereof, and hydrophobically modified derivatives of these polymers.

Further, the water-soluble or water-dispersible polymers used in the polymer compositions described herein can include the water-soluble or water-dispersible polymers described in U.S. Pat. Nos. 3,624,019 and 3,734,873; the water-soluble or water-dispersible polymers can have various architectures as disclosed in EP 202780 (linear and cross-linked), and EP 374458, U.S. Pat. Nos. 5,945,494 and 5,961,840 (branched). Additionally, the water-soluble or water-dispersible polymers can contain hydrophobic monomers as disclosed in U.S. Pat. No. 4,918,123. These references are herein incorporated by reference for their various disclosures of water-soluble and water-dispersible polymers.

The polymers usefully incorporated in the polymer compositions typically have a weight average molecular weight (MW) of about 500,000 Daltons to about 100,000,000 Daltons, or about 1,000,000 Daltons to about 50,000,000 Daltons, or about 5,000,000 Daltons to about 30,000,000 Daltons.

The water-soluble or water-dispersible polymer can comprise about 1 mol % to about 100 mol % acrylamide monomers, or about 1 mol % to about 90 mol %, or about 1 mol % to about 80 mol %, or about 1 mol % to about 70 mol %, or about 1 mol % to about 60 mol %, or about 1 mol % to about 50 mol %, or about 1 mol % to about 40 mol %, or about 1 mol % to about 30 mol %, or about 1 mol % to about 20 mol %, or about 1 mol % to about 10 mol %, or about 10 mol % to about 100 mol %, or about 20 mol % to about 100 mol %, or about 30 mol % to about 100 mol %, or about 40 mol % to about 100 mol %, or about 50 mol % to about 100 mol %, or about 60 mol % to about 100 mol %, or about 70 mol % to about 100 mol %, or about 80 mol % to about 100 mol %, or about 90 mol % to about 100 mol %, or about 20 mol % to about 80 mol, or about 30 mol % to about 70 mol %, or about 40 mol % to about 60 mol %, or about 60 mol % to about 80 mol % acrylamide monomers.

The water-soluble polymer or water-dispersible polymer can be present within the water-in-oil emulsion at about 15 wt % to 70 wt %, or about 17 wt % to 70 wt %, or about 19 wt % to 70 wt %, or about 21 wt % to 70 wt %, or about 23 wt % to 70 wt %, or about 25 wt % to 70 wt %, or about 15 wt % to 68 wt %, or about 15 wt % to 66 wt %, or about 15 wt % to 64 wt %, or about 15 wt % to 62 wt %, or about 15 wt % to 60 wt %, or about 15 wt % to 58 wt %, or about 15 wt % to 56 wt %, or about 25 wt % to 65 wt %, or about 30 wt % to 60 wt %, or about 30 wt % to 60 wt % based on the total weight of the emulsion.

Inverse emulsion polymers are prepared by dissolving the required monomers in the water phase, dissolving the emulsifying agent in the oil phase, emulsifying the water phase in the oil phase to prepare a water-in-oil emulsion, homogenizing the water-in-oil emulsion and polymerizing the monomers to obtain the polymer. A self-inverting surfactant may be added to the water-soluble polymer dispersed within the hydrocarbon matrix to obtain a self-inverting water-in-oil emulsion. Alternatively, a polymer solution can be made-up by inverting the polymer dispersed in oil in to water containing the surfactant.

Also present in the water-in-oil emulsion is an amount of water sufficient to form an aqueous (i.e. water) phase within the emulsion. Water is present in the water-in-oil emulsion at about 3 wt % to 50 wt %, or about 5 wt % to 50 wt %, or about 10 wt % to 50 wt %, or about 15 wt % to 50 wt %, or about 20 wt % to 50 wt %, or about 25 wt % to 50 wt %, or about 3 wt % to 35 wt %, or about 3 wt % to 30 wt %, or about 3 wt % to 25 wt %, or about 5 wt % to 45 wt %, or about 5 wt % to 40 wt %, or about 5 wt % to 35 wt %, based on the total weight of the water-in-oil emulsion.

The water-in-oil emulsion also contains an amount of oil sufficient to form an oil phase within the water-in-oil emulsion.

The oil in the oil phase can be a mixture of compounds, wherein the mixture is less than 0.1 wt % soluble in water at 25° C. and is a liquid over the range of 20° C. to 90° C.

The oil in the oil phase can comprise a linear, branched, or cyclic hydrocarbon moieties, aryl or alkaryl moieties, or combinations thereof.

The oil in the oil phase can have a density of about 0.8 g/L to 1.0 g/L, for example about 0.8 g/L to 0.9 g/L.

Examples of suitable oils for the oil phase can include a petroleum distillate, decane, dodecane, isotridecane, cyclohexane, toluene, xylene, and mixed paraffin solvents such as those sold under the trade name ISOPAR® by ExxonMobil Corp. of Irving, Tex.

The oil phase is present in the water-in-oil emulsion at about 10 wt % to 40 wt %, or about 15 wt % to 40 wt %, or about 20 wt % to 40 wt %, or about 22 wt % to 40 wt %, or about 24 wt % to 40 wt %, or about 26 wt % to 40 wt %, or about 28 wt % to 40 wt %, or about 30 wt % to 40 wt %, or about 10 wt % to 38 wt %, or about 10 wt % to 36 wt %, or about 10 wt % to 34 wt %, or about 10 wt % to 32 wt %, or about 10 wt % to 30 wt %, or about 10 wt % to 25 wt %, or about 10 wt % to 20 wt %, or about 15 wt % to 35 wt %, or about 20 wt % to 30 wt % based on the total weight of the water-in-oil emulsion.

The inversion surfactant comprising compounds of Formula 1, 2, or 3 aids the inversion of the water-in-oil emulsion compared to a water-in-oil emulsion comprising no inversion surfactant or compared to a water-in-oil emulsion comprising a comparator inversion surfactant. The inversion surfactant comprising a compound of Formula 1, 2, or 3 increases the speed and/or percent completion of the inversion process compared to a water-in-oil emulsion comprising no inversion surfactant or compared to a water-in-oil emulsion comprising a comparator inversion surfactant.

To aid inversion of a water-in-oil emulsion, the inversion surfactant comprising a compound of Formula 1, 2, or 3 is added to the emulsion at about 0.1 wt % to 20.0 wt % based on the total weight of the emulsion, or about 0.1 wt % to 15.0 wt %, or about 0.1 wt % to 10.0 wt %, or about 0.1 wt % to 7.5 wt %, or about 0.1 wt % to 5.0 wt %, or about 0.5 wt % to 4.5 wt %, or about 1.0 wt % to 4.0 wt %, or about 1.5 wt % to 3.5 wt %, or about 2.0 wt % to 3.0 wt %, or about 0.1 wt % to 4.5 wt %, or about 0.1 wt % to 4.0 wt %, or about 0.1 wt % to 3.5 wt %, or about 0.1 wt % to 3.0 wt %, or about 0.5 wt % to 5.0 wt %, or about 1.0 wt % to 5.0 wt %, or about 1.5 wt % to 5.0 wt %, or about 2.0 wt % to 5.0 wt %, based on the total weight of the emulsion.

The inversion surfactant can be added to the aqueous solution contacted with the emulsion to activate the polymer in a concentration of about 0.1 wt % to 20.0 wt % based on the total weight of the aqueous solution, or about 0.1 wt % to 15.0 wt %, or about 0.1 wt % to 10.0 wt %, or about 0.1 wt % to 7.5 wt %, or about 0.1 wt % to 5.0 wt %, or about 0.5 wt % to 4.5 wt %, or about 1.0 wt % to 4.0 wt %, or about 1.5 wt % to 3.5 wt %, or about 2.0 wt % to 3.0 wt %, or about 0.1 wt % to 4.5 wt %, or about 0.1 wt % to 4.0 wt %, or about 0.1 wt % to 3.5 wt %, or about 0.1 wt % to 3.0 wt %, or about 0.5 wt % to 5.0 wt %, or about 1.0 wt % to 5.0 wt %, or about 1.5 wt % to 5.0 wt %, or about 2.0 wt % to 5.0 wt %, based on the total weight of the aqueous solution.

The effective amount of the polymer composition can be from about 1 ppm to about 10000 ppm, from about 1 ppm to about 9000 ppm, from about 1 ppm to about 8000 ppm, from about 1 ppm to about 7000 ppm, from about 1 ppm to about 6000 ppm, from about 1 ppm to about 5000 ppm, from about 1 ppm to about 4000 ppm, from about 1 ppm to about 3000 ppm, from about 1 ppm to about 2000 ppm, from about 1 ppm to about 1000 ppm, based on the total weight of the process fluid. Preferably, the effective amount of the polymer composition is from about 1 ppm to about 900 ppm, from about 1 ppm, to about 800 ppm, from about 1 ppm to about 700 ppm, from about 1 ppm to about 600 ppm, or from about 1 ppm to about 500 ppm. Further, the effective amount of the polymer composition can be from about 1 ppm to about 250 ppm, from about 1 ppm to about 200 ppm, from about 1 ppm to about 100 ppm, from about 1 ppm to about 75 ppm, from about 1 ppm to about 50 ppm, from about 1 ppm to about 25 ppm, from about 1 ppm to about 15 ppm, or from about 1 ppm to about 10 ppm, based on the total weight of the process fluid.

The inversion and dilution to a target concentration of less than 1 wt % can be accomplished in about 1 to 15 minutes, for example about 1 to 14, 1 to 13, 1 to 12, 1 to 11, 1 to 10, 1 to 9, 1 to 8, 1 to 7, 1 to 6, 1 to 5, 2 to 15, 3 to 15, 4 to 15, 5 to 15, 6 to 15, 7 to 15, 8 to 15, 9 to 15, 10 to 15, 2 to 10, 2 to 9, 2 to 8, 2 to 7, 2 to 6, or 2 to 5 minutes.

After inversion, the aqueous solutions can comprise about 100 ppm to 10,000 ppm (0.01 wt % to 1.00 wt %) water-soluble or water-dispersible polymer, or about 200 ppm to 5000 ppm, or about 200 ppm to 4000 ppm, or about 200 ppm to 3000 ppm, or about 200 ppm to 2500 ppm water-soluble or water-dispersible polymer, based on the total weight of the aqueous solution.

Compositions

The compounds described herein are also useful as general surfactants, e.g., for use in detergents or cleaning solutions.

Exemplary cleaning or detergent compositions include, but are not limited to dishwashing detergents, rinse aids, floor cleaners, presoaks, manual cleaners, degreasers, hard surface cleaners, laundry detergents, sanitizers, disinfectants, food and beverage equipment cleaners, and dairy cleaners. Cleaning compositions and detergent compositions comprising a compound of formula 1, 2 or 3, as described herein, are provided. These compositions can be used for a variety of cleaning applications as described above, but are particularly useful as detergents or membrane cleaners.

The cleaning and/or detergent compositions described herein may comprise a compound of formula 1, 2, or 3 as described herein and at least one of a builder, a chelating agent, a scale inhibitor, a surfactant or any combination thereof.

The detergent and/or cleaning compositions can comprise from about 0.001 to about 99 wt. %, of the compound of Formula 1, 2, or 3, based on the total weight of the detergent and/or cleaning composition as described herein.

Building Agents

Therefore, a cleaning composition or a detergent composition is provided comprising a building agent and a compound of Formula 1, 2, or 3 as described herein.

The detergent composition or cleaning composition can comprise from about 0.1 to about 90 wt. %, of the building agent, based on the total weight of the detergent composition or the cleaning composition.

Examples of suitable building agents include, but are not limited to alkali metal carbonates, alkali metal hydroxides, and alkali metal silicates. Exemplary alkali metal carbonates that can be used include, but are not limited to: sodium or potassium carbonate, bicarbonate, sesquicarbonate, and mixtures thereof. Exemplary alkali metal hydroxides that can be used include, but are not limited to: sodium or potassium hydroxide. The alkali metal hydroxide may be added to the composition in any form known in the art, including as solid beads, dissolved in an aqueous solution, or a combination thereof. Examples of alkali metal silicates include, but are not limited to sodium or potassium silicate or polysilicate, sodium or potassium metasilicate and hydrated sodium or potassium metasilicate or a combination thereof.

The building agent can comprise an alkaline detergent builder. For example, the building agent can comprise an enzyme, an oxidizing agent, a condensed phosphate, an alkali metal carbonate, an alkali metal silicate, an alkali metal metasilicate, a phosphonate, an amino carboxylic acid, a carboxylic acid polymer, or a combination thereof. The detergent composition or cleaning composition can further comprise chelants, surfactants, enzymes, or other components as described herein below.

Chelants

The cleaning composition or detergent composition disclosed herein may also comprise a chelant. Chelants include, but are not limited to, chelating agents (chelators), sequestering agents (sequestrants), and the like. Examples of chelants include, but are not limited to, phosphonates, phosphates, aminocarboxylates and their derivatives, pyrophosphates, polyphosphates, ethylenediamine and ethylenetriamine derivatives, hydroxyacids, and mono-, di-, and tri-carboxylates and their corresponding acids. Other exemplary chelants include aluminosilicates, nitroloacetates and their derivatives, and mixtures thereof.

Suitable aminocarboxylic acids according to the invention include, but are not limited to, methylglycinediacetic acid (MGDA), glutamic acid-N,N-diacetic acid (GLDA), N-hydroxyethylaminodiacetic acid, ethylenediaminetetraacetic acid (EDTA) (including tetra sodium EDTA), hydroxyethylenediaminetetraacetic acid, diethylenetriaminepentaacetic acid, N-hydroxyethyl-ethylenediaminetriacetic acid (HEDTA), diethylenetriaminepentaacetic acid (DTPA), ethylenediaminesuccinic acid (EDDS), 2-hydroxyethyliminodiacetic acid (HEIDA), iminodisuccinic acid (IDS), 3-hydroxy-2-2'-iminodisuccinic acid (HIDS) and other similar acids or salts thereof having an amino group with a carboxylic acid substituent. Additional description of suitable aminocarboxylates suitable for use as chelating agents and/or sequestrants is set forth in Kirk-Othmer, Encyclopedia of Chemical Technology, Third Edition, volume 5, pages 339-366 and volume 23, pages 319-320, the disclosure of which is incorporated by reference herein.

Chelants can be water soluble, and/or biodegradable. Other exemplary chelants include TKPP (tetrapotassium pyrophosphate), PAA (polyacrylic acid) and its salts, phosphonobutane carboxylic acid, Alanine,N,N-bis(carboxymethyl)-,trisodium salt, and sodium gluconate.

The chelant can be free of phosphorus. The chelant may also serve as a solidifying agent to help form the solid composition, such as sodium salts of citric acid.

Preferably, the chelant is a sodium salt of aminocarboxylates. More preferably, the chelant is methyl glycine diacetic acid (MGDA).

Alternatively, the cleaning composition or detergent composition disclosed herein can be free of a chelant, detergent builder, or both. Alternatively, the cleaning composition or detergent composition disclosed herein can be free of a chelant, detergent builder, or both that contain phosphorus.

Scale Inhibitors

The cleaning composition or detergent composition can further comprise one or more scale inhibitors. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), mono-, bis- and oligomeric phosphinosuccinic acid (PSO) derivatives, polycarboxylic acid, hydrophobically modified polycarboxylic acid, and salts of a polymaleic acid/acrylic acid/acrylamidomethyl propane sulfonate terpolymer (PMA/AA/AMPS). Suitable polycarboxylic acid polymers may comprise of one or more monomers selected from the group consisting of acrylic acid, methacrylic acid, ethacrylic acid, maleic acid, maleic anhydride, and itaconic acid.

Alternatively, the cleaning composition or detergent composition disclosed herein can be free of a scale inhibitor.

Enzymes

The cleaning compositions or detergent compositions disclosed herein can include an enzyme. An enzyme in the cleaning compositions or detergent compositions enhances removal of soils, prevents re-deposition, and/or reduces foam during applications of the cleaning compositions or their use solutions. The function of an enzyme is to break down adherent soils, such as starch or proteinaceous materials, which are typically found in soiled surfaces and removed by a cleaning composition or detergent composition into a wash water source.

Exemplary types of enzymes which can be incorporated into the cleaning compositions or detergent compositions disclosed herein include, but are not limited to, amylase, protease, lipase, cellulase, cutinase, gluconase, peroxidase, and/or mixtures thereof. A cleaning composition disclosed herein may employ more than one enzyme, from any suitable origin, such as vegetable, animal, bacterial, fungal or yeast origin. The enzyme can be a protease. As used herein, the terms "protease" or "proteinase" refer enzymes that catalyze the hydrolysis of peptide bonds.

As understood by one skilled in the art, enzymes are designed to work with specific types of soils. For example, ware wash applications may use a protease enzyme as it is effective at the high temperatures of the ware wash machines and is effective in reducing protein-based soils. Protease enzymes are particularly advantageous for cleaning soils containing protein, such as blood, cutaneous scales, mucus, grass, food (e.g., egg, milk, spinach, meat residue, tomato sauce), or the like. Protease enzymes are capable of cleaving macromolecular protein links of amino acid residues and convert substrates into small fragments that are readily dissolved or dispersed into the aqueous use solution. Proteases are often referred to as detersive enzymes due to the ability to break soils through the chemical reaction known as hydrolysis. Protease enzymes can be obtained, for example, from *Bacillus subtilis, Bacillus licheniformis* and *Streptomyces griseus*. Protease enzymes are also commercially available as serine endoproteases.

Examples of commercially-available protease enzymes are available under the following trade names: ESPERASE®, PURAFECT®, PURAFECT L®, PURAFECT Ox®, EVERLASE®, LIQUANASE®, SAVINASE®, Prime L, Prosperase and BLAP.

The enzyme to be included into the cleaning composition may be an independent entity and/or may be formulated in combination with the cleaning composition. For example, the enzyme may be formulated into a cleaning composition in either liquid or solid formulations. In addition, enzyme compositions may be formulated into various delayed or controlled release formulations. For example, a solid molded cleaning composition may be prepared without the addition of heat. Enzymes can denature by heat so the use of enzymes within the cleaning compositions may require methods of forming cleaning compositions that do not rely upon heat as a step in the formation process, such as solidification.

The enzyme composition may be provided commercially in a solid (i.e., puck, powder, etc.) or liquid formulation. Commercially-available enzymes are generally combined with stabilizers, buffers, cofactors and inert vehicles. The actual active enzyme content depends upon the method of manufacture, as is understood in the art.

Alternatively, the enzyme composition may be provided separate from the cleaning or detergent composition, and, for example, be added directly to a use solution of a cleaning or detergent composition or a wash liquor, or wash water of an application, e.g. dishwasher.

Surfactant

The cleaning composition or detergent composition can also comprise a surfactant. The surfactant can be an anionic, cationic, nonionic, amphoteric, zwitterionic, and/or gemini surfactant.

Anionic Surfactants

The cleaning composition or detergent composition can comprise an anionic surfactant. Anionic surfactants are surface active substances in which the charge on the hydrophobe is negative; or surfactants in which the hydrophobic section of the molecule carries no charge unless the pH is elevated to neutrality or above (e.g., carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionic surfactants are excellent detersive surfactants and are therefore favored additions to heavy duty cleaning compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g., alkyl succinates), ether carboxylic acids, sulfonated fatty acids, such as sulfonated oleic acid, and the like. Such carboxylates include alkyl ethoxy carboxylates, alkyl aryl ethoxy carboxylates, alkyl polyethoxy polycarboxylate surfactants and soaps (e.g., alkyl carboxyls). Secondary carboxylates useful in the present compositions include those which contain a carboxyl unit connected to a secondary carbon. The secondary carbon can be in a ring structure, e.g., as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the group-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g., N-acyl sarcosinates), taurates (e.g., N-acyl taurates and fatty acid amides of methyl tauride), and the like.

Suitable anionic surfactants include alkyl or alkylaryl ethoxy carboxylates of the following formula:

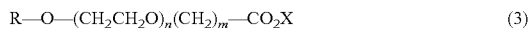

$$R-O-(CH_2CH_2O)_n(CH_2)_m-CO_2X \quad (3)$$

in which R is a $C_8$ to $C_{22}$ alkyl group or

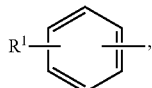

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

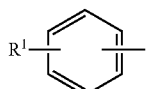

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include: NEODOX 23-4, a $C_{12}$-$C_{13}$ alkyl polyethoxy (4) carboxylic acid (Shell Chemical), and EMCOL CNP-110, a $C_9$ alkylaryl polyethoxy (10) carboxylic acid (Witco Chemical). Carboxylates are also available from Clariant, e.g., the product SANDOPAN DTC, a $C_{13}$ alkyl polyethoxy (7) carboxylic acid.

In some embodiments, the cleaning composition or detergent composition disclosed herein is free of an anionic surfactant.

Nonionic Surfactants

The cleaning composition or detergent composition can comprise a nonionic surfactant.

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties. Useful nonionic surfactants include block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available from BASF Corp. One class of compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Another class of compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Suitable nonionic surfactants also include condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names IGEPAL® manufactured by Rhone-Poulenc and TRITON® manufactured by Union Carbide.

The nonionic surfactants can also be condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names LUTENSOL™, DEHYDOL™ manufactured by BASF, NEODOL™ manufactured by Shell Chemical Co. and ALFONIC™ manufactured by Vista Chemical Co.

Nonionic surfactants also include condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names DISPONIL or AGNIQUE manufactured by BASF and LIPOPEG™ manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty esters or acylated carbohydrates to compositions of the present invention containing amylase and/or lipase enzymes because of potential incompatibility.

Examples of nonionic low foaming surfactants include, but are not limited to, compounds which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics are manufactured by BASF Corporation under the trade name PLURONIC™ R surfactants. Likewise, the TETRONIC™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Compounds which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionic surfactants include, but are not limited to:
(a) the alkylphenoxypolyethoxyalkanols of U.S. Pat. No. 2,903,486 issued Sep. 8, 1959 to Brown et al. and represented by the formula

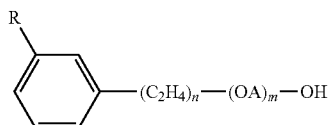

in which R is an alkyl group of 8 to 9 carbon atoms, A is an alkylene chain of 3 to 4 carbon atoms, n is an integer of 7 to 16, and m is an integer of 1 to 10.
(b) The polyalkylene glycol condensates of U.S. Pat. No. 3,048,548 issued Aug. 7, 1962 to Martin et al. having alternated hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.
(c) The defoaming nonionic surfactants disclosed in U.S. Pat. No. 3,382,178 issued May 7, 1968 to Lissant et al. having the general formula Z[(OR)nOH]z wherein Z is alkoxylatable material, R is a radical derived from an alkylene oxide which can be ethylene and propylene and n is an integer from, for example, 10 to 2,000 or more and z is an integer determined by the number of reactive oxyalkylatable groups.
(d) The conjugated polyoxyalkylene compounds described in U.S. Pat. No. 2,677,700, issued May 4, 1954 to Jackson et al. corresponding to the formula $Y(C_3H_6O)_n (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.
(e) The conjugated polyoxyalkylene compounds described in U.S. Pat. No. 2,674,619, issued Apr. 6, 1954 to Lundsted et al. having the formula $Y[(C_3H_6O)_n (C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n (C_2H_4O)_mH]x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R^2CONR^1Z$ in which: $R^1$ is H, $C_1$-$C_4$ hydrocarbyl, 2-hydroxy ethyl, 2-hydroxy propyl, ethoxy, propoxy group, or a mixture thereof; $R^2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside). The inter-saccharide bonds can be, e.g., between the one position of the additional saccharide units and the 2-, 3-, 4-, and/or 6-positions on the preceding saccharide units.

Fatty acid amide surfactants suitable for use the present compositions include those having the formula: $R^6CON(R^7)_2$ in which $R^6$ is an alkyl group containing from 7 to 21 carbon atoms and each $R^7$ is independently hydrogen, $C_1$-$C_4$ alkyl, $C_4$ hydroxyalkyl, or —$(C_2H_4O)_xH$, where x is in the range of from 1 to 3.

A useful class of non-ionic surfactants include the class defined as alkoxylated amines or, most particularly, alcohol alkoxylated/aminated/alkoxylated surfactants. These nonionic surfactants may be at least in part represented by the general formulae: $R^{20}$—$(PO)_sN$-$(EO)_tH$, $R^{20}$—$(PO)_sN$-$(EO)_tH(EO)_tH$, and $R^{20}$—$N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, and t is 1-10, preferably 2-5. Other variations on the scope of these compounds may be represented by the alternative formula: $R^{20}$—$(PO)_v$—$N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes SURFONIC™ PEA 25 Amine Alkoxylate. Preferred nonionic surfactants for the compositions of the invention include alcohol alkoxylates, EO/PO block copolymers, alkylphenol alkoxylates, and the like.

The treatise Nonionic Surfactants, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Suitable nonionic surfactants suitable for use with the compositions of the present invention include alkoxylated surfactants. Suitable alkoxylated surfactants include EO/PO copolymers, fully capped or partially EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)5(PO)4) and Dehypon LS-36 (R-(EO)3(PO)6); and capped alcohol alkoxylates, such as Plurafac LF221 and Tegoten EC11; mixtures thereof, or the like.

When the composition is not a cleaning composition, it can be free of a nonionic surfactant.

Semi-Polar Nonionic Surfactants

The cleaning composition or detergent composition can comprise a semi-polar nonionic surfactant.

The semi-polar type of nonionic surfactants is another class of nonionic surfactants useful in compositions disclosed herein. Generally, semi-polar nonionic surfactants are high foaming agents and foam stabilizers, which can limit their application in CIP systems. However, in some embodiments designed for high foaming composition or cleaning composition, semi-polar nonionic surfactants would have immediate utility. The semi-polar nonionic surfactants include, but are not limited to, the amine oxides, phosphine oxides, sulfoxides and their alkoxylated derivatives.

Amine oxides are tertiary amine oxides corresponding to the general formula:

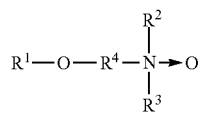

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water-soluble phosphine oxides having the following structure:

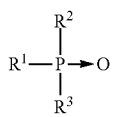

wherein the arrow is a conventional representation of a semi-polar bond; and, $R_1$ is an alkyl, alkenyl or hydroxyalkyl moiety ranging from 10 to about 24 carbon atoms in chain length; and, $R_2$ and $R_3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

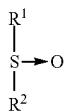

wherein the arrow is a conventional representation of a semi-polar bond; and, $R_1$ is an alkyl or hydroxyalkyl moiety of about 8 to about 28 carbon atoms, from 0 to about 5 ether linkages and from 0 to about 2 hydroxyl substituents; and $R_2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Alternatively, the cleaning composition or detergent composition disclosed herein can be free of a semi-polar nonionic surfactant.

Cationic Surfactants

The cleaning composition or detergent composition can comprise a cationic surfactant.

Surface active substances are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. In theory, cationic surfactants may be synthesized from any combination of elements containing an "onium" structure RnX+Y— and could include compounds other than nitrogen (ammonium) such as phosphorus (phosphonium) and sulfur (sulfonium). In practice, the cationic surfactant field is dominated by nitrogen containing compounds, probably because synthetic routes to nitrogenous cationics are simple and straightforward and give high yields of product, which can make them less expensive.

Cationic surfactants preferably include, and more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced, or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

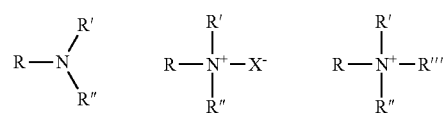

in which, R represents an alkyl chain, R', R", and R'" may be either alkyl chains or aryl groups or hydrogen and X represents an anion. The amine salts and quaternary ammonium compounds are preferred for practical use in this invention due to their high degree of water solubility.

Most large volume commercial cationic surfactants can be subdivided into four major classes and additional sub-groups known to those skilled in the art and described in "Surfactant Encyclopedia", Cosmetics & Toiletries, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions disclosed herein include those having the formula $R^1{}_mR^2{}_xY_LZ$ wherein each $R^1$ is an organic group containing a straight or branched alkyl or alkenyl group optionally substituted with up to three phenyl or hydroxy groups and optionally interrupted by up to four of the following structures:

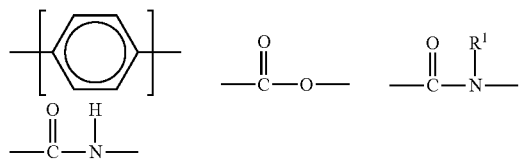

or an isomer or mixture of these structures, and which contains from about 8 to 22 carbon atoms. The $R^1$ groups can additionally contain up to 12 ethoxy groups and m is a number from 1 to 3. Preferably, no more than one $R_1$ group in a molecule has 16 or more carbon atoms when m is 2 or more than 12 carbon atoms when m is 3. Each $R_2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens.

Y is can be a group including, but not limited to:

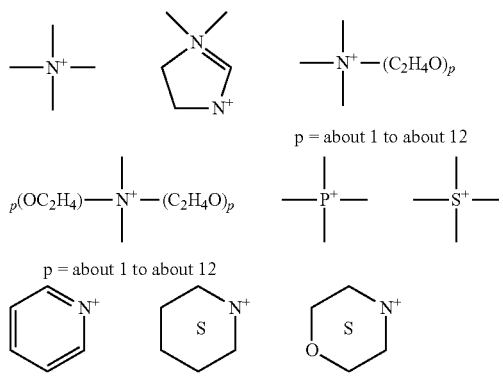

or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water-soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

Alternatively, the cleaning composition or detergent composition disclosed herein can be free of a cationic surfactant.

Amphoteric Surfactants

The cleaning composition or detergent composition can comprise an amphoteric surfactant.

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

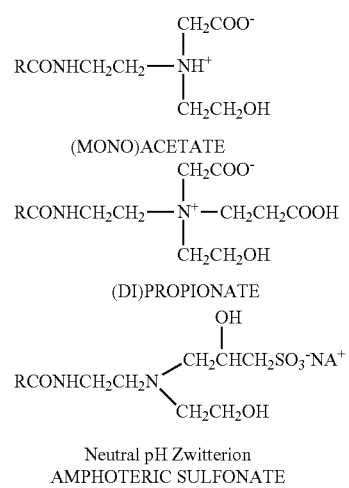

Neutral pH Zwitterion
AMPHOTERIC SULFONATE wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: cocoamphopropionate, cocoamphocarboxy-propionate, cocoamphoglycinate, cocoamphocarboxy-glycinate, cocoamphopropyl-sulfonate, and cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterionic Surfactants.

Long chain N-alkylamino acids are readily prepared by reaction $RNH_2$, in which $R=C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—CH$_2$—CH$_2$—N+(CH$_2$—CH$_2$—CO$_2$Na)$_2$—CH$_2$—CH$_2$—OH or $C_{12}$-alkyl-C(O)—N(H)—CH$_2$—CH$_2$—N+(CH$_2$—CO$_2$Na)$_2$-CH$_2$—CH$_2$—OH. Disodium cocoampho dipropionate is one suitable amphoteric surfactant and is commercially available under the tradename MIRANOL™ FBS from Rhodia Inc., Cranbury, N.J. Another suitable coconut derived amphoteric surfactant with the chemical name disodium cocoampho diacetate is sold under the tradename MIRATAINE™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated by reference in their entirety.

Alternatively, the cleaning composition or detergent composition disclosed herein can be free of an amphoteric surfactant.

Zwitterionic Surfactants

The cleaning composition or detergent composition can comprise a zwitterionic surfactant.

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionic surfactants generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

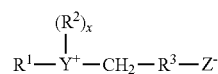

wherein $R_1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N, N-dimethyl-N-hexadecylammonio)-2-hydroxy-propane-1-sulfonate; 4-[N, N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said cleaning composition surfactants can be straight or branched and saturated or unsaturated.

The zwitterionic surfactant suitable for use in the present compositions includes a betaine of the general structure:

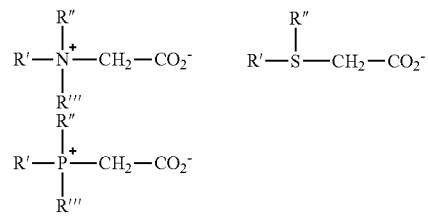

wherein R', R", and R'" are linear or branched alkyl or alkyl ether groups.

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12}$-14 acylamidopropylbetaine; $C_8$-14 acylamidohexyldiethyl betaine; 4-$C_{14}$-16 acylmethylamidodiethylammonio-1-carboxybutane; $C_{16}$-18 acylamidodimethylbetaine; $C_{12}$-16 acylamidopentanediethylbetaine; and $C_{12}$-16 acylmethylamidodimethylbetaine.

Sultaines useful in the present invention include those compounds having the formula $(R(R^1)_2N^+R^2SO_3—$, in which R is a $C_6$-$C_{18}$ hydrocarbyl group, each $R^1$ is typically independently $C_1$-$C_3$ alkyl, e.g., methyl, and $R^2$ is a $C_1$-$C_6$ hydrocarbyl group, e.g., a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Alternatively, the detergent composition or cleaning composition disclosed herein can be free of a zwitterionic surfactant.

Gemini Surfactants

The cleaning composition or detergent composition can comprise a Gemini surfactant.

While conventional surfactants generally have one hydrophilic group and one hydrophobic group, a Gemini surfactant has at least two hydrophobic groups and at least two hydrophilic groups. These surfactants have the general formula: A1-G-A2 and get their name because they comprise two surfactant moieties (A1, A2) joined by a spacer (G), wherein each surfactant moiety (A1, A2) has a hydrophilic group and a hydrophobic group. Generally, the two surfactant moieties (A1, A2) are the same, but they can be different.

The Gemini surfactants may be anionic, nonionic, cationic or amphoteric. The hydrophilic and hydrophobic groups of each surfactant moiety (A1, A2) may be any of those known to be used in conventional surfactants having one hydrophilic group and one hydrophobic group. For example, a typical nonionic Gemini surfactant, e.g., a bis-polyoxyethylene alkyl ether, would contain two polyoxyethylene alkyl ether moieties.

Each moiety would contain a hydrophilic group, e.g., polyethylene oxide, and a hydrophobic group, e.g., an alkyl chain.

Anionic and nonionic Gemini surfactants include those of the formula:

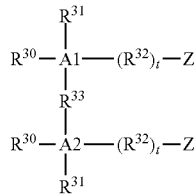

wherein $R^{30}$ is independently $C_1$ to $C_{22}$ alkyl, $R^{34}$—C(O)—, or $R^{34}$—B—$R^{35}$—, wherein $R^{34}$ is $C_1$ to $C_{22}$ alkyl, $R^{35}$ is $C_1$ to $C_{12}$ alkyl, and B is an amide group, —C(O)N($R^{36}$)—, an amino group —N($R^{36}$)—, a carboxyl group —C(O)—O—, a carbonyl group, or a polyether group —(EO)$_a$(PO)$_b$—, wherein EO represents ethyleneoxy radicals, PO represents propyleneoxy radicals, a and b are numbers of from 0 to 100, a is preferably from about 0 to about 30 and b is preferably from about 0 to 10, wherein the sum of a and b is at least one, and the EO and PO radicals can be randomly mixed or in discrete blocks, and $R^{36}$ is hydrogen or $C_1$ to $C_6$ alkyl.

$R^{31}$ is independently hydrogen or $C_1$ to $C_{22}$ alkyl; $R^{32}$ is independently a $C_1$-$C_{10}$ alkyl, —O—, an amide group —C(O)N($R^6$)—, a polyether group —O(EO)$_a$(PO)$_b$—, —$R^{37}$-D-$R^{37}$—, or -D-$R^{37}$-D-, wherein $R^{37}$ is independently a $C_1$-$C_6$ alkyl and D is —O—, —S—, an amide group —C(O)N($R^{36}$)—, or an amino group —N($R^{36}$)—, wherein $R^{36}$, a and b are as defined above, and t is independently 0 or 1.

Z is independently hydrogen, —SO$_3$Y, —P(O)(OY)$_2$, —COOY, —CH$_2$COOY, —CH$_2$CH(OH)CH$_2$SO$_3$Y and when $R^{32}$ is not a polyether, Z is also —OSO$_3$Y, and —OP(O)(OY)$_2$; wherein Y is hydrogen, alkali metal such as sodium and potassium; alkaline earth metal such as magnesium and calcium; ammonium; or organic base salt such as monoethanolamine, diethanolamine, triethanolamine, triethylamine, trimethylamine, N-hydroxyethyl morpholine, and the like.

A1 or A2 is independently a straight chain or branched $C_1$ to $C_6$ alkyl, an O—$R^5$—O— group or aryl; preferably phenyl; $R^{33}$ is a bond, an aryl group such as a phenyl or diphenyl group, a $C_1$ to $C_{10}$ alkyl group, preferably a $C_1$ to $C_4$ alkyl group, most preferably methylene, —C≡C—, —O—, —S—S—, —N($R_{36}$)—, —$R^{35}$O (EO)$_a$(PO)$_b$—, -D1-$R^{38}$-D1- or —$R^{38}$-D1-$R^{38}$—, wherein $R^{38}$ is independently a $C_1$-$C_{10}$ alkyl group, —C(O)—, —$R^{35}$O(EO)$_a$(PO)$_b$—, or aryl, e.g. phenyl, and D1 is independently —O—, —S—S—, —SO$_2$—C(O)—, a polyether group —O(EO)$_a$(PO)$_b$—, an amide group —C(O)N($R^{36}$)—, an amino group —N($R^{36}$)—, —O—$R^5$—O—, or aryl wherein $R^{35}$, $R^{36}$, a and b are as defined above.

On the formulae of this disclosure, the term "alkali" includes substituted alkali, especially the hydroxy substituted derivatives thereof and straight as well as branched chains. When Z is hydrogen, the gemini surfactants are nonionic.

Other Gemini surfactants specifically useful in the present disclosure include gemini anionic or nonionic surfactants of the formulae:

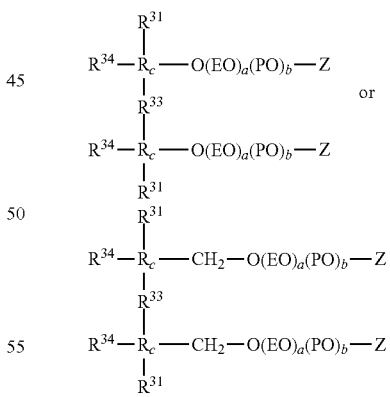

wherein $R_c$ represents aryl, preferably phenyl. $R^{31}$, $R^{33}$, $R^{34}$, and Z are as defined above. a and b are numbers of from 0 to 100, a is preferably from about 0 to about 30 and b is preferably from about 0 to 10, wherein the sum of a and b is at least one, and the EO and PO radicals can be randomly mixed or in discrete blocks.

The primary hydroxyl group of these surfactants can be readily phosphated, sulfated or carboxylated by standard techniques.

Alternatively, the detergent composition or cleaning composition disclosed herein can free of a Gemini surfactant.

Additional Components

The cleaning composition or detergent composition disclosed herein may also include one or more additional cleaning composition agents. Exemplary additional cleaning composition agents include, but are not limited to, a threshold agent; crystal modifier; hardening agent; bleaching agent; peroxycarboxylic acid, peroxycarboxylic acid composition, filler; defoaming agent; anti-redeposition agent; stabilizing agent; dispersant; fragrance and dye; and thickener.

Alternatively, the cleaning composition or detergent composition disclosed herein can be free of one, more, or all the additional cleaning composition agents.

Preparation of Compositions Herein

In one example, a compound of formula 1 is combined with any additional functional components and allowed to interact and harden into solid form. The solidification process may last from a few minutes to about six hours, depending on factors including, but not limited to: the size of the formed or cast composition, the ingredients of the composition, and the temperature of the composition.

The solid compositions may be formed using a batch or continuous mixing system. In an exemplary embodiment, a single- or twin-screw extruder is used to combine and mix one or more cleaning agents at high shear to form a homogeneous mixture. In some embodiments, the processing temperature is at or below the melting temperature of the components. The processed mixture may be dispensed from the mixer by forming, casting or other suitable means, whereupon the composition hardens to a solid form. The structure of the matrix may be characterized according to its hardness, melting point, material distribution, crystal structure, and other like properties according to known methods in the art. Generally, a solid composition processed according to the method of the invention is substantially homogeneous with regard to the distribution of ingredients throughout its mass and is dimensionally stable.

In an extrusion process, the liquid and solid components are introduced into final mixing system and are continuously mixed until the components form a substantially homogeneous semi-solid mixture in which the components are distributed throughout its mass. The mixture is then discharged from the mixing system into, or through, a die or other shaping means. The product is then packaged. In an exemplary embodiment, the formed composition begins to harden to a solid form in from approximately 1 minute to approximately 3 hours. Particularly, the formed composition begins to harden to a solid form from approximately 1 minute to approximately 2 hours. More particularly, the formed composition begins to harden to a solid form from approximately 1 minute to approximately 20 minutes.

In a casting process, the liquid and solid components are introduced into the final mixing system and are continuously mixed until the components form a substantially homogeneous liquid mixture in which the components are distributed throughout its mass. For example, the components can be mixed in the mixing system for at least approximately 60 seconds. Once the mixing is complete, the product is transferred to a packaging container where solidification takes place. In an exemplary embodiment, the cast composition begins to harden to a solid form in from approximately 1 minute to approximately 3 hours. Particularly, the cast composition begins to harden to a solid form in from approximately 1 minute to approximately 2 hours. More particularly, the cast composition begins to harden to a solid form approximately 1 minute to approximately 20 minutes.

By the term "solid", it is meant that the hardened composition will not flow and will substantially retain its shape under moderate stress or pressure or mere gravity. The degree of hardness of the solid cast composition may range from that of a fused solid product which is relatively dense and hard, for example, like concrete, to a consistency characterized as being a hardened paste. In addition, the term "solid" refers to the state of the composition under the expected conditions of storage and use of the solid composition. In general, it is expected that the composition will remain in solid form when exposed to temperatures of up to approximately 100° F. and particularly up to approximately 120° F.

The resulting solid composition may take forms including, but not limited to: a cast solid product; an extruded, pressed, molded or formed solid pellet, block, tablet, powder, granule, flake; or the formed solid can thereafter be ground or formed into a powder, granule, or flake. For example, extruded pellet materials formed by the solidification matrix can have a weight of about 50 grams to about 250 grams, extruded solids formed by the composition can have a weight greater than or equal to about 100 grams, and solid block cleaning compositions formed by the composition can have a mass of about 1 to about 10 kilograms. The solid compositions provide for a stabilized source of functional materials. In some embodiments, the solid composition may be dissolved, for example, in an aqueous or other medium, to create a concentrated and/or use composition. The solution may be directed to a storage reservoir for later use and/or dilution, or may be applied directly to a point of use.

The solid composition can be provided in the form of a unit dose. A unit dose refers to a solid composition unit sized so that the entire unit is used during a single washing cycle. When the solid composition is provided as a unit dose, it is typically provided as a cast solid, an extruded pellet, or a tablet having a size of approximately 1 gram to approximately 50 grams.

The solid composition can also be provided in the form of a multiple-use solid, such as a block or a plurality of pellets, and can be repeatedly used to generate aqueous compositions for multiple washing cycles. For example, the solid composition can be provided as a cast solid, an extruded block, or a tablet having a mass of about 5 grams to about 10 kilograms, from about 1 kilogram to about 10 kilograms, or from about 5 kilograms to about 8 kilograms. Alternatively, a multiple-use form of the solid composition can have a mass of about 5 grams to about 1 kilogram or about 5 grams to about 500 grams.

Although the composition is discussed as being formed into a solid product, the composition may also be provided in the form of a paste or liquid. When the concentrate is provided in the form of a paste, enough water is added to the composition such that complete solidification of the composition is precluded. In addition, dispersants and other components may be incorporated into the composition in order to maintain a desired distribution of components.

When used in the methods described herein below, the cleaning compositions or detergent compositions may be ready to use solutions or concentrate compositions which may be added to an aqueous system or may be diluted to form use compositions. In general, a concentrate refers to a composition that is intended to be added to or diluted with water, and the composition that contacts articles to be washed can be referred to as the use composition.

A use composition may be prepared from the concentrate by diluting the concentrate with water at a dilution ratio that provides a use composition having desired detersive properties. The water that is used to dilute the concentrate to form the use composition can be referred to as water of dilution, or a diluent, and can vary from one location to another. The use composition can also include additional functional ingredients at a level suitable for cleaning, rinsing, or the like.

The concentrate compositions may essentially include only a compound or compounds of formula 1, and additional components and/or functional materials may be added as separate ingredients prior to the point of use or at the point of use. Alternatively, the concentrate compositions may include a compound or compounds of formula 1 as well as additional components such as, but not limited to, at least one alkali metal hydroxide.

The typical dilution factor for the cleaning composition or detergent composition is from approximately 1 to approximately 10,000 but will depend on factors including water hardness, the amount of soil to be removed and the like. For example, the concentrate is diluted at a ratio of about 1:10 to about 1:1000 concentrate to water. Particularly, the concentrate is diluted at a ratio of about 1:100 to about 1:5000 concentrate to water. More particularly, the concentrate is diluted at a ratio of about 1:250 to about 1:2000 concentrate to water.

For the purpose of illustration, representative non-limiting cleaning or detergent compositions comprising the compound of Formula 1, 2 or 3 that are useful for various applications are provided herein.

The article can comprise a metal surface, a glass surface, a fabric, a ware, a polycarbonate surface, a polysulfone surface, a melamine surface, a ceramic surface, a porcelain surface, or a combination thereof. Preferably, the article is a fabric. More preferably, the article is a ware.

Also provided are methods for cleaning a membrane. The methods comprise contacting the membrane with a cleaning solution comprising any compound of Formula 1, 2, or 3 as described herein.

The membrane may be contacted with from about 10 to about 5,000 ppm of the compound of Formula 1, 2, or 3, based on the total weight of the fluid contacting the membrane.

In the methods disclosed herein, the membrane can be a membrane used in a dairy process. For example, the membrane can be a microfiltration membrane, an ultrafiltration membrane, a nanofiltration membrane, a reverse osmosis membrane or a combination thereof.

Definitions

As used herein, the term "substantially free", "free" or "free of" refers to compositions completely lacking the component or having such a small amount of the component that the component does not affect the performance of the composition. The component may be present as an impurity or as a contaminant and shall be less than 0.5 wt. %. For example, the amount of the component can less than 0.1 wt. % or, in some cases, the amount of component can be less than 0.01 wt. %.

| Hard Surface Cleaner/ Degreaser pH ≥ 2 | Dishwashing/ Warewashing Detergent pH ≥ 5 | Laundry Detergent pH ≥ 5 | Manual Pot and Pan Presoak pH ≥ 5 | Clean-in-Place Formulation pH ≥ 1 |
|---|---|---|---|---|
| Compound of Formula 1, 2 or 3 Surfactant Alkalinity Source Organic or Inorganic Acid Water conditioning agents Solvent Water Adjuvant ingredients | Compound of Formula 1, 2 or 3 Alkalinity Source Surfactant Water conditioning agents Enzyme Oxidizer Water Adjuvant ingredients | Compound of Formula 1, 2 or 3 Alkalinity Source Surfactant Water conditioning agents Enzyme Oxidizer Water Optical Brightener Adjuvant ingredients | Compound of Formula 1, 2 or 3 Alkalinity Source Surfactant Water conditioning agents Enzyme Water Adjuvant ingredients | Compound of Formula 1, 2 or 3 Alkalinity Source OR Organic or Inorganic Acid Surfactant Water conditioning agents Enzyme Water Adjuvant ingredients |

Methods of cleaning an article are also provided. The methods comprise contacting the article with a detergent composition comprising a compound of Formula 1, 2, or 3 as described herein. As described above, the detergent composition can further comprise a building agent. The building agent can comprise an enzyme, an oxidizing agent, a condensed phosphate, an alkali metal carbonate, an alkali metal silicate, an alkali metal metasilicate, a phosphonate, an amino carboxylic acid, a carboxylic acid polymer, or a combination thereof.

The article can be contacted with from about 50 to about 6,000 ppm of the cleaning composition based on the total volume of the fluid in contact with the article.

The article can be contacted with from about 10 to about 3,000 ppm of the compound of Formula 1, 2, or 3 based on the total volume of the fluid in contact with the article.

The term "weight percent", "wt. %", "percent by weight", "% by weight", and variations thereof, as used herein, refer to the concentration of a substance as the weight of that substance divided by the total weight of the composition and multiplied by 100. It is understood that, as used here, "percent", "%", and the like are intended to be synonymous with "weight percent", "wt. %", etc.

As used herein, the term "polymer" means a water-soluble or water-dispersible polymer. The term "polymer" encompasses and includes homopolymers, copolymers, terpolymers and polymers with more than three monomers, crosslinked or partially crosslinked polymers, and combinations or blends of these.

As used herein, the term "polymer solution" or "polymer dispersion" means a polymer composition substantially dispersed or dissolved in water, a water source, or a water-based solution. Water-based solutions include one or more dissolved salts, buffers, acids, bases, surfactants, or other dissolved, dispersed, or emulsified compounds, materials, components, or combinations thereof.

As used herein, "inverse emulsion polymer" and "inverse latex polymer" mean a water-in-oil polymer emulsion comprising a water-soluble polymer (which could be cationic, anionic, nonionic, amphoteric polymer, or zwitterionic) in the aqueous phase, a hydrocarbon oil for the oil phase and a water-in-oil emulsifying agent. Inverse emulsion polymers are hydrocarbon continuous with the water-soluble polymers dispersed within the hydrocarbon matrix. The inverse emulsion polymers are then "inverted" or activated for use by releasing the polymer from the particles using shear, dilution, and generally another surfactant. See U.S. Pat. No. 3,734,873, incorporated herein by reference.

As used herein, the term "water source" means a source of water comprising, consisting essentially of, or consisting of fresh water, deionized water, distilled water, produced water, municipal water, waste water such as runoff water or municipal waste water, treated or partially treated waste water, well water, brackish water, "gray water", sea water, or a combination of two or more such water sources as determined by context. A water source can include one or more salts, ions, buffers, acids, bases, surfactants, or other dissolved, dispersed, or emulsified compounds, materials, components, or combinations thereof.

As used herein, the terms "water-in-oil emulsion" mean a discontinuous internal water phase within a continuous oil phase, wherein the water phase includes at least one monomer or polymer. In general and as determined by context, these terms denote an emulsion prior to addition of inversion surfactants.

As used herein, the term "oil" or "hydrocarbon solvent" as applied to an oil phase of a water-in-oil emulsion, means any compound or blend thereof that is less than 0.1 wt % soluble in water at 25° C., is substantially chemically inert within a water-in-oil emulsion as described herein, and is a liquid over at least the range of 20° C. to 100° C.

As used herein, the term "water phase" means a water source having at least a monomer or polymer dispersed or dissolved therein, further wherein the dispersion or solution is a discontinuous phase within a water-in-oil emulsion.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The terms "aryl" or "ar" as used herein alone or as part of another group (e.g., arylalkyl) denote optionally substituted homocyclic aromatic groups, preferably monocyclic or bicyclic groups containing form 6 to 12 carbon atoms in the ring portion, such as phenyl, biphenyl, naphthyl, substituted phenyl, substituted biphenyl, or substituted naphthyl. Phenyl and substituted phenyl are the more preferred aryl groups. The term "aryl" also includes heteroaryl functional groups.

"Arylalkyl" means an aryl group attached to the parent molecule through an alkylene group. The number of carbon atoms in the aryl group and the alkylene group is selected such that there is a total of about 6 to about 18 carbon atoms in the arylalkyl group. A preferred arylalkyl group is benzyl.

The term "substituted," as in "substituted aryl," "substituted alkyl," and the like, means that in the group in question (i.e., the alkyl, aryl, or other group that follows the term), at least one hydrogen atom bound to a carbon atom is replaced with one or more substituent groups such as hydroxy (—OH), alkylthio, amido (—CON($R_A$)($R_B$), wherein $R_A$ and $R_B$ are independently hydrogen, alkyl, or aryl), amino (—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," "heterocycle," or "heterocyclyl," as used herein, refers to a monocyclic, bicyclic, or tricyclic group containing 1 to 4 heteroatoms selected from N, O, S(O)n, P(O)n, PRz, NH or NRz, wherein Rz is a suitable substituent. Heterocyclic groups optionally contain one or two double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2 yl, tetrahydrofuran-3-yl, imidazolidin-1-yl, imidazolidin-2 yl, imidazolidin-4-yl, pyrrolidin-1-yl, pyrrolidin-2 yl, pyrrolidin-3-yl, piperidin-1-yl, piperidin-2 yl, piperidin-3-yl, piperazin-1-yl, piperazin-2 yl, piperazin-3-yl, 1,3-oxazolidin-3-yl, isothiazolidine, 1,3-thiazolidin-3-yl, 1,2 pyrazolidin-2 yl, 1,3-pyrazolidin-1-yl, thiomorpholin-yl, 1,2 tetrahydrothiazin-2 yl, 1,3-tetrahydrothiazin-3-yl, tetrahydrothiadiazin-yl, morpholin-yl, 1,2 tetrahydrodiazin-2 yl, 1,3-tetrahydrodiazin-1-yl, 1,4-oxazin-2 yl, and 1,2,5 oxathiazin-4-yl. Heterocyclic groups can be unsubstituted or substituted by one or more suitable substituents, preferably 1 to 3 suitable substituents, as defined above.

Having described the invention in detail, it will be apparent that modifications and variations are possible without departing from the scope of the invention defined in the appended claims.

EXAMPLES

The following non-limiting examples are provided to further illustrate the present invention.

Example A: Synthesis of Novel Surfactant Compositions

The overall synthesis of the surfactants described herein is achieved in two steps (Scheme 1). Acceptor molecule (C) is first prepared by ring opening reaction of an alkyl-epoxide (II) with an aromatic amine or alcohol compound (A). The second step involves oxyalkylation of the acceptor molecule (C) with alkylene oxide (D) to afford a series of surfactants (E).

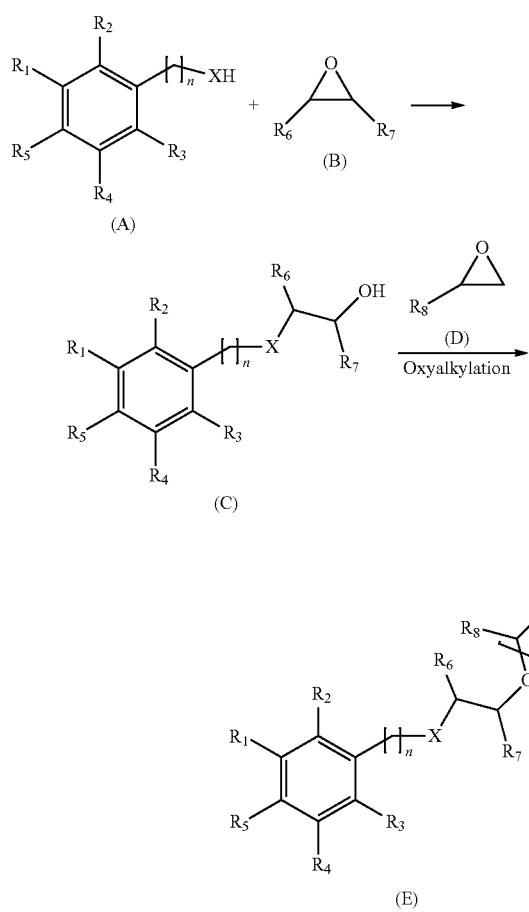

(A), (B), (C), (D) Oxyalkylation, (E)

wherein X, $R_1$, $R_2$, $R_3$, $R_4$, $R_5$, $R_6$, $R_7$, $R_8$, m, and n are defined above.

Examples 1 and 2 disclose the specific synthesis of a series of ethoxylated 1-((2-ethylhexyl)oxy-3-phenoxypropan-2-ol via the following two step process (Scheme 2):

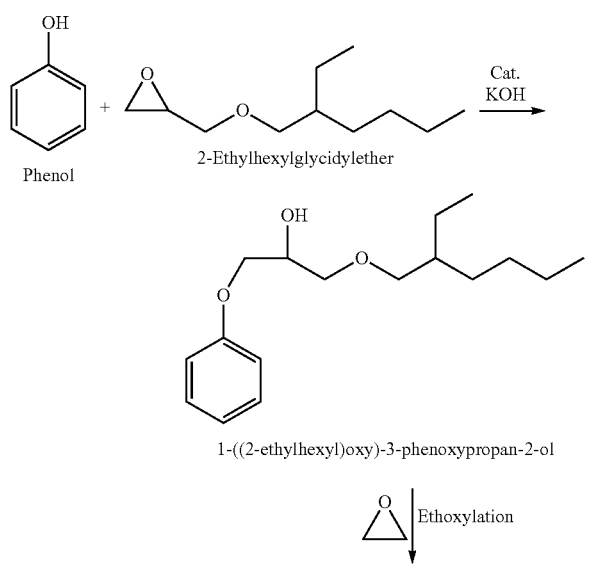

(Scheme 2)

Phenol + 2-Ethylhexylglycidylether →(Cat. KOH)→ 1-((2-ethylhexyl)oxy)-3-phenoxypropan-2-ol →(Ethoxylation)→

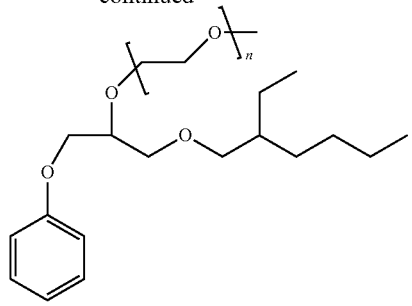

Example 1A: Synthesis of 1-((2-ethylhexyl)oxy)-3-phenoxypropan-2-ol

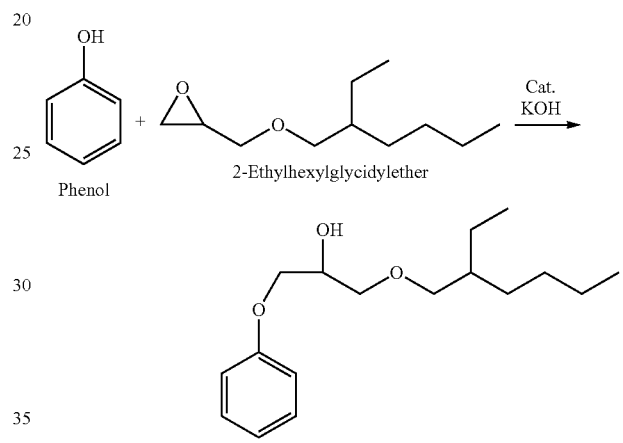

TABLE 1

| Reagent | MW(g/mol) | Mass(g) | n(mole) |
|---|---|---|---|
| Phenol | 94.11 | 100 | 1.06 |
| 2-Ethylhexyl glycidyl ether | 186.29 | 200 | 1.06 |
| KOH Pallets | 56.11 | 1 | 0.02 |

Figure 2:
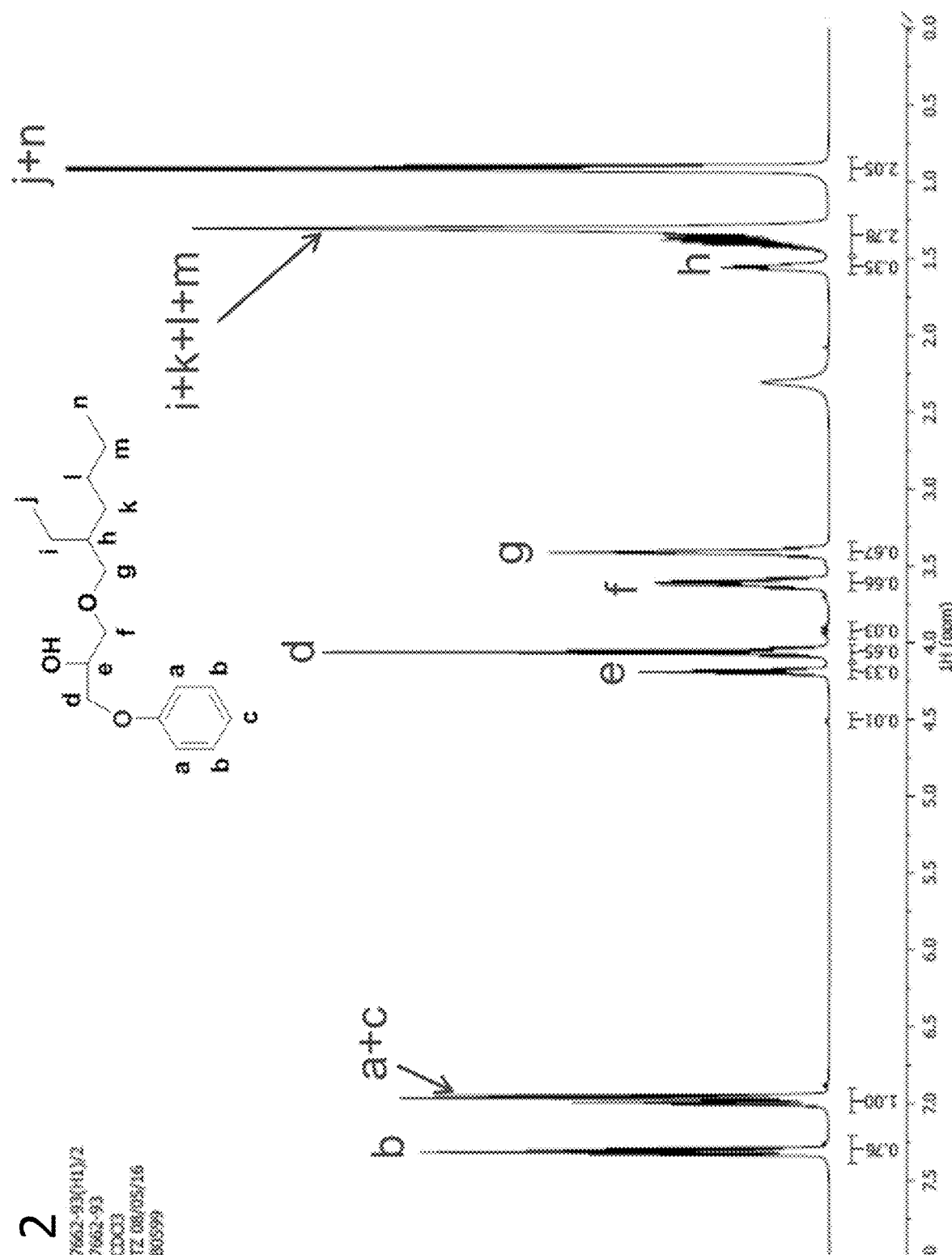
FIG. 2 is a $^1$H NMR for the product of Example 1.

Phenol (100 g, 1.06 mole) and potassium hydroxide (1 g, 0.02 mole) were added to a 500 mL three necked round-bottom flask equipped with temperature probe, condenser, nitrogen inlet and magnetic stir bar and the temperature of the reaction increased to 50° C. 2-Ethylhexylglycidal ether (200 g, 1.06 moles) was then added to the molten phenol under nitrogen blanket. The temperature of the reaction was further increased to 130° C. and stirred for 4 hours or until completion of reaction. The progress of the reaction was monitored by GC-MS (FIG. 1). The structure of the resulting compound was confirmed by NMR (FIG. 2) and mass spectrometry (+ESI-MS): calc. [M+H]+ 281.21, found 281.2109.

Example 1B: Addition of Ethylene Oxide to the 1-((2-ethylhexyl)oxy)-3-phenoxypropan-2-ol After catalyzing and dehydrating, 505.93 g of 1-((2-ethylhexyl)oxy-3-phenoxypropan-2-ol was charged to a 2-liter Parr reactor and heated to 125° C. under 10 psi of nitrogen at a stirrer speed of 300 rpm. The ethoxylation reaction was initiated when the acceptor material reached 125° C. The ethylene oxide was charged in step-wise fashion to slowly increase the working pressure range of 55-65 psi during the oxide feed. A slight exotherm was observed. Once the target amount of ethylene oxide, 476.5 g (6 mol), was charged to the reactor, the oxide feed was discontinued and the reaction was allowed to proceed for 6 hours at 125° C. The material was then cooled and sampled for testing. Preparation of intermediates with increasing levels of ethylene oxide (6-13 mol EO) was completed through addition of the desired amounts of EO.

Example 2A: Synthesis of 3,3'-((4-hydroxyphenyl)azanediyl)bis(1-((2-ethylhexyl)oxy)propan-2-ol)

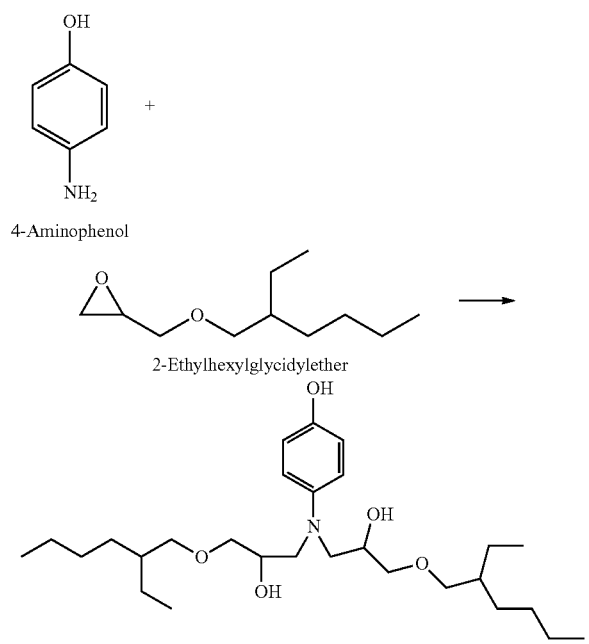

TABLE 1

| Reagent | MW(g/mol) | Mass(g) | n(moles) |
| --- | --- | --- | --- |
| 4-Aminophenol | 109.13 | 176 | 1.612 |
| 2-ethylhexylglycidyl ether | 186.29 | 600 | 3.22 |

To a 1 L three necked round-bottom flask equipped with temperature probe, nitrogen inlet, condenser and magnetic stir bar was added 2-ethylhexylglycidal ether (600 g, 3.22 moles). 4-Aminophenol (176 g, 1.612 mole) was then added to the well-stirred reaction mixture. The resulting suspension was heated to 120° C. under a nitrogen blanket and stirred for 3 hours or until the reaction was completed. As the reaction proceeded to completion, the suspension turned into a homogenous dark-amber product. The resulting product was characterized by NMR and ESI-MS.

Example 2B: Addition of Ethylene Oxide to the 3,3'-((4-hydroxyphenyl)azanediyl)bis(1-((2-ethylhexyl)oxy)propan-2-ol)

After catalyzing and dehydrating, 481.72 g of 3,3'-((4-hydroxyphenyl)azanediyl)bis(1-((2-ethylhexyl)oxy)propan-2-ol) was charged to a 2-liter Parr reactor and heated to 125° C. under 10 psi of nitrogen at a stirrer speed of 300 rpm. The ethoxylation reaction was initiated when the acceptor material reached 125° C. The ethylene oxide was charged in step-wise fashion to slowly increase the working pressure range of 55-65 psi during the oxide feed. A slight exotherm was observed. Once the target amount of ethylene oxide, 440.5 g (10 mol), was charged to the reactor, the oxide feed was discontinued and the reaction was allowed to proceed for 6 hours at 125° C. The material was then cooled and sampled for testing. Preparation of intermediates with increasing levels of ethylene oxide (10-24 mol O-EO) was completed through addition of the desired amounts of EO.

Example B: Materials and Methods for Examples 3 to 6

Activating Surfactants:
Surfactants listed in table below were used for evaluation testing.

TABLE 2

Activators and Surfactants

| Description | ID used in the examples | Type |
| --- | --- | --- |
| Dow Tergitol NP-9.5 | Activator #1 | Nonylphenol ethoxylate |
| Sasol Alfonic 1412-7 | Activator #2 | Alcohol ethoxylate |
| Huntsman Surfonic TDA-9 | Activator #3 | Alcohol ethoxylate |
| Huntsman Surfonic TDA-12 | Activator #4 | Alcohol ethoxylate |
| NP-12 (NPE with 12 moles of EO) | Activator #5 | Nonylphenol ethoxylate |
| 1-((2-ethylhexyl)oxy)-3-phenoxypropan-2-ol ethoxylate | nEO, where n indicates moles of EO units | Surfactants (Prepared as in Examples 1A and 1B) |

Preparation of Polymer Blends:
The polymer blends containing inverting surfactants (at the concentrations indicated in the examples) were prepared directly in 4 oz. jars. The inverting surfactant was added drop-wise to the un-activated latex while mixing at 800 rpm with a small cage stirrer. Following addition, the resulting mixture was stirred for one hour and then allowed to equilibrate for at least two additional hours.

Preparation of Synthetic Sea Water (SSW)
The 3.5% synthetic seawater was prepared by blending the components of Table 3. SSW was filtered through a WHATMAN 1 filter by suction filtration to remove any particulates.

TABLE 3

Ingredients of 3.5% SSW

| Reagent | Amount (g) |
| --- | --- |
| Sodium chloride (NaCl) | 73.95 |
| Calcium chloride $CaCl_2 \cdot 2H_2O$ | 4.71 |
| Magnesium chloride ($MgCl_2 \cdot 6H_2O$) | 341.7 |
| Sodium bicarbonate ($NaHCO_3$) | 0.03 |
| Sodium sulfate ($Na_2SO_4$) | 13.14 |
| Deionized water | 2873.97 |
| Total | 3000 |

Preparation of High Total Dissolved Solids (TDS) Brine (12.5%)
The 12.5% TDS brine was prepared by blending the components of Table 4. Brine was filtered through a WHATMAN 1 filter by suction filtration to remove any particulates.

TABLE 4

| Ingredients of 12.5% TDS brine | |
| --- | --- |
| Reagent | Amount (g) |
| Sodium chloride (NaCl) | 91.83 |
| Calcium chloride CaCl$_2$•2H$_2$O | 21.60 |
| Magnesium chloride (MgCl$_2$•6H$_2$O) | 7.71 |
| Potassium chloride (KCl) | 0.908 |
| Strontium chloride SrCl$_2$ 6H$_2$O | 1.179 |
| Deionized water | 876.77 |
| Total | 1000 |

Evaluation Method: Inversion Torque Monitor

The rate of inversion, or rate of viscosity build, is an important determinant of activity for emulsion inverse polymers. Field applications generally require that inversion occurs rapidly. In the laboratory, the rate and extension of inversion of polymer blends containing different surfactants is determined by analytical tool referred to as an "inversion torque monitor (ITM)." The inversion efficacy of surfactants was compared to some commonly used inverters (by Nalco in polymer formulations) using ITM.

The ITM consisted of a DC stir motor, a controller that can report the torque (DC voltage) required to maintain a constant stir speed, and a computer to record the torque reading as a function of time. This method involves injecting polymer blends into a larger volume of solvent while recording the force required to turn a large cage stirrer at a specified RPM in the inverting solution. Torque readings were collected every second and data worked-up in Microsoft Excel using a 20-period moving average.

Conditions: Torque monitor tests were conducted at the 500 g scale in a 1000-mL beaker with an HS-1 "Jiffy Mixer" cage paddle connected to the motor in different waters (tap water from the City of Naperville, Ill.; synthetic sea water; high TDS brine) at different temperatures (4° C., 22° C., 60° C.) at the concentrations indicated in the examples unless otherwise noted. All tests were run at a stir speed of 400 rpm. The water temperature was controlled with a circulating heating/cooling bath through the jacketed beaker. When the water temperature reached the target test temperature, the latex was shot into the stirred water from a disposable syringe and the torque was continuously recorded for 30 minutes and data was worked-up in Microsoft Excel using a 20-period moving average. The analysis was run for 30 minutes to confirm the torque remained stable.

Data: Four pieces of data are determined by Torque measurements: time differential between when the latex was injected and the torque began to increase ("Induction Period"), time until the maximum torque was reached ("Hydration Period"), the value of the maximum torque, and the percent inversion at 2 minutes and 5 minutes (estimated from 2 and 5 minute torque readings compared to the final torque readings).

Plots of torque versus time provide a way to evaluate the speed at which inversion takes place, and also the extent of inversion. The slope of the torque versus time curve in the early portion of the experiment is a good indicator of how rapidly inversion occurs. The torque typically levels off to form a plateau region. Higher levels of torque in the plateau region generally indicate a higher emulsion viscosity.

Relative performance of different surfactants for inversion was assessed by the induction time, hydration time, and torque values in the plateau region. Shorter hydration period as well as higher level of torque in the plateau region indicates better performance of inverting surfactant.

Example 3: Evaluation of Surfactants for Inversion of Anionic Inversion Emulsion (Mobility Control, EOR) Polymers in Synthetic Sea Water at Different Temperatures Un-activated 7:3 acrylamide/acrylic acid emulsion co-polymer (emulsion polymer 1) without activating surfactant was used in this example.

Example 3A: Performance Evaluation in Synthetic Sea Water at 22° C.

Blend preparation and activator concentration: Polymer 1 blends with 2.0% activator were prepared by blending activator into the emulsion while stirring at room temperature.

Conditions: The synthetic seawater (SSW) in the torque monitor apparatus contained 3.5% salts with an equivalent hardness of 6600 ppm of CaCO3 and was maintained at 25° C. An amount of the invertible latex injected into the stirred water in the torque monitor apparatus yielded a dilute latex having 1% polymer.

Figure 3:
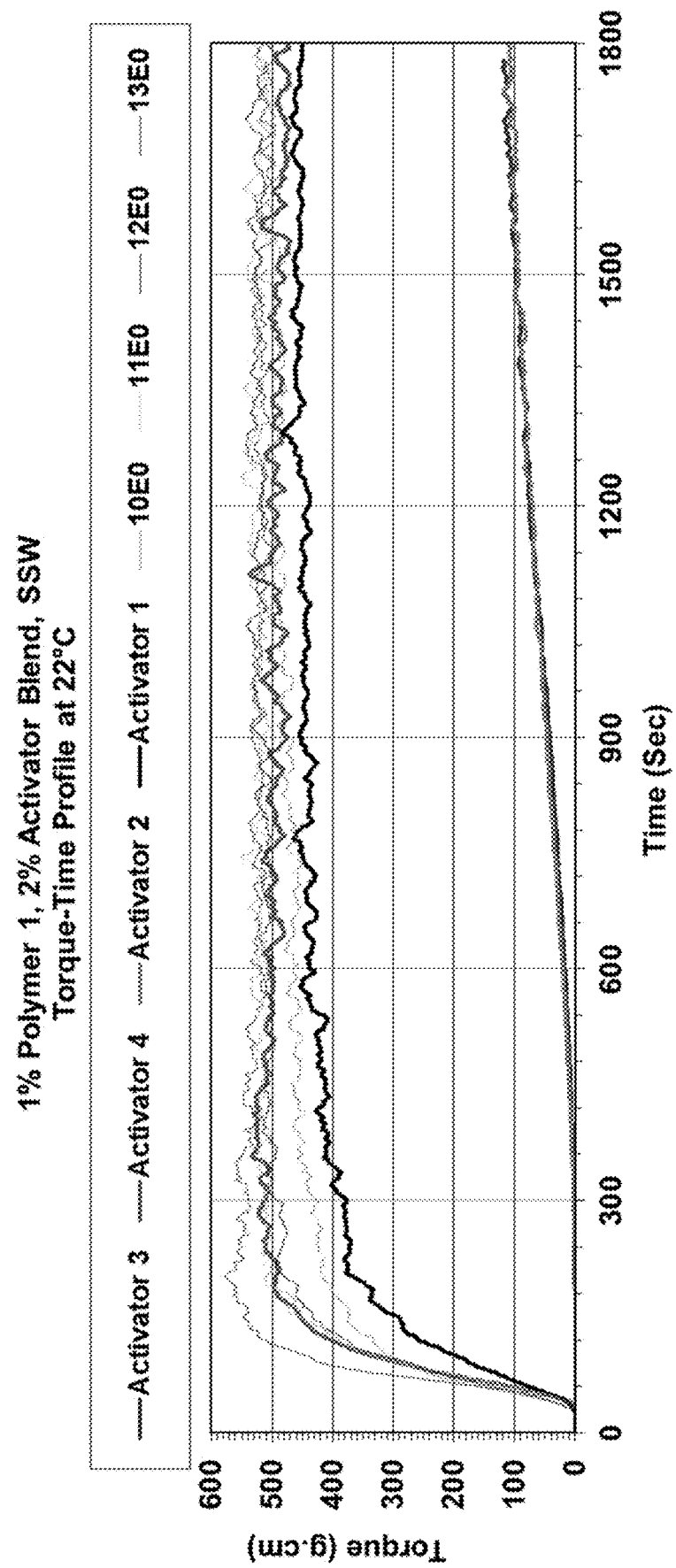
FIG. 3 is a graph of the torque versus time for various activators and activator blends as described in Example 3A.

Results: FIG. 3 depicts the inversion torque profiles at 22° C. for polymer 1 (1% invert in SSW) blends with 2.0% activating surfactants. Table 5 shows induction period, hydration time and maximum torque values (in the plateau region) determined from torque experiments for polymer 1 blends.

Discussion: The data of Table 5 and FIG. 3 demonstrate that, at 22° C., the blends of polymer 1 comprising 2 wt % of a surfactant exhibit faster or comparable inversion rates (as indicated by hydration time) and greater or comparable extent of inversion (as indicated by maximum torque value) than polymer 1 blends comprising 2 wt % of an alcohol ethoxylate or a NPE ethoxylate surfactant. Alcohol ethoxylates (activator 2 and activator 3) performed poorly as maximum torque in range of 100-120 cm-g was achieved at 1800 seconds for the blends comprising them. Activator 13EO was the best performing surfactant among all tested surfactants.

In all cases, at the end of the test, the dilute latex solutions were observed to be fully dispersed, that is, no residual clumps or aggregates of material were observed.

TABLE 5

| Inversion torque measurements for Polymer 1 blends comprising 2% activators | | | |
| --- | --- | --- | --- |
| Surfactant | Induction period (sec) | Hydration time (sec) | Max Torque (g · cm) |
| 10EO | 30 | 1080 | 525 |
| 11EO | 30 | 360 | 525 |
| 12EO | 30 | 360 | 520 |
| 13EO | 30 | 210 | 520 |
| Activator 1 | 30 | 780 | 450 |
| Activator 2 | 360 | — | 100 |
| Activator 3 | 390 | — | 120 |
| Activator 4 | 30 | 300 | 500 |

Example 3B: Performance Evaluation in Synthetic Sea Water at 4° C.

Blend preparation and activator concentration: Polymer 1 blends with 3.0% activator were prepared by blending activator into the emulsion while stirring at room temperature.

Conditions: The synthetic seawater (SSW) in the torque monitor apparatus contained 3.5% salts with an equivalent hardness of 6600 ppm of CaCO3 and was maintained at 4° C. An amount of the invertible latex injected into the stirred water in the torque monitor apparatus yielded a dilute latex having 1% polymer.

Figure 4:
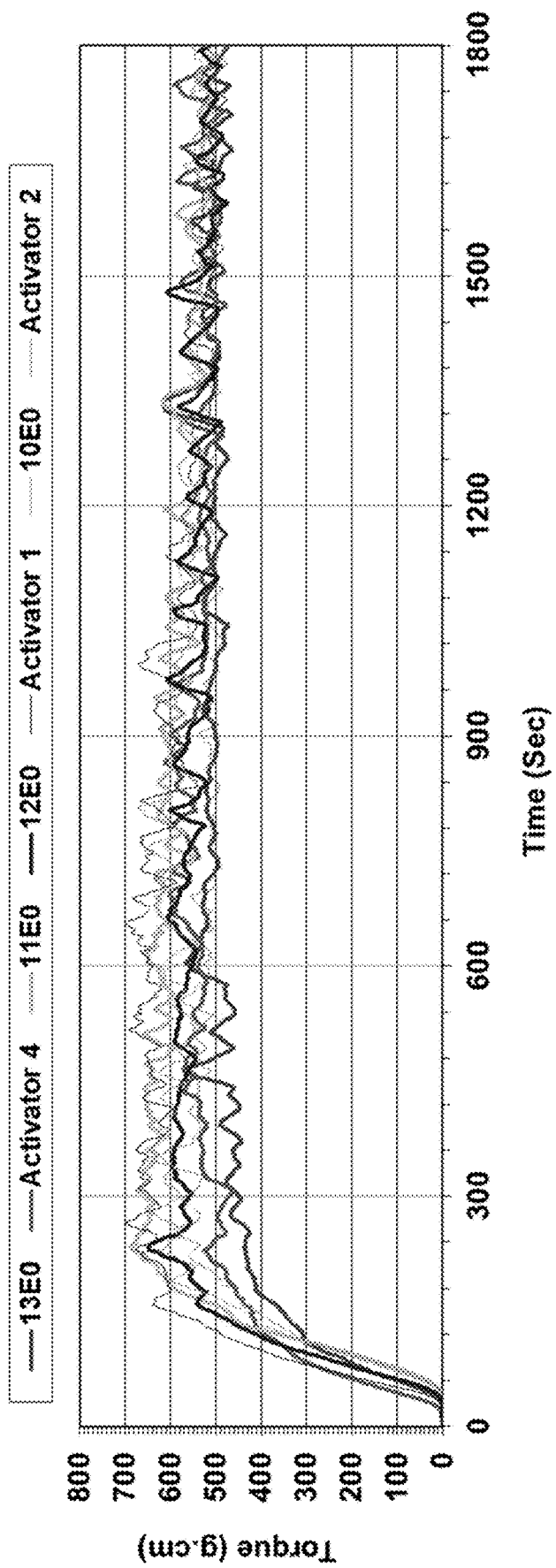
FIG. 4 is a graph of the torque versus time for various activators and activator blends as described in Example 3B.

Results: FIG. 4 depicts the inversion torque profiles at 4° C. for polymer 1 (1% invert in SSW) blends with 3.0% activating surfactants. Table 6 shows induction period, hydration time and maximum torque values (in the plateau region) determined from torque experiments for polymer 1 blends with 3.0% activating surfactants.

Discussion: The data of Table 6 and FIG. 4 demonstrate that, at 4° C., the blends of polymer 1 comprising 3 wt % of a surfactant exhibit faster or comparable inversion rates (as indicated by hydration time) and greater or comparable extent of inversion (as indicated by maximum torque value) than polymer 1 blends comprising 2 wt % of an alcohol ethoxylate or a NPE ethoxylate surfactant. A maximum torque in range of 500-510 cm-g was achieved within 600 seconds for all the blends.

In all cases, at the end of the test, the dilute latex solutions were observed to be fully dispersed, that is, no residual clumps or aggregates of material were observed.

TABLE 6

Inversion Torque Measurements for Polymer
1 blends comprising 3% Activators at 4° C.

| Surfactant | Induction period (sec) | Hydration time (sec) | Max Torque (g · cm) |
|---|---|---|---|
| 10EO | 45 | 240 | 530 |
| 11EO | 45 | 210 | 510 |
| 12EO | 45 | 210 | 510 |
| 13EO | 30 | 600 | 510 |
| Activator 1 | 30 | 240 | 500 |
| Activator 2 | 45 | 240 | 510 |
| Activator 4 | 30 | 420 | 500 |

Example 3C: Performance Evaluation in Synthetic Sea Water at 60° C.

Blend preparation and activator concentration: Polymer 1 blends with 3.0% activator were prepared by blending activator into the emulsion while stirring at room temperature.

Conditions: The synthetic seawater (SSW) in the torque monitor apparatus contained 3.5% salts with an equivalent hardness of 6600 ppm of CaCO3 and was maintained at 60° C. An amount of the invertible latex injected into the stirred water in the torque monitor apparatus yielded a dilute latex having 1% polymer.

Figure 5:
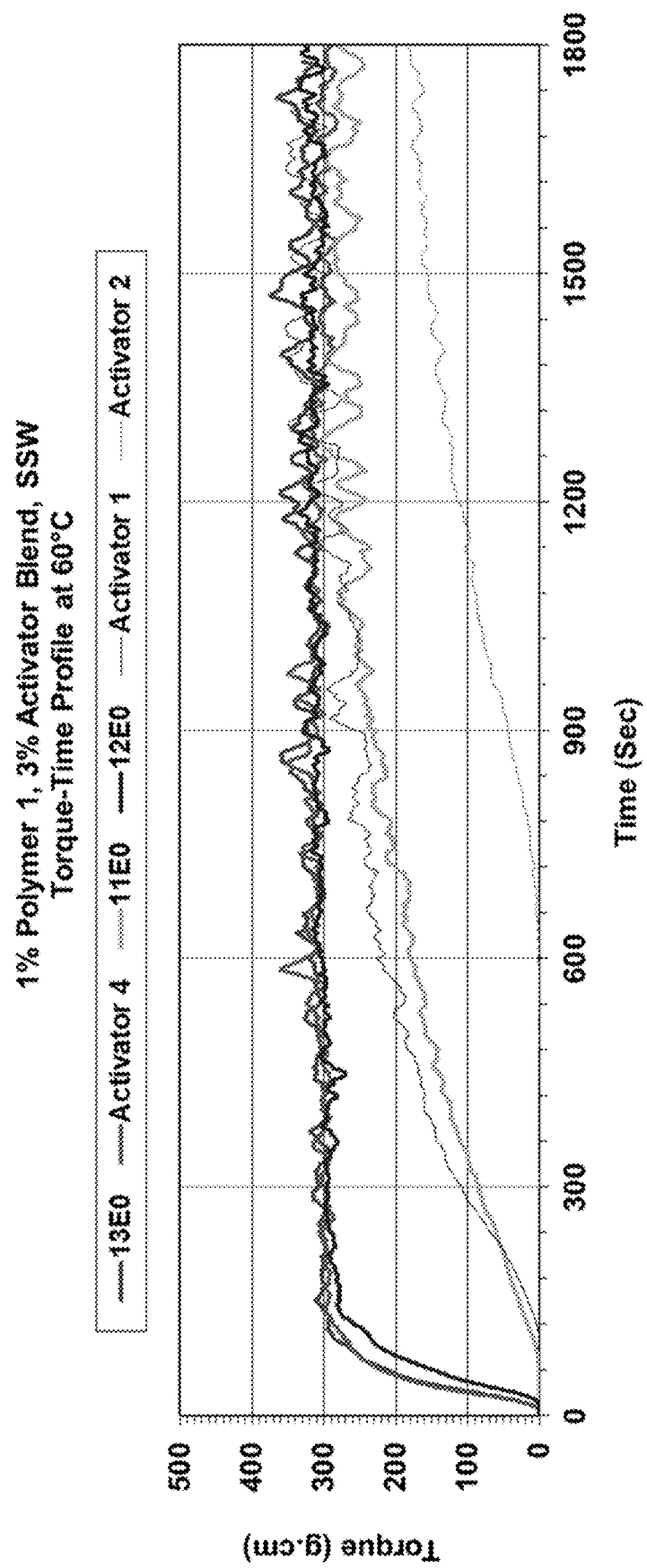
FIG. 5 is a graph of the torque versus time for various activators and activator blends as described in Example 3C.

Results: FIG. 5 depicts the inversion torque profiles at 60° C. for polymer 1 (1% invert in SSW) blends with 3.0% activating surfactants. Table 7 shows induction period, hydration time and maximum torque values (in the plateau region) determined from torque experiments for each polymer 1 blend.

Discussion: The data of Table 7 and FIG. 5 demonstrate that, at 60° C., the blends of polymer 1 comprising 3 wt % of a surfactant exhibit faster inversion rates (as indicated by hydration time) and greater extent of inversion (as indicated by maximum torque value) than polymer 1 blends comprising 3 wt % of an alcohol ethoxylate or a NPE ethoxylate surfactant. Alcohol ethoxylate (activator 2) performed poorly as a maximum torque of about 180 cm-g was achieved at 1800 seconds for the blend comprising it. Activator 13EO was the best performing surfactant among all tested surfactants.

In all cases except for polymer blend 1 comprising 3% activator 2, at the end of the test, the dilute latex solutions were observed to be fully dispersed, that is, no residual clumps or aggregates of material were observed.

TABLE 7

Inversion Torque measurements for Polymer
1 blends comprising 3% activators at 60° C.

| Surfactant | Induction period (sec) | Hydration time (sec) | Max Torque (g · cm) |
|---|---|---|---|
| 11EO | 90 | 1020 | 250 |
| 12EO | 30 | 180 | 310 |
| 13EO | 15 | 120 | 330 |
| Activator 1 | 120 | 1500 | 300 |
| Activator 2 | 690 | 120 | 180 |
| Activator 4 | 15 | — | 320 |

Example 4: Evaluation of Surfactants for Inversion of Anionic Inverse Emulsion (Friction Reducing) Polymers in High TDS Brines Un-activated 8:2 acrylamide/acrylic acid emulsion co-polymer (emulsion Polymer 2) without activating surfactant was used in this example.

Example 4A: Performance Evaluation in 4% KCl Solution at 22° C.

Blend preparation and activator concentration: Polymer 2 blends with 3.0% activator were prepared by blending activator into the emulsion while stirring at room temperature.

Conditions: The water in the torque monitor apparatus contained 4% potassium chloride salts and was maintained at 25° C. An amount of the invertible latex injected into the stirred water in the torque monitor apparatus yielded a dilute latex having 1% polymer.

Figure 6:
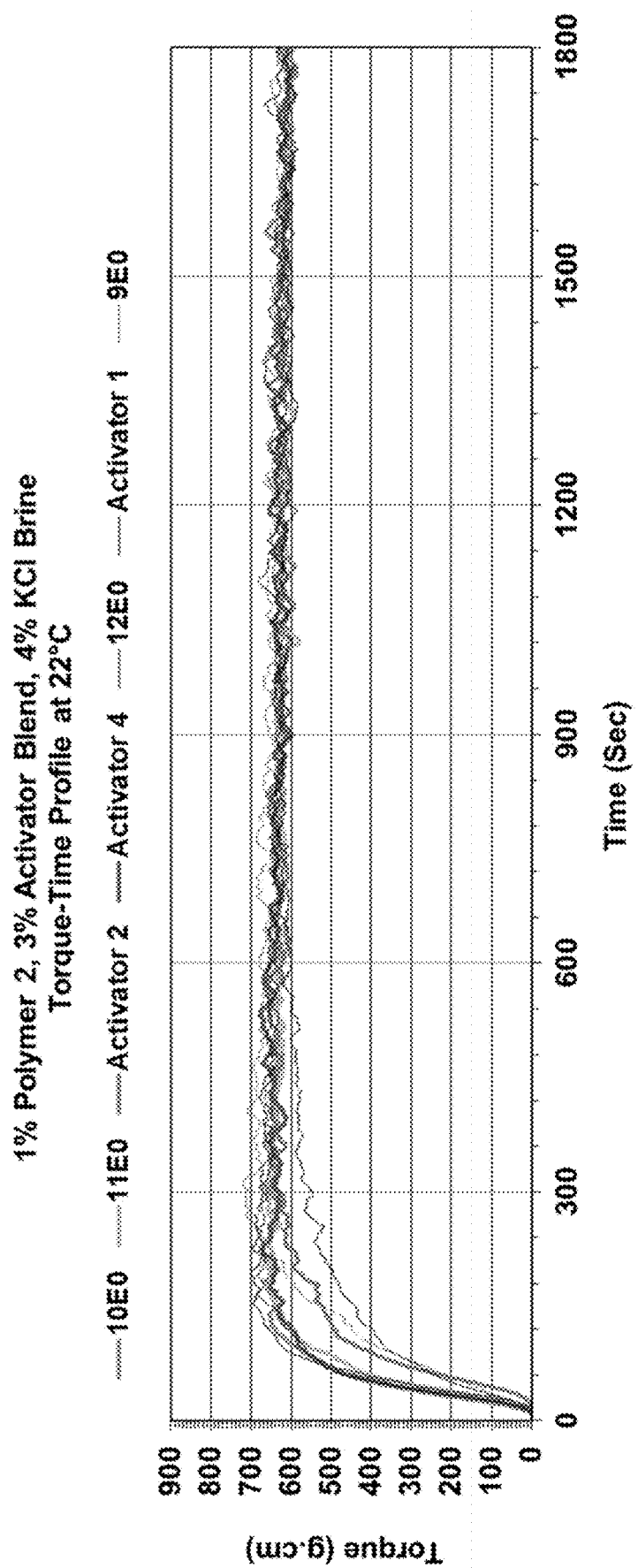
FIG. 6 is a graph of the torque versus time for various activators and activator blends as described in Example 4A.

Results: FIG. 6 depicts the inversion torque profiles at 22° C. for Polymer 2 (1% invert in SSW) blends with 3.0% activating surfactants. Table 8 shows induction period, hydration time and maximum torque values (in the plateau region) determined from torque experiments for polymer 2 blends.

Discussion: The data of Table 8 and FIG. 6 demonstrate that, at 22° C., the blends of Polymer 2 comprising 3 wt % of a surfactant of current invention exhibit faster or comparable inversion rates (as indicated by hydration time) and greater or comparable extent of inversion (as indicated by maximum torque value) than Polymer 1 blends comprising 3 wt. % of an alcohol ethoxylate or a NPE ethoxylate surfactant. A maximum torque in range of 600-620 cm-g was achieved within 150 seconds for all the blends.

In all cases, at the end of the test, the dilute latex solutions were observed to be fully dispersed, that is, no residual clumps or aggregates of material were observed.

TABLE 8

Inversion torque measurements for Polymer 2 blends comprising 3% activators in 4% KCl solution

| Surfactant | Induction period (sec) | Hydration time (sec) | Max Torque (g/cm) |
|---|---|---|---|
| 9EO | 15 | 300 | 640 |
| 10EO | 10 | 120 | 600 |
| 11EO | 15 | 150 | 600 |
| 12EO | 15 | 150 | 610 |
| Activator 1 | 15 | 150 | 630 |
| Activator 2 | 30 | 300 | 620 |
| Activator 4 | 15 | 180 | 600 |

Example 4B: Performance Evaluation in High Stress Conditions Such as TDS (12.5%) Brine Blend preparation and activator concentration: Polymer 2 blends with 3.0% activator were prepared by blending activator into the emulsion while stirring at room temperature.

Conditions: The water in the torque monitor apparatus contained 12.5% salts and was maintained at 22° C. An amount of the invertible latex injected into the stirred water in the torque monitor apparatus yielded a dilute latex having 1% polymer.

Figure 7:
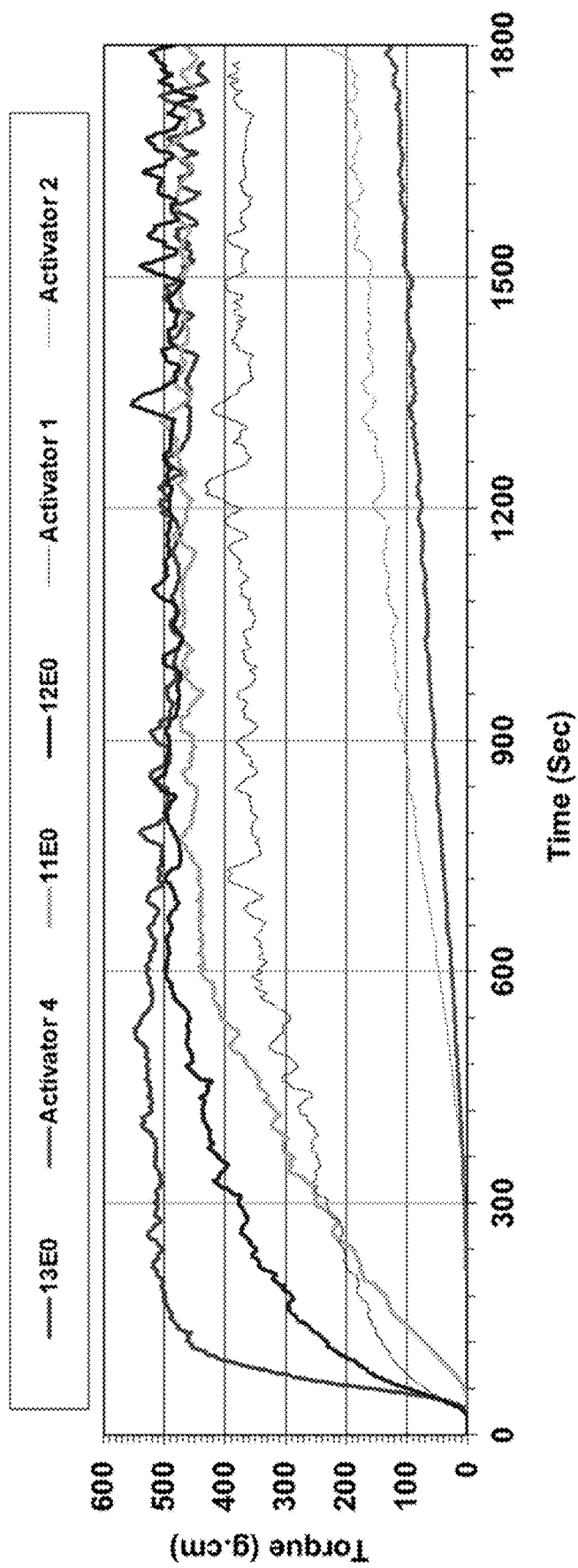
FIG. 7 is a graph of the torque versus time for various activators and activator blends as described in Example 4B.

Results: FIG. 7 depicts the inversion torque profiles at 22° C. for polymer 2 (1% invert in SSW) blends with 3.0% activating surfactants. Table 9 shows induction period, hydration time and maximum torque values (in the plateau region) determined from torque experiments for polymer 2 blends.

Discussion: The data of Table 9 and FIG. 7 demonstrate that, at 22° C., the blends of polymer 2 comprising 3 wt. % of a surfactant exhibit faster inversion rates (as indicated by hydration time) and greater extent of inversion (as indicated by maximum torque value) than polymer 2 blends comprising 3 wt. % of an alcohol ethoxylate or a NPE ethoxylate surfactant under high stress conditions such as high TDS (12.5%) brine. Alcohol ethoxylates (activator 2 and activator 3) performed poorly as a maximum torque in range of 125-900 cm-g was achieved at 1800 seconds for the blends comprising them. Activator 13EO was the best performing surfactant among all tested surfactants. This example demonstrates the superior efficacy of inversion of anionic emulsion polymer 2 compared to other surfactants, especially under high stress conditions such as high TDS.

In all cases except for polymer blend 2 comprising 3% activator 4, at the end of the test, the dilute latex solutions were observed to be fully dispersed, that is, no residual clumps or aggregates of material were observed.

TABLE 9

Inversion torque measurements for Polymer 2 blends comprising 3% activators in high TDS brine.

| Surfactant | Induction period (sec) | Hydration time (sec) | Max Torque (g · cm) |
|---|---|---|---|
| 11EO | 60 | 600 | 450 |
| 12EO | 30 | 540 | 500 |
| 13EO | 30 | 180 | 510 |
| Activator 1 | 30 | 720 | 125 |
| Activator 2 | 300 | — | 380 |
| Activator 4 | 300 | — | 190 |

Example 5: Evaluation of Surfactants for Inversion of Cationic Inverse Emulsion Polymers in Tap Water

Example 5A: Performance Evaluation for Inversion of 50 Mol % Cationic Polymer in Tap Water from the City of Naperville, Ill., at Room Temperature Latex: Un-activated 1:1 Acrylamide/DMAEA•MCQ emulsion co-polymer (emulsion polymer 3) without activating surfactant was used in this example.

Blend preparation and activator concentration: Polymer 3 blends with 1.8% activator were prepared by blending activator into the emulsion while stirring at room temperature.

Conditions: The tap water from the City of Naperville, Ill. was used for torque monitor experiments and was maintained at 22° C. An amount of the invertible latex injected into the stirred water in the torque monitor apparatus yielded a dilute latex having 0.5% polymer.

Figure 8:
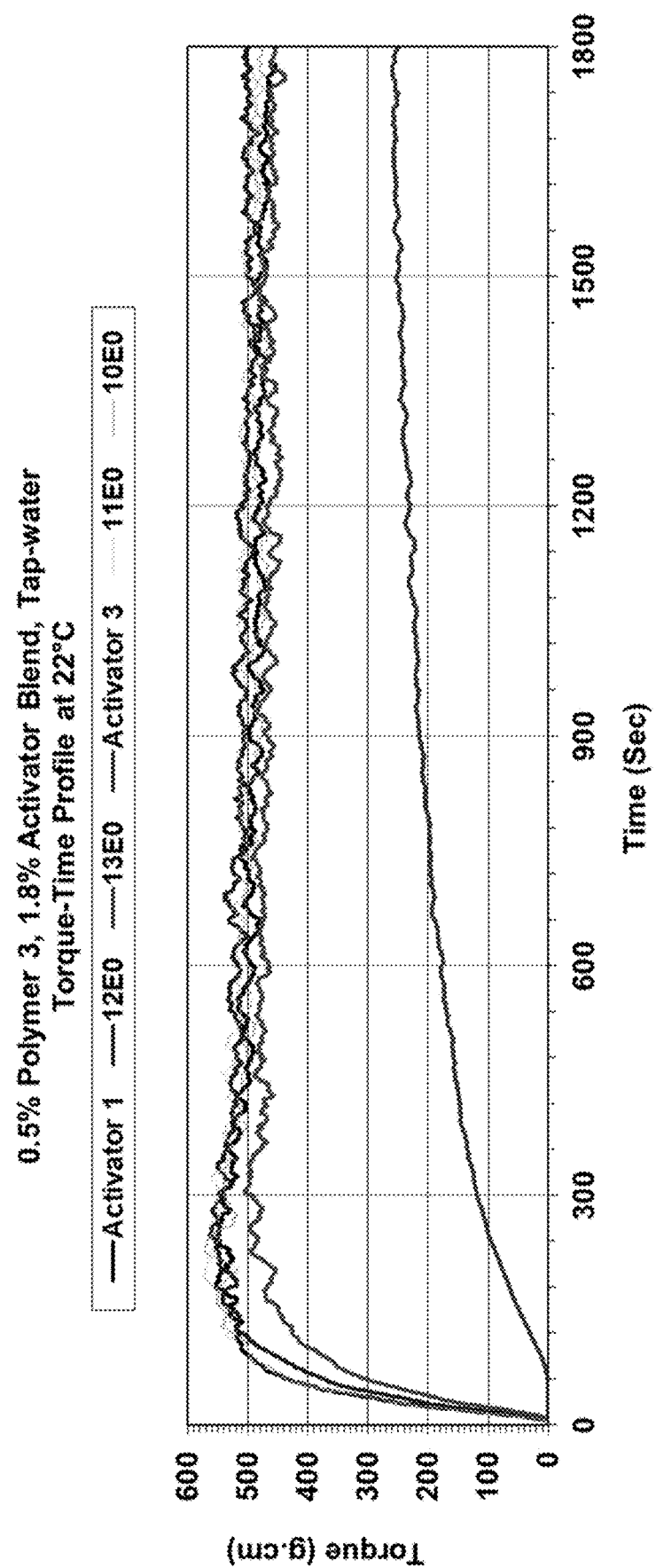
FIG. 8 is a graph of the torque versus time for various activators and activator blends as described in Example 5A.

Results: FIG. 8 depicts the inversion torque profiles at 22° C. for polymer 3 (0.5% invert in SSW) blends with 1.8% activating surfactants. Table 10 shows induction period, hydration time and maximum torque values (in the plateau region) determined from torque experiments for polymer 3 blends.

Discussion: The data of Table 10 and FIG. 8 demonstrate that, at 22° C., the blends of polymer 3 comprising 1.8 wt % of surfactant exhibit faster or comparable inversion rates (as indicated by hydration time) and greater or comparable extent of inversion (as indicated by maximum torque value) than polymer 3 blends comprising 1.8 wt % of an alcohol ethoxylate or a NPE ethoxylate surfactant in tap water. A maximum torque in range of 450-500 cm-g was achieved within 180 seconds for all the blends except for a polymer blend comprising activator 3. Alcohol ethoxylate (activator 3) performed poorly as a maximum torque in range of 250 cm-g was achieved at 1800 second for the blend comprising it. Activators 11EO and 12EO were the best performers among all tested surfactants.

In all cases, at the end of the test, the dilute latex solutions were observed to be fully dispersed, that is, no residual clumps or aggregates of material were observed.

TABLE 10

Inversion torque measurements for Polymer 3 blends comprising 1.8% activators

| Surfactant | Induction period (sec) | Hydration time (sec) | Max Torque (g · cm) |
|---|---|---|---|
| 10EO | 10 | 180 | 470 |
| 11EO | 5 | 120 | 490 |
| 12EO | 5 | 120 | 500 |
| 13EO | 5 | 180 | 460 |
| Activator 1 | 5 | 180 | 450 |
| Activator 3 | 30 | — | 250 |

Example 5B: Performance Evaluation for Inversion of 30 Mol % Cationic Polymer in Tap Water from the City of Naperville, Ill. at Room Temperature Latex: Hard-to-invert un-activated 7:3 acrylamide/DADMAC (polydiallyldimethylammonium chloride) emulsion co-polymer (emulsion polymer 4) without an activating surfactant was used in this example.

Blend preparation and activator concentration: Polymer 4 blends with 2% activator were prepared by blending activator into the emulsion while stirring at room temperature.

Conditions: The tap water from the City of Naperville, Ill. was used for torque monitor experiments and was maintained at 25° C. An amount of the invertible latex injected into the stirred water in the torque monitor apparatus yielded a dilute latex having 1% polymer.

Figure 9:
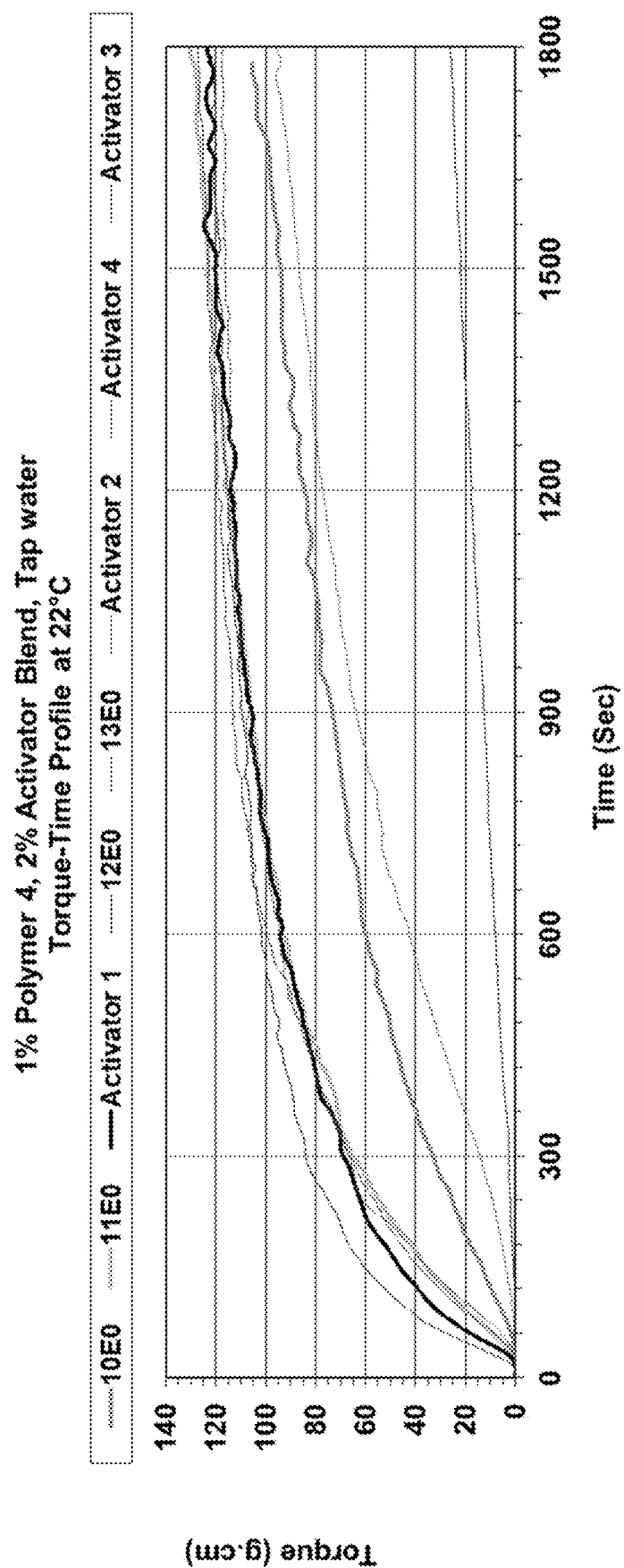
FIG. 9 is a graph of the torque versus time for various activators and activator blends as described in Example 5B.

Results: FIG. 9 depicts the inversion torque profiles at 22° C. for polymer 4 (1% invert in SSW) blends with 2% activating surfactants. Table 11 shows induction period, hydration time and maximum torque values (in the plateau region) determined from torque experiments for polymer 4 blends.

Discussion: The data of Table 11 and FIG. 9 demonstrate that, at 22° C., the blends of polymer 4 comprising 2 wt % of a surfactant have comparable inversion rates (as indicated by inversion % at 2 minutes and 5 minutes) and comparable extent of inversion (as indicated by maximum torque value) than polymer 4 blends comprising 2 wt % of an alcohol ethoxylate or a NPE ethoxylate surfactant in tap water. A maximum torque in range of 120-130 cm-g was achieved at 1800 seconds for the blends comprising surfactants. Alcohol ethoxylate (activator 3) performed poorly as a maximum torque of 30 cm-g was achieved at 1800 second for the blend comprising it. Activator 12EO was the best performer among all tested surfactants.

In all cases, at the end of the test, the dilute latex solutions were observed to be fully dispersed, that is, no residual clumps or aggregates of material were observed.

TABLE 11

% Inversion and maximum torque for Polymer 4 blends with 2% activators

| Surfactant | Surfactant (%) | Inversion % (2 min) | Inversion % (5 min) | Max Torque (g · cm) |
|---|---|---|---|---|
| 10EO | 2.0 | 13.0 | 40.1 | 100 |
| 11EO | 2.0 | 26.0 | 57.2 | 130 |
| 12EO | 2.0 | 47.8 | 73.0 | 120 |
| 13EO | 2.0 | 25.3 | 56.9 | 130 |
| Activator 1 | 2.0 | 36.6 | 61.8 | 130 |
| Activator 3 | 2.0 | 2.5 | 15.0 | 30 |
| Activator 2 | 2.0 | 3.8 | 19.5 | 100 |
| Activator 4 | 2.0 | 29.2 | 59.5 | 120 |

Example 6: Evaluation of Surfactants for Inversion of Non-Ionic Inverse Emulsion Polymer in Tap Water Latex: An un-activated polyacrylamide emulsion polymer (emulsion polymer 5) without activating surfactant was used in this example.

Blend preparation and activator concentration: Polymer 5 blends with 2% activator were prepared by blending activator into the emulsion while stirring at room temperature.

Conditions: The tap water from the City of Naperville, Ill. was used for torque monitor experiments and was maintained at 22° C. An amount of the invertible latex injected into the stirred water in the torque monitor apparatus yielded a dilute latex having 0.5% polymer.

Figure 10:
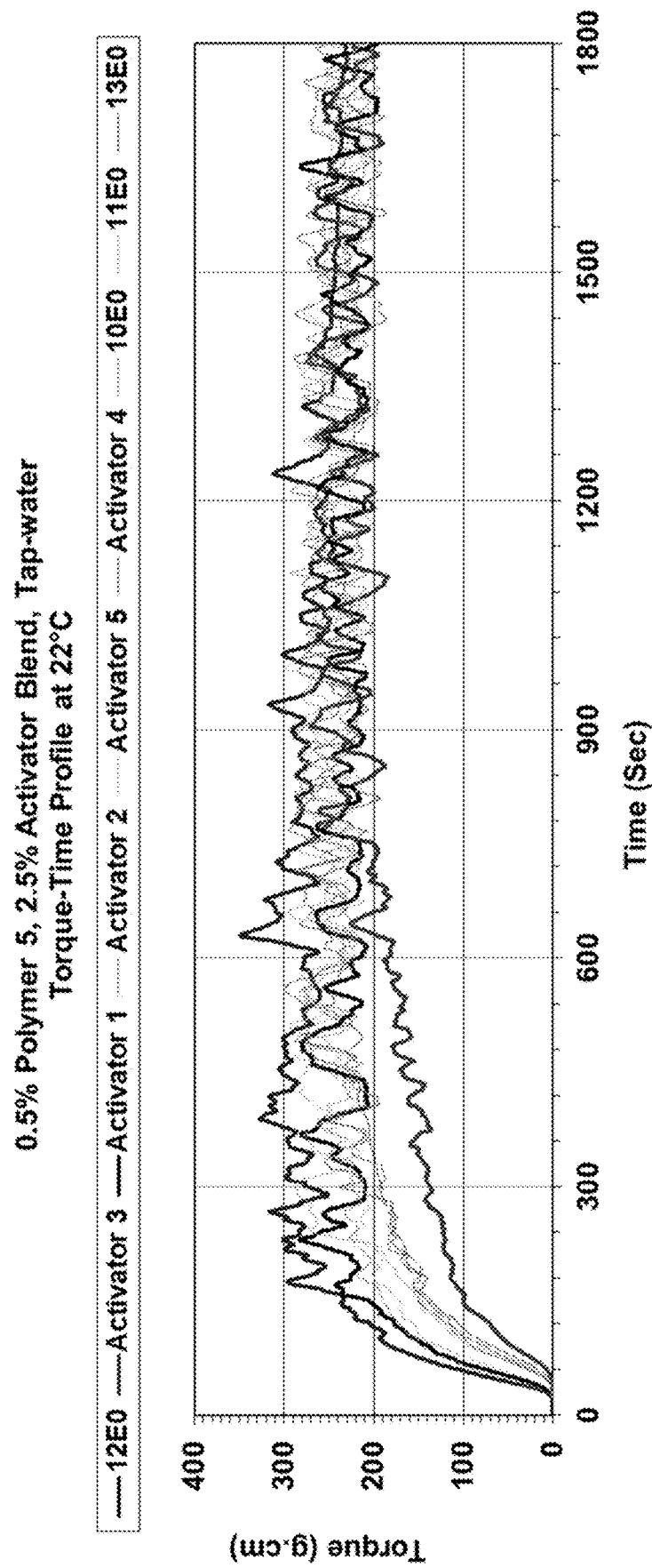
FIG. 10 is a graph of the torque versus time for various activators and activator blends as described in Example 6.

Results: FIG. 10 depicts the inversion torque profiles at 25° C. for polymer 5 (1% invert in SSW) blends with 2% activating surfactants. Table 12 shows induction period, hydration time and maximum torque values (in the plateau region) determined from torque experiments for polymer 5 blends.

Discussion: The data of Table 12 and FIG. 10 demonstrate that, at 22° C., the blends of polymer 5 comprising 2 wt. % of a surfactant comparable or faster inversion rates (as indicated by inversion % at 2 min and 5 min) and comparable extent of inversion (as indicated by maximum torque value) than polymer 5 blends comprising 2 wt. % of an alcohol ethoxylate or a NPE ethoxylate surfactant in tap water. A maximum torque in range of 230-230 cm-g was achieved within 700 seconds for the blends comprising surfactants. Activator 12EO and activator 1 were the best performers among all tested surfactants.

In all cases, at the end of the test, the dilute latex solutions were observed to be fully dispersed, that is, no residual clumps or aggregates of material were observed.

TABLE 12

% Inversion and maximum torque for Polymer 5 blends with 2% activators

| Surfactant | Inversion % @2 min | Inversion % @5 min | Induction period (sec) | Hydration time (sec) | Max Torque (g/cm) |
|---|---|---|---|---|---|
| 10EO | 48.3 | 79.6 | 30 | 360 | 210 |
| 11EO | 58.6 | 83.9 | 30 | 300 | 200 |
| 12EO | 79.9 | 99.1 | 30 | 240 | 230 |
| 13EO | 64.5 | 100.0 | 50 | 540 | 230 |
| Activator 1 | 90.0 | 100.0 | 30 | 180 | 250 |
| Activator 2 | 43.9 | 75.6 | 45 | 300 | 200 |
| Activator 3 | 73.3 | 82.0 | 50 | 740 | 220 |
| Activator 4 | 38.4 | 78.3 | 45 | 540 | 220 |
| Activator 5 | 48.7 | 78.9 | 50 | 420 | 230 |

Example 7: Physical Properties of Novel Surfactants

In this example, the interfacial tension, cloud point and critical micelle concentration was determined for a series of ethoxylate surfactants (1-((2-ethylhexyl)oxy)-3-phenoxypropan-2-ol ethoxylate) having 6 to 13 moles of EO groups.

| 1-((2-ethylhexyl)oxy)-3-phenoxypropan-2-ol ethoxylate | nEO, where n indicates moles of EO units | Surfactants (Prepared as in Examples 1A and 1B) |
|---|---|---|

The interfacial tension is a surface free energy of the interface between two immiscible liquids (in this case, oil and water). Addition of surfactants reduces the interfacial tension. To achieve low interfacial tension, the surfactant partitions equally between two phases and the surfactant has a low affinity for both phases.

The interfacial tension between aqueous surfactant solution at 1% and corn oil was measured using a spinning drop Tensiometer at 4000 rpm. The temperature was kept constant at 25° C. This value is actually dependent on temperature. The minimum interfacial value of different surfactants can be different depending on the temperature and oil phase chosen.

The interphase tension for the ethoxylate surfactants measured using corn oil or dodecane as the light phase are described in Table 13.

TABLE 13

| | Interphase tension | |
|---|---|---|
| Surfactant ID | Interfacial tension (mN/m) (25° C., light phase = corn oil, 4000 rpm) | Interfacial tension (mN/m) (25° C., light phase = dodecane, 4000 rpm) |
| 6EO | 0.49 | 0.13 |
| 7EO | 0.35 | 0.10 |
| 8EO | 0.57 | 0.25 |
| 9EO | 0.68 | 0.40 |
| 10EO | 0.84 | 0.56 |
| 11EO | 1.07 | 0.89 |
| 12EO | 1.26 | 1.03 |
| 13EO | 1.63 | 1.65 |
| NPE 9.5 | 0.837 | 0.40 |

The cloud point is the temperature at which the solution of a nonionic surfactant turns cloudy. At this point, the solution has crossed a phase boundary and the cloudy solution is an emulsion of a coacervate phase in a dilute phase.

The surfactant solution at 1 wt. % was heated slowly with stirring to ensure consistent temperature throughout. The temperature at which the solution started to turn cloudy was taken as a cloud point and depicted in Table 14 for the series of ethoxylate surfactants.

TABLE 14

| | Cloud points |
|---|---|
| Surfactant ID | Cloud Point (° C.) (+/−1 C.) |
| 6EO | <1 |
| 7EO | 1.0 |
| 8EO | 12.5 |
| 9EO | 27.0 |
| 10EO | 37.5 |
| 11EO | 48.0 |
| 12EO | 58.5 |
| 13EO | 77.5 |
| NP9.5 | 53.0 |

The critical micelle concentration (CMC) is a concentration at which a micelle starts to form in a solution having a surfactant. It can be measured through several physical property measurements. Here, it was determined by measuring the surface tension of a surfactant solution at various concentrations. A semi log plot of concentration-surface temperature yielded a curve with a break or change in slope. At the break, the concentration was taken as the critical micelle concentration (CMC). Table 15 summarizes the critical micelle concentration for each of the ethoxylate surfactants tested.

TABLE 15

| | Critical Micelle Concentrations |
|---|---|
| Surfactant ID | CMC (ppm) |
| 6EO | 72.45 |
| 7EO | 110.84 |
| 8EO | 129.02 |
| 9EO | 152.75 |
| 10EO | 167.80 |
| 11EO | 227.52 |
| 12EO | 350.73 |
| 13EO | 451.00 |

Additional surfactants were prepared (example 2A and 2B) and tested giving the following results. In this example, cloud point and critical micelle concentration was determined for a series of ethoxylate surfactants (3,3'-((4-hydroxyphenyl)azanediyl)bis(1-((2-ethylhexyl)oxy)propan-2-ol) ethoxylate) having 10 to 24 moles of EO groups.

| 3,3'-((4-hydroxyphenyl)azanediyl)bis(1-((2-ethylhexyl)oxy)propan-2-ol) ethoxylate | N-nEO, where n indicates moles of EO units (n is the sum of the o, p, and q integers) | Surfactants (Prepared as in Examples 2A and 2B) |
|---|---|---|

TABLE

| Surfactant | Concentration (ppm) | Cloud Point (° F.) | CMC (ppm) |
|---|---|---|---|
| N-10EO | 10,001 | <36 | — |
| N-12EO | 10,100 | <36 | — |
| N-14EO | 9,900 | <36 | — |
| N-16EO | 10,059 | 44 | — |
| N-18EO | 9,898 | 68 | — |
| N-20EO | 10,289 | 90 | 32 |
| N-22EO | 10,001 | 106 | 37 |
| N-24EO | 9,999 | 124 | 42 |

Example 8: Non-APE Surfactants Demonstrate Good Soil Removal from Premade Fabric Swatches In this example, an alkaline detergent builder alone or in combination with the novel surfactants disclosed herein were subjected to a standard Tergotometer test procedure to measure soil removal from premade fabric swatches (polyester or cotton). The test measured the ability of each detergent-surfactant combination to remove makeup from cotton, or lipstick from cotton or polyester. Table 16 describes the identity of the surfactants (1-((2-ethylhexyl)oxy)-3-phenoxypropan-2-ol ethoxylates) tested in this example.

TABLE 16

| Surfactant | moles of EO ("n") |
|---|---|
| Surfactant 1 | 7 |
| Surfactant 2 | 8 |
| Surfactant 3 | 9 |
| Surfactant 4 | 10 |
| Surfactant 5 | 12 |

Premade polyester and cotton swatches purchased from Test Fabrics, Inc. were stamped with lipstick and/or make-up using a standardized method designed to reduce variability in lipstick application to allow for repeatable and consistent cleaning testing. Briefly, the stamping procedure involved: coating the stamp in lipstick (Cover Girl #435 and Tom Ford "Indian Rose" used) using an applicator and then dragging a clean edge, such as the edge of a stainless steel curtain across the stamp with the direction of the ridges. Ideally, the stamp was fully coated in lipstick with ridges remaining visible. The fabric swatches were stamped, using the same quantity of pressure for each swatch. The stamp was lifted lightly to allow the freshly stamped soil to be undisturbed.

Premade fluid make up on cotton swatches (code #C-S-17) were purchased from the Center for Testmaterials B.V.

Soiled fabric swatches were then subjected to a standard Tergotometer test to measure effectiveness of detergent/surfactant combinations at removing the soil. A tergotometer Model #7243ES, Serial MCC 14-813 from Test Fabrics Inc was used along with 1 L pots and a water bath. Before washing, the initial values of the soiled swatches were read on the HunterLab COLOR QUEST Spectrophotometer to establish the initial "L" value. The tergotometer was set for 120° F. and one liter of 5 grain water added to each of the six pots and allowed to equilabrate to 120° F.

The laundry solutions were weighed out and added to the tergotometer pots and agitated for 30 seconds to 1 minutes to mix and dissolve. The controller was set for a 1 minute run time, with an RPM of 100 (standard RPM for most tests). Each swatch was added quickly in order to minimize differences in exposure time to the detergent systems. Each swatch was agitated for 10 minute immediately after adding swatches and then removed and transferred to 1 L of cold 5 grain water to rinse. The swatches were then removed from the cold water and further rinsed under cold 5 grain tap water. Excess moisture was removed by squeezing and the swatches were air dried on a Wypall paper towel. After drying, the spectrophotometer (HunterLab COLOR QUEST) was used to measure the final "L" value. The % soil removal was calculated from the difference between the initial (before washing) L value and the final L value (after washing).

Table 17 describes the % soil removed from each of the following combinations: 1300 ppm Builder C (standard alkaline detergent builder), Builder C+NPE 9.5 (450 ppm), or 1300 ppm Builder C with Surfactants 1-5 (450 ppm). NPE 9.5 is Nonylphenol with 9.5 moles of ethylene oxide.

Example 9: Non-APE Surfactant Combinations Effective in Removing Lipstick from Homemade Swatches The ability of the same detergent/surfactant compositions used in Example 8 to remove lipstick stains from homemade polyester swatches was tested in a similar way to Example 8. Major differences are described below.

Lipstick (Tom Ford "Indian Rose") was applied (stamped) onto each homemade polyester fabric swatches as described in Example 8. Washing was done using the Tergetometer of Example 8 but the amount of pigment removed from each swatch (% removal) was determined using ImageJ software analyzing scanned images for the swatches before ($A_1$) and after washing (A2). Each image was processed to remove background (using a white piece of paper as background) before quantification. A rectangle was drawn on each image to contain the stamped lipstick (the same area size was used in all measurements). The % area was then measured inside this rectangle and used to determine the % pigment removal using the following equation.

$$\% \text{ Removed} = \frac{A_1 - A_2}{A_1} \times 100,$$

where $A_1$ is the percent area before washing and $A_2$ is the percent area after washing.

Table 17 shows the results of soil removal from homemade swatches in this experiment. Each detergent/surfactant combination performed equally or superiorly to a control NPE surfactant.

TABLE 17

| Chemistry | % soil removal | St Dev |
| --- | --- | --- |
| 1300 ppm Builder C | 8.11 | 4.11 |
| 1300 ppm Builder C 450 ppm NPE 9.5 | 85.78 | 4.61 |
| 1300 ppm Builder C 450 ppm Surfactant 2 | 61.48 | 1.45 |
| 1300 ppm Builder C 450 ppm Surfactant 3 | 92.89 | 1.14 |
| 1300 ppm Builder C 450 ppm Surfactant 4 | 89.87 | 1.86 |

TABLE 17

| Detergent Combination | Makeup-Cotton (% Removal) | ST DEV | Lipstick-Cotton (% Removal) | ST DEV | Lipstick-Polyester (% Removal) | ST DEV |
| --- | --- | --- | --- | --- | --- | --- |
| 1300 ppm Builder C | 22.16 | 1.85 | 34.86 | 1.84 | 17.00 | 1.01 |
| 1300 ppm Builder C, 450 ppm NPE 9.5 | 44.20 | 2.80 | 53.29 | 1.23 | 64.91 | 0.59 |
| 1300 ppm Builder C, 450 ppm Surfactant 1 | 37.70 | 2.84 | 47.77 | 0.32 | 45.09 | 0.70 |
| 1300 ppm Builder C, 450 ppm Surfactant 2 | 36.12 | 2.30 | 50.51 | 2.25 | 63.34 | 0.55 |
| 1300 ppm Builder C, 450 ppm Surfactant 3 | 42.61 | 1.86 | 52.01 | 0.94 | 66.43 | 0.30 |
| 1300 ppm Builder C, 450 ppm Surfactant 4 | 42.18 | 1.65 | 53.11 | 1.93 | 63.78 | 0.86 |
| 1300 ppm Builder C, 450 ppm Surfactant 5 | 46.30 | 2.81 | 50.15 | 3.55 | 52.99 | 0.39 |

Example 10: Inventive Surfactants Effective at Butterfat Removal

A standard butterfat removal test method was used to screen surfactants for their ability to remove butter from a coupon (e.g., stainless steel, PS (Polysulfone), or PVDF (Polyvinylidene fluoride). Typical consumer materials are made of PES (polyethersulfone) or PVDF material. Here, a PS coupon was used to represent the PES membrane surface.

A series of ethoxylated surfactants (6EO to 13EO and N-18EO to N-22EO) were tested alongside deionized (DI) water, Ethyl hexyl alcohol alkoxylate (Ecosurf EH-9), Nonylphenol with 9.5 moles of ethylene oxide (NPE 9.5). Each surfactant was used at a concentration of 200 or 600 ppm except EH-9 (always 1000 ppm).

Brand new, unused, coupons (1×3 in. PS coupons from Small Parts via Amazon) were used for each surfactant tested. Each coupon was soaked in methanol for 30 seconds and allowed to dry, then placed on a cookie sheet (lined with Wypall towels) in a 120° F. oven for 30 minutes. After cleaning and drying, each coupon was weighed on an analytical balance. Then a homogenous layer of room temperature butter (unsalted) was applied to the bottom 75% of each coupon using a 1" wide foam brush. Overall, about 0.0250 to 0.0300 g of butter was applied to each coupon. Then the coupons were placed back on the cookie sheet and allowed to dry overnight before weighing a second time.

600 g of a test solution consisting of one surfactant (200 or 600 ppm, except for EH-9 (always 1000 ppm)) in DI water was prepared and added to a beaker along with a stir bar. The solution was heated to 120° F. (+/−2° F.), stir speed was set to 240 rpm, and NaOH added to bring solution to pH 11. Note, each surfactant was tested in triplicate using three different coupons in three different beakers containing the relevant surfactant solution. Once prepared, the coupons were suspended in the solution at a constant distance between the coupon and the center of the beaker, with the soiled/butter side faced the center. The stir speed was maintained at 240 rpm and the temperature maintained at 120° F. for 10 minutes. Then each coupon was removed and dipped three times into a separate beaker slowly overflowing with DI water (e.g., placed under a running DI faucet). Each "dip" consisted of submerging the coupon under the water for 2 seconds and removing for 2 seconds. The coupons were then placed on a paper towel to dry before returning to the cookie sheet where they dried overnight. The next day, they were weighed again.

Figure 11A:
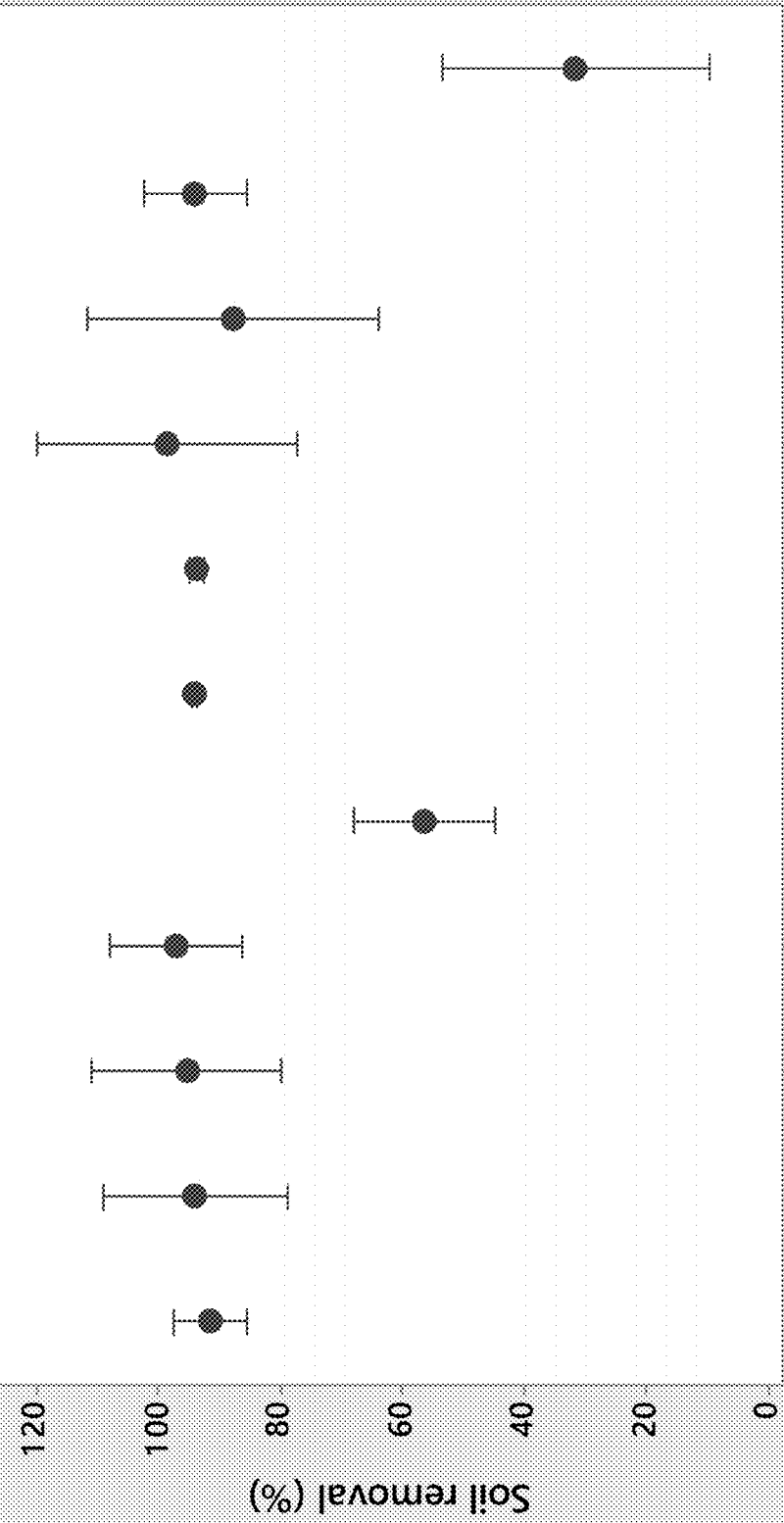
FIGS. 11A, 11B, and 11C are graphs of the % soil removed from coupons for various surfactant compositions as described in Example 10.
Figure 11B:
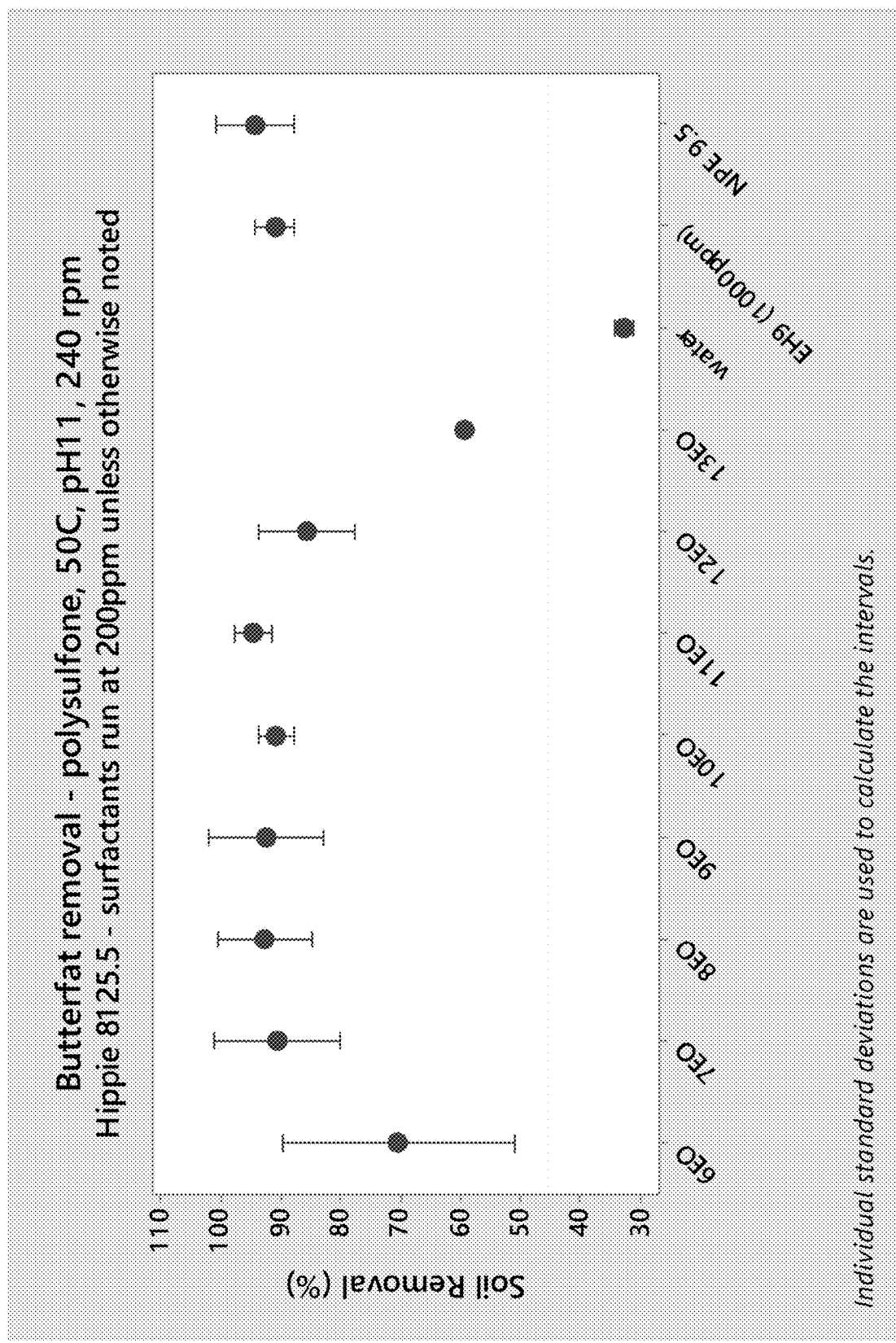
Figure 11C:
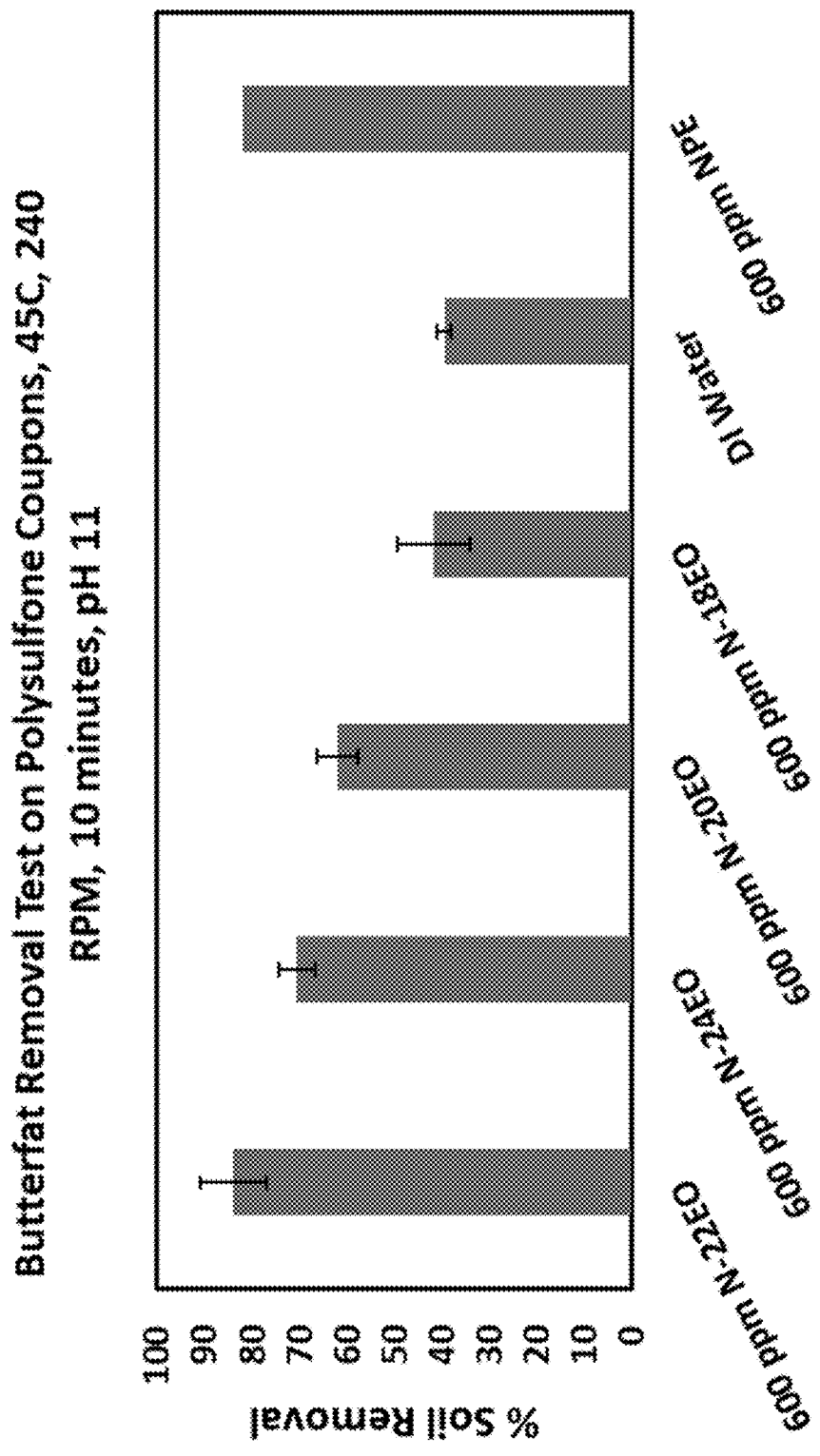

FIGS. 11A, 11B, and 11C show the percent soil removal calculated from the weight of the cleaned coupons compared to the dried soiled coupons for 6EO to 13EO at 600 ppm (FIG. 11A), 6EO to 13EO at 200 ppm (FIG. 11B), and N-18EO to N-22EO at 600 ppm (FIG. 11C). The ethoxylated surfactants (6EO to 13EO) performed well at removing butter residue as compared to water or other standard surfactants (EH9 and NPE 9.5). The ethoxylated surfactants N-18EO to N-22EO performed progressively better at higher moles of EO as compared to water or standard surfactant NPE 9.5.

Example 11: Contact Angle Measurement of Surfactant Solutions

Polysulfone (PS) coupons (size 1"×2") were prepared by removing the plastic film from each side, washed with soap and water and air dried. A series of surfactant solutions was prepared at the following concentrations in DI water: dodecyldimethylamine oxide (DDAO, 500 ppm), NPE 9.5 (500 ppm), 9EO (200 ppm and 600 ppm), and EH-9 (1000 ppm). Each solution was adjusted to a pH of 11 with NaOH.

Figure 12:
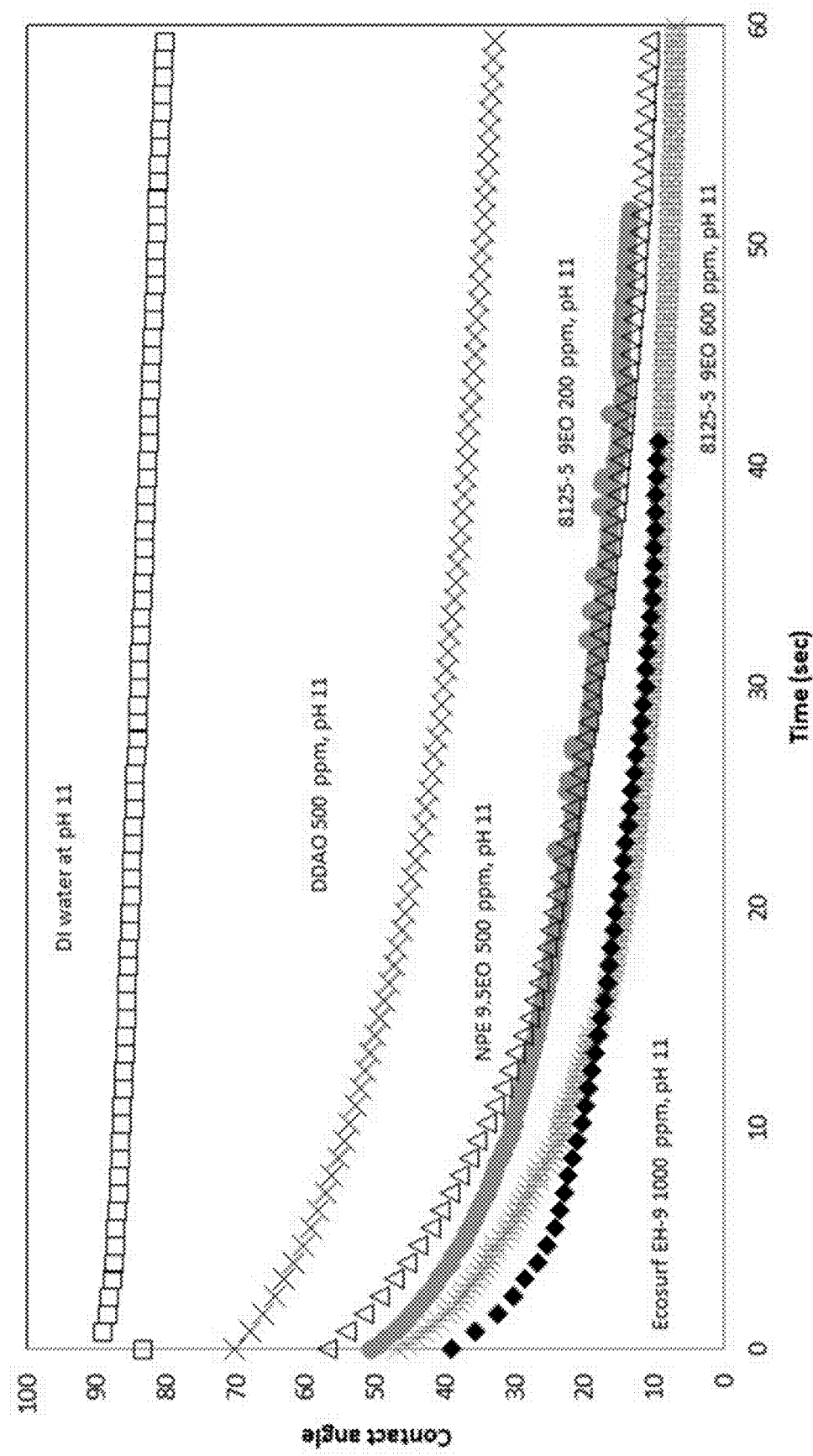
FIG. 12 is a graph plotting the contact angle over time for water droplets with or without the surfactant compositions as described in Example 11.

The contact angle measurement for each solution was determined using an optical Tensiometer (Attension Theta) with a temperature controlled chamber. This machine automates the temperature, recording time, and placement of a droplet (4 μL) onto each coupon. The results for the contact angle measurement for each solution over one minute (60 seconds) are plotted in FIG. 12. Both of the solutions containing the inventive surfactant (9EO at 200 ppm or 600 ppm) performed similarly to control surfactants, NPE 9.5 or Ecosurf EH-9.

Example 12: Inventive Surfactants Effective at Red Soil Removal

A standard red soil removal test method was used to screen surfactants for their ability to remove red soil from a vinyl tile. Red soil mimics typical consumer food soil.

A series of test solutions including either ethoxylated surfactants 9EO to N-24EO or nonylphenol with 9.5 moles of ethylene oxide (NPE 9.5) were tested. The test solutions were 72.1% zeolite softened water, 0.4% phosphoric acid 75% solution, 3.5% isopropyl alcohol, 6% tetrasodium EDTA 40% solution, and either 18% ethoxylated surfactant or 18% NPE 9.5. Additional test solutions were Oasis Pro 16 at 8 oz/gallon (used as a positive control), and water (used as a negative control). Water for controls, solutions, etc. was 5 grain water (i.e. water with 5 grain per gallon) unless otherwise noted.

Vinyl tiles (cut to 3×3 in., manufactured by Flexco) were used for each solution tested. An average background measurement of the blank tiles was taken with a Hunter Mini Scan Colorimeter. Red soil was prepared immediately before use and consisted of 39% lard, 39% corn oil, 20% whole egg powder, and 2% iron III oxide powder. The red soil was prepared at 100° F. by combining the lard and the corn oil and mixing, adding the whole egg powder and mixing, and adding the iron III oxide powder and mixing for 15 minutes. About 0.75 g of red soil was applied to each tile with a foam brush. The soiled tiles were allowed to dry overnight. A colorimeter measurement of was taken of each tile.

Each tile was soaked for 60 seconds in 200 g of test solution. Soil removal testing was conducted with a straight line abrasion machine applying 2.0 lbs pressure through a cellulose sponge soaked with 80 g of test solution. 4 back and forth motions of the sponge were followed by a 90° rotation of the tile. This was repeated 4 times, for a total of 16 back and forth motions. The tiles were gently rinsed with DI water and allowed to dry overnight in a dish rack. 5 measurements, approximately at the center and near each of the 4 corners, were taken per tile and averaged for each tile.

Figure 13:
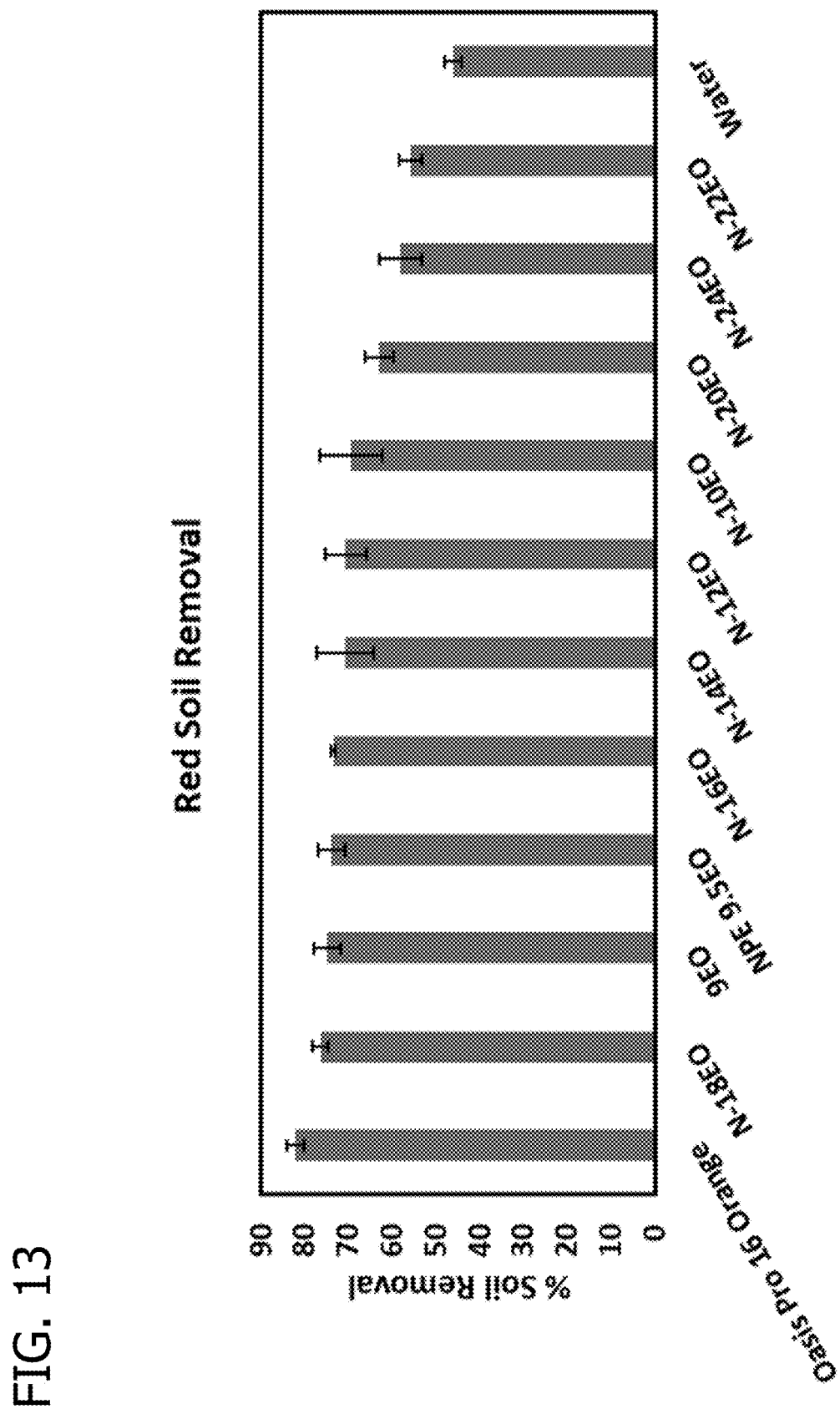
FIG. 13 is a graph of the % soil removed from coupons for various surfactant compositions as described in Example 12.

FIG. 13 shows the percent soil removal calculated from the change in colorimeter readings before and after testing. Ethoxylated surfactants performed better compared to water.

Example 13: Foam Generation Behavior of Inventive Surfactants

A foam generation test was used to screen surfactants for their foam generation behavior. For various surfactant applications, high or low foam generation can be desirable.

A series of solutions including either ethoxylated surfactants (9EO or N-18EO) or nonylphenol with 9.5 moles of ethylene oxide (NPE 9.5) was tested. Each surfactant was used at a concentration of 1000 ppm.

Each test used 250 mL of solution which was equilibrated at the either 20° C., 45° C., or 60° C. For each test, the solution was stirred for 10 seconds at either 950 rpm or 1200 rpm, during which 99 measurements of foam volume were taken with a Sita R2000 Foam Analyzer.

Figure 14A:
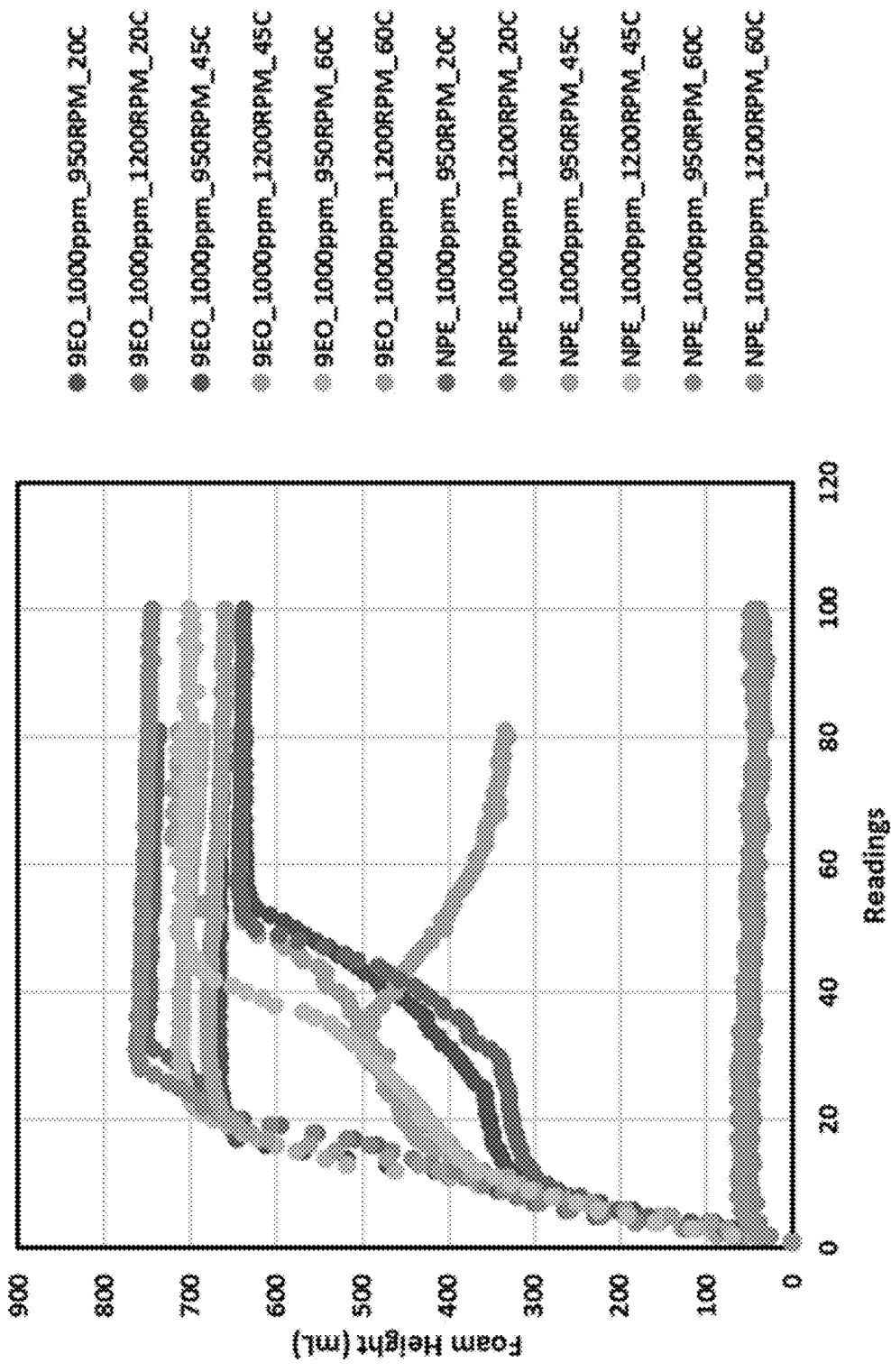
FIGS. 14A and 14B are graphs of the foam height for particular surfactant compositions as described in Example 13.
Figure 14B:
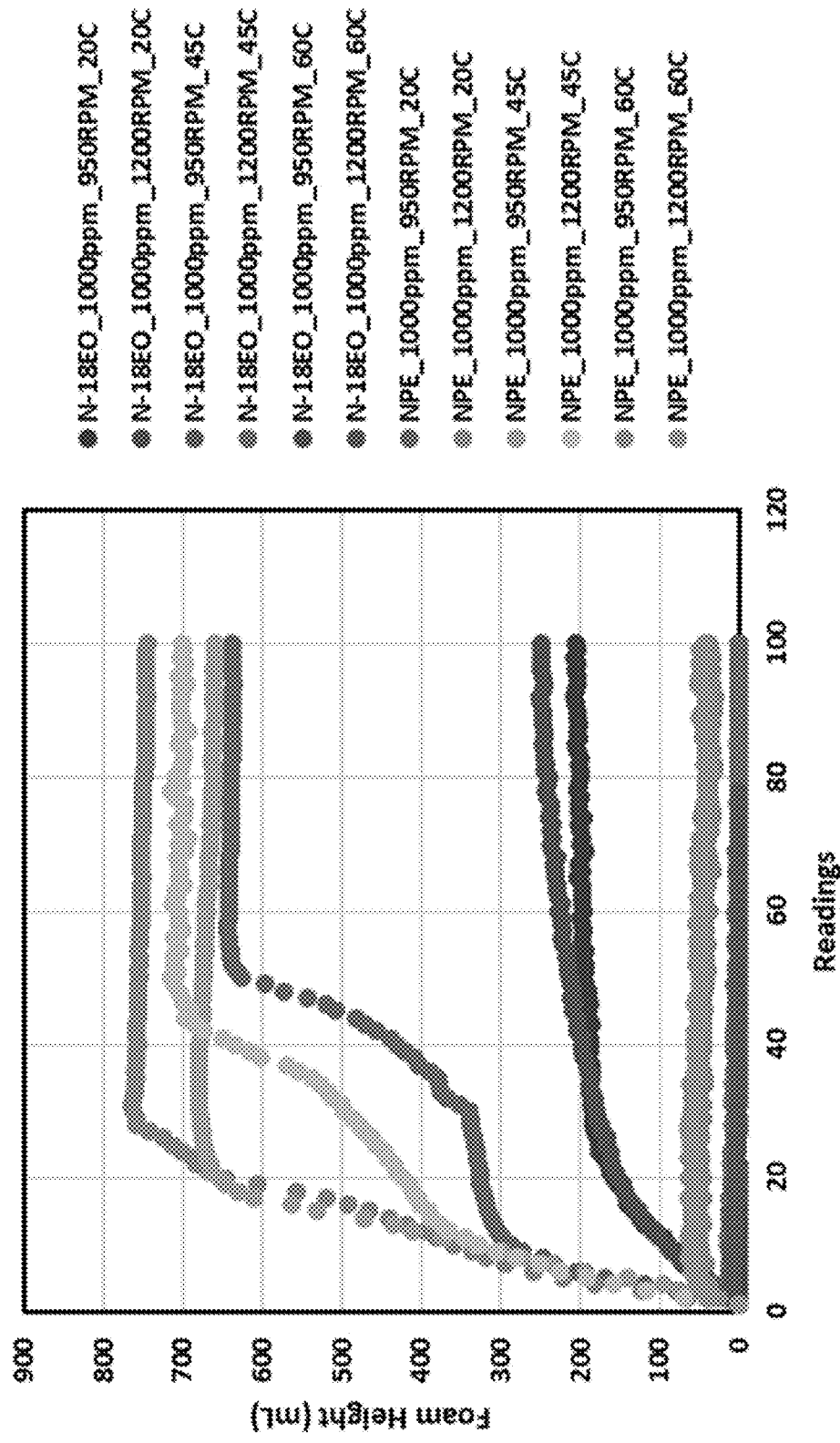

FIG. 14A shows the height of foam created by 9EO in comparison to NPE 9.5 at various temperatures and RPMs Foam generation by N-9EO was high in comparison to NPE 9.5 at 60° C. FIG. 14B shows the height of foam created by N-18EO in comparison to NPE 9.5 at various temperatures and speeds. N-18EO demonstrated foam generation at 20° C. Foam generation by N-18EO was low in comparison to NPE 9.5. For N-18EO, there was little foam generation at 20° C. and almost none at 45° C. and 60° C.

Example 14: Foam Decay Behavior of Inventive Surfactants

A foam decay test was used to screen surfactants for their foam decay behavior. For various surfactant applications, fast or slow foam decay can be desirable.

A series of solutions including either ethoxylated surfactants (9EO or N-18EO) or nonylphenol with 9.5 moles of ethylene oxide (NPE 9.5) was tested. Each surfactant was used at a concentration of 1000 ppm.

Each test used 250 mL of solution which was equilibrated at the either 20° C., 45° C., or 60° C. For each test, the solution was stirred for 10 seconds at either 950 rpm or 1200 rpm to generate foam. Measurements of foam volume were taken with a Sita R2000 Foam Analyzer every 10 seconds for upwards of 15 minutes, or until the foam volume reached 0 mL.

Figure 15A:
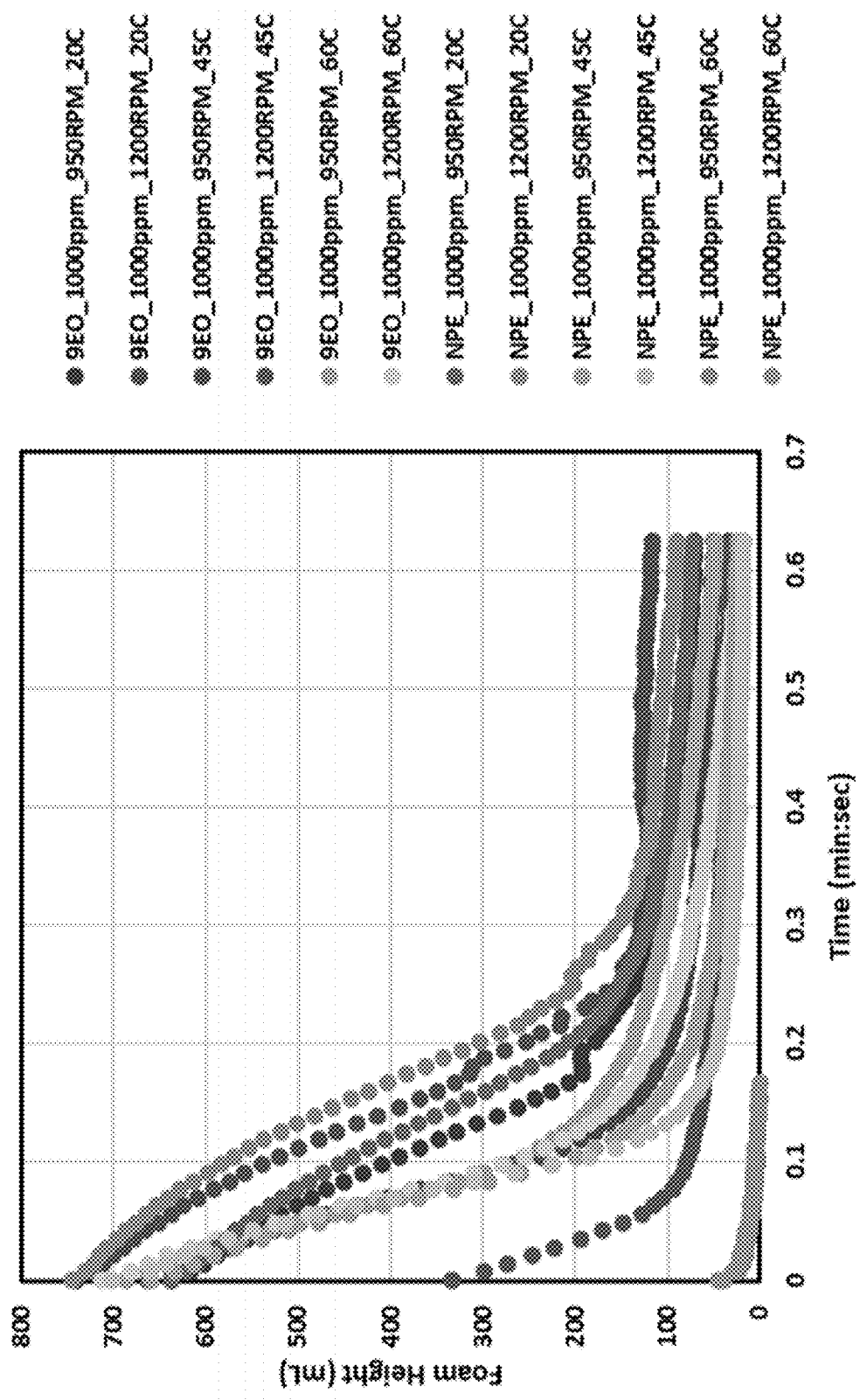
FIGS. 15A and 15B are graphs of the foam height over time for the surfactant compositions as described in Example 14.
Figure 15B:
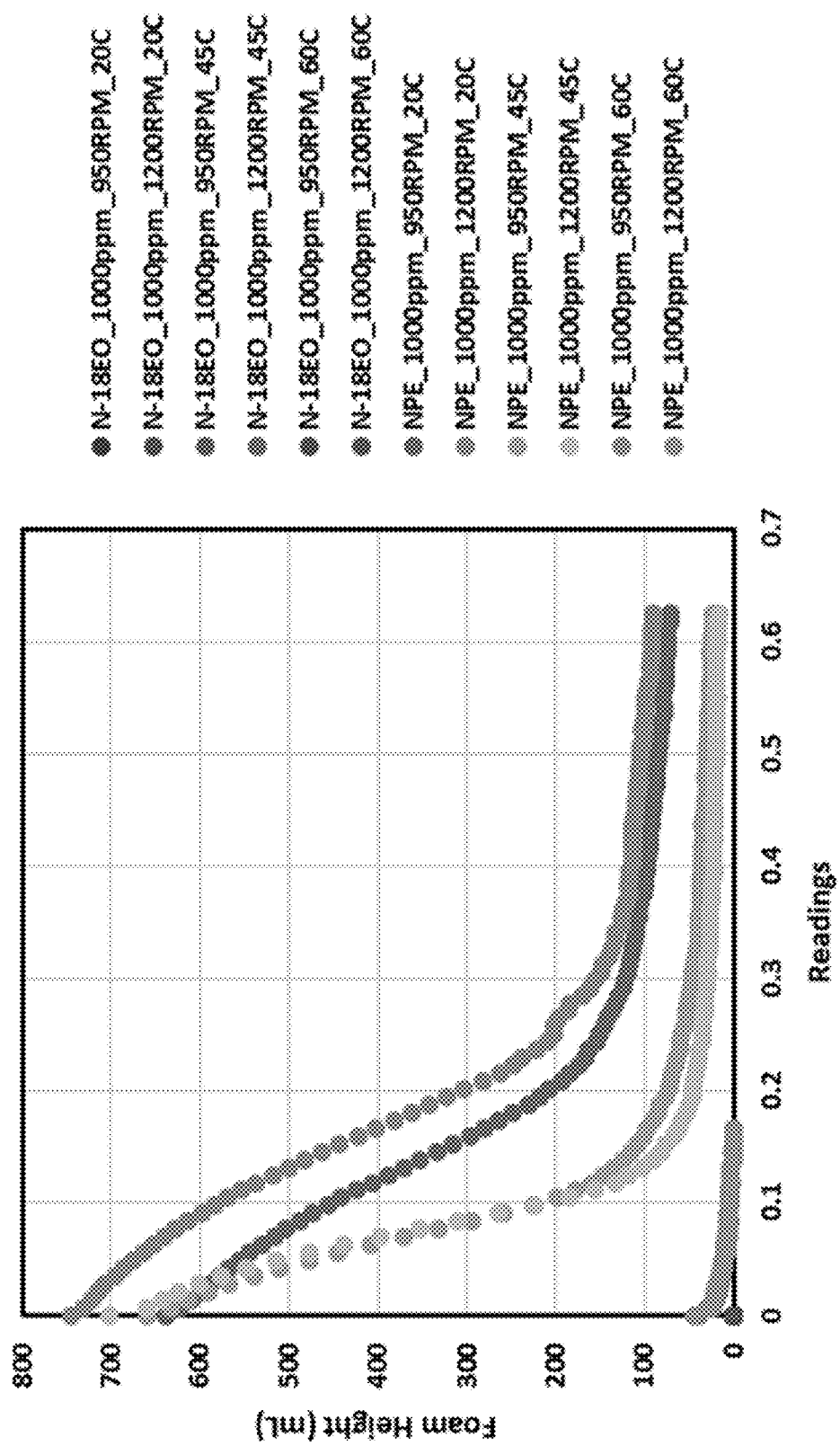

FIG. 15A shows the height of foam created by 9EO in comparison to NPE 9.5 at various temperatures and speeds. FIG. 15B shows the height of foam created by N-18EO in comparison to NPE 9.5 at various temperatures and speeds. Foam decay of N-18EO and 9EO solutions was fast and similar to that of NPE 9.5.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

The invention claimed is:

1. A compound having has the structure of Formula 3:

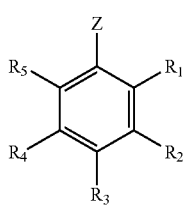

(3)

wherein $R_1$, $R_2$, $R_4$, and $R_5$ are independently hydrogen, alkyl, alkoxyl, or Z; and $Z_1$, $Z_2$, and Z independently have a structure of moiety A or moiety B:

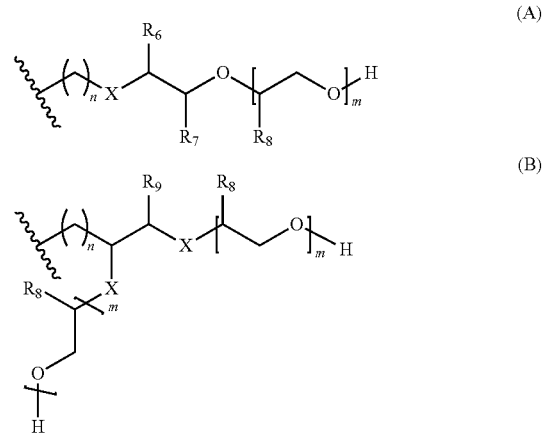

wherein
X is —O— or —N($R_{10}$)—;
n is an integer from 0 to 5;
$R_6$ and $R_9$ are independently hydrogen or alkyl;
$R_7$ is alkyl, or —(CH$_2$)z-O—$R_{11}$,
$R_8$ is independently hydrogen, alkyl, or aryl;
$R_{10}$ is hydrogen, alkyl, or Z;
$R_{11}$ is hydrogen or alkyl;
m is an integer from 3 to 20;
z is an integer from 1 to 10.

2. The compound of claim 1, wherein $R_1$, $R_2$, $R_4$, and $R_5$ are independently hydrogen or $C_1$ to $C_4$ alkyl.

3. The compound of claim 2, wherein $R_1$, $R_2$, $R_4$, and $R_5$ are hydrogen.

4. The compound of claim 2, wherein $R_6$ and $R_9$ are hydrogen.

5. The compound of claim 1, wherein $R_8$ is hydrogen or methyl.

6. The compound of claim 1, wherein $R_7$ is —(CH$_2$)z-O—$R_{11}$ and z is 1 to 3.

7. The compound of claim 6, wherein $R_{11}$ is $C_4$ to $C_{22}$ alkyl.

8. The compound of claim 7, wherein X is —O— or —N($R_{10}$)—.

9. The compound of claim 8, wherein X is —O—.

10. The compound of claim 8, wherein X is —N($R_{10}$)— and $R_{10}$ is hydrogen.

11. The compound of claim 1, wherein Z has the structure of moiety A, X is —O—, n is 0, $R_1$, $R_2$, $R_4$, $R_5$ are hydrogen, $R_6$ and $R_9$ are hydrogen, $R_7$ is (CH$_2$)z-O—$R_{11}$, z is 1, $R_8$ is hydrogen, $R_{11}$ is 2-ethylhexyl, and m is an integer from 7 to 13.

12. A compound of Formula 4 having the following structure:

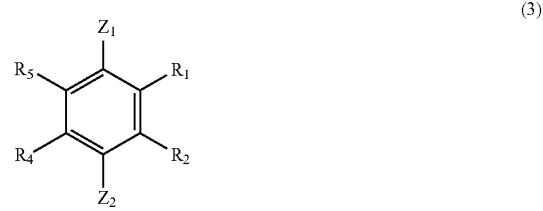

(3)

wherein $R_1$, $R_2$, $R_4$, and $R_5$ are independently hydrogen, alkyl, or alkoxyl;

$Z_1$ is has a structure of moiety C

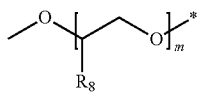
(C)

$Z_2$ has a structure of moiety D

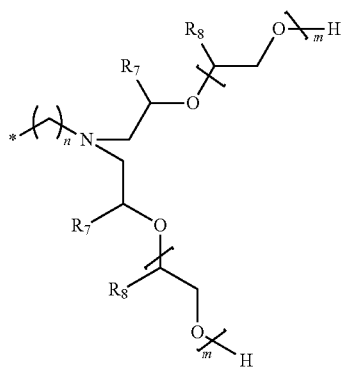
(D)

n is an integer from 0 to 5;

$R_7$ is alkyl, or —$(CH_2)z$-O—$R_{11}$, $R_8$ is independently hydrogen, alkyl, or aryl;

$R_{11}$ is hydrogen or alkyl;

m is an integer from 3 to 30; and z is an integer from 0 to 6.

13. The compound of claim 12, wherein n is 0, $R_7$ is —$(CH_2)z$-O—$R_{11}$, $R_8$ is hydrogen, Rug is 2-ethylhexyl, m is an integer from 10 to 30, and z is 1.

14. A polymer composition comprising:
a water-in-oil emulsion comprising an aqueous phase comprising water and a water-soluble or water-dispersible polymer, and an oil phase comprising an oil and an emulsifying agent; and an inversion surfactant comprising the compound of claim 1.

15. A detergent composition comprising a building agent and a surfactant, the surfactant comprising the compound of claim 1.

16. A method of cleaning a membrane, the method comprising contacting the membrane with a cleaning composition, the cleaning composition comprising the compound of claim 1.

* * * * *

UNITED STATES PATENT AND TRADEMARK OFFICE
CERTIFICATE OF CORRECTION

PATENT NO. : 11,414,626 B2  
APPLICATION NO. : 16/700843  
DATED : August 16, 2022  
INVENTOR(S) : Ashish Dhawan et al.

Page 1 of 1

It is certified that error appears in the above-identified patent and that said Letters Patent is hereby corrected as shown below:

In the Claims

Column 67, Claim 1, Line 54: after "having" delete "has".

Column 67, Claim 1, Line 55: delete " 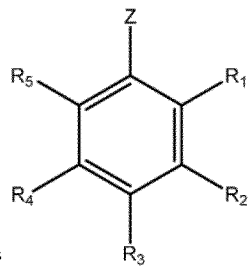 " and insert -- 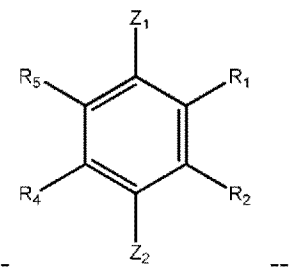 -- therefor.

Column 68, Claim 11, Line 51: delete "(CH2)z-O—R11," and insert -- —(CH2)z-O—$R_{11}$, -- therefor.

Column 69, Claim 12, Line 4: before "has" delete "is".

Column 70, Claim 13, Line 11: delete "Rug" and insert -- $R_{11}$ -- therefor.

Signed and Sealed this  
Second Day of May, 2023

*Katherine Kelly Vidal*

Katherine Kelly Vidal  
*Director of the United States Patent and Trademark Office*